US008748485B2

(12) United States Patent
Kokubo et al.

(10) Patent No.: US 8,748,485 B2
(45) Date of Patent: Jun. 10, 2014

(54) COMPOUND AND MEDICAL USE THEREOF

(75) Inventors: Masaya Kokubo, Osaka (JP); Koji Yano, Osaka (JP)

(73) Assignee: Ono Pharmaceuticals Co., Ltd., Osaka (JP)

(*) Notice: Subject to any disclaimer, the term of this patent is extended or adjusted under 35 U.S.C. 154(b) by 0 days.

(21) Appl. No.: 13/991,025

(22) PCT Filed: Dec. 1, 2011

(86) PCT No.: PCT/JP2011/077834
§ 371 (c)(1),
(2), (4) Date: May 31, 2013

(87) PCT Pub. No.: WO2012/074069
PCT Pub. Date: Jun. 7, 2012

(65) Prior Publication Data
US 2013/0245074 A1    Sep. 19, 2013

(30) Foreign Application Priority Data
Dec. 2, 2010 (JP) .................................. 2010-269046

(51) Int. Cl.
*A01N 37/34* (2006.01)
*A61K 31/275* (2006.01)
*A01N 37/12* (2006.01)
*A01N 37/44* (2006.01)
*A61K 31/195* (2006.01)
*C07C 229/00* (2006.01)
*A61K 31/198* (2006.01)
*C07C 229/36* (2006.01)

(52) U.S. Cl.
CPC ............ *A61K 31/198* (2013.01); *C07C 229/36* (2013.01)
USPC ............ 514/521; 514/565; 514/567; 562/444

(58) Field of Classification Search
None
See application file for complete search history.

(56) References Cited

U.S. PATENT DOCUMENTS

| 3,859,331 | A  | 1/1975  | Kaiser et al. |
| 7,342,131 | B2 | 3/2008  | Xiang et al. |
| 7,378,711 | B2 | 5/2008  | Suh et al. |
| 7,534,813 | B2 | 5/2009  | Xiang et al. |
| 7,563,821 | B2 | 7/2009  | Xiang et al. |
| 7,579,199 | B2 | 8/2009  | Suh et al. |
| 7,709,527 | B2 | 5/2010  | Xiang et al. |
| 7,940,456 | B2 | 5/2011  | Takagi et al. |
| 7,956,212 | B2 | 6/2011  | Xiang et al. |
| 7,968,597 | B2 | 6/2011  | Xiang et al. |
| 8,045,264 | B2 | 10/2011 | Takagi et al. |
| 8,163,958 | B2 | 4/2012  | Xiang et al. |
| 8,193,242 | B2 | 6/2012  | Xiang et al. |
| 8,236,157 | B2 | 8/2012  | Gebregiorgis |
| 8,324,272 | B2 | 12/2012 | Xiang et al. |
| 8,377,986 | B2 | 2/2013  | Hobbs et al. |
| 2005/0189883 | A1 | 9/2005  | Suh et al. |
| 2005/0282891 | A1 | 12/2005 | Xiang et al. |
| 2007/0115442 | A1 | 5/2007  | Takagi et al. |
| 2007/0225366 | A1 | 9/2007  | Xiang et al. |
| 2008/0132570 | A1 | 6/2008  | Xiang et al. |
| 2008/0176349 | A1 | 7/2008  | Suh et al. |
| 2008/0214663 | A1 | 9/2008  | Xiang et al. |
| 2009/0137834 | A1 | 5/2009  | Xiang et al. |
| 2009/0156679 | A1 | 6/2009  | Xiang et al. |
| 2009/0326067 | A1 | 12/2009 | Xiang et al. |
| 2010/0173992 | A1 | 7/2010  | Xiang et al. |
| 2010/0197953 | A9 | 8/2010  | Xiang et al. |
| 2010/0216878 | A1 | 8/2010  | Hobbs et al. |
| 2010/0264034 | A1 | 10/2010 | Gebregiorgis |
| 2011/0111062 | A1 | 5/2011  | Xiang et al. |
| 2011/0176210 | A1 | 7/2011  | Takagi et al. |
| 2011/0201817 | A1 | 8/2011  | Xiang et al. |
| 2012/0190861 | A1 | 7/2012  | Xiang et al. |
| 2012/0296109 | A1 | 11/2012 | Xiang et al. |

FOREIGN PATENT DOCUMENTS

| AU | 57016 73       | 12/1974 |
| DE | 21 53 800      | 5/1972  |
| JP | 2008 501704    | 1/2008  |
| JP | 2009 520690    | 5/2009  |
| JP | 47 31950       | 7/2011  |
| JP | 49 61135       | 6/2012  |
| WO | WO-2008 076458 | 6/2008  |
| WO | WO-2009 022098 | 2/2009  |
| WO | WO-2009 079387 | 6/2009  |

OTHER PUBLICATIONS

Supplementary European Search Report for EP 11 84 4106 dated Aug. 5, 2013.
International Search Report for PCT/JP2011/077834, Date of completion of international search: Feb. 29, 2012, Date of mailing of international search report: Mar. 13, 2012.
Office Action: Galzigna, L., et al., "Dopamine-Depleting Activity of L-3,4-(Dioxyphenylacetyl)-Phenylalanine," Neuropsychobiology, 1988; 19:180-185.

*Primary Examiner* — Jeffrey S. Lundgren
*Assistant Examiner* — William Lee
(74) *Attorney, Agent, or Firm* — Millen, White, Zelano & Branigan, P.C.

(57) ABSTRACT

Provided is a levodopa prodrug that overcomes the problems attributed to the blood kinetics of levodopa such as large number of doses and the incidence of side effects due to frequent dosing. (2S)-2-Amino-3-(3,4-bis((2-(benzoyloxy)-2-methylpropanoyl)oxy)phenyl)propanoic acid, a salt thereof, or a solvate thereof is a levodopa prodrug, and provides a flat blood concentration-time profile of levodopa through oral administration, and therefore is useful as a preventive and/or therapeutic agent for Parkinson's disease and/or Parkinson's syndrome that overcomes the problems associated with pharmaceutical preparations of levodopa.

44 Claims, 17 Drawing Sheets

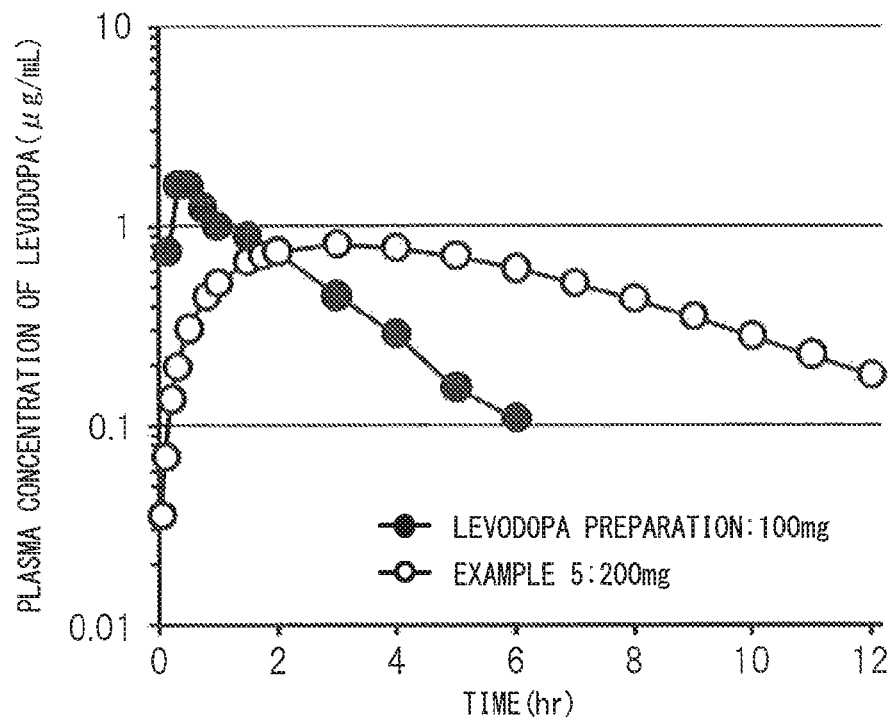
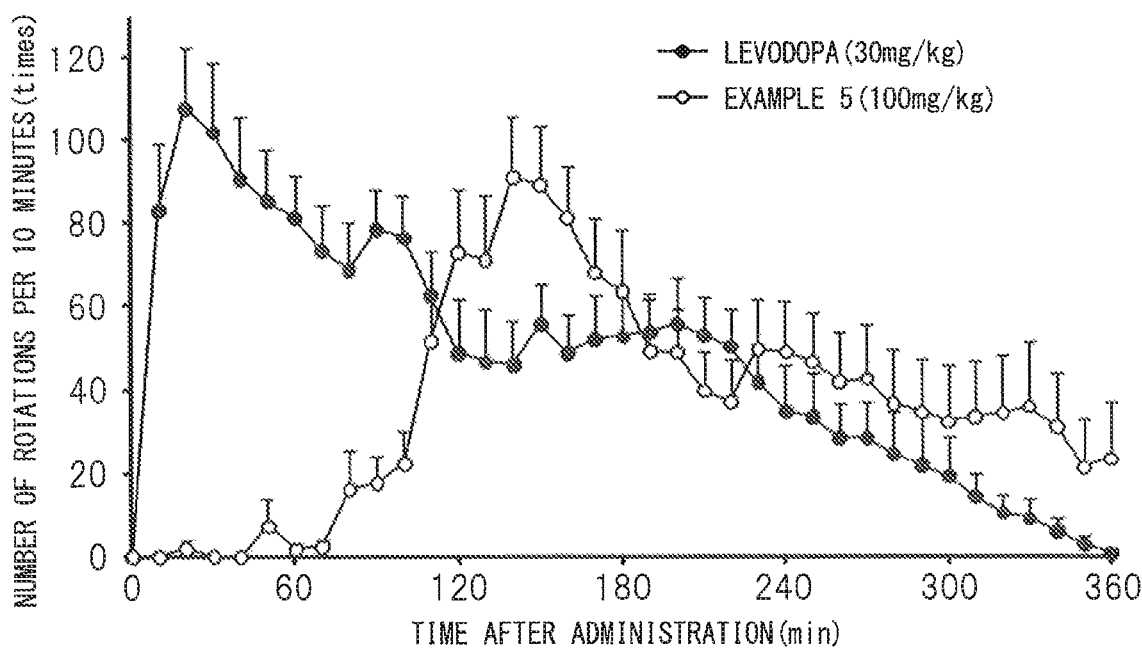

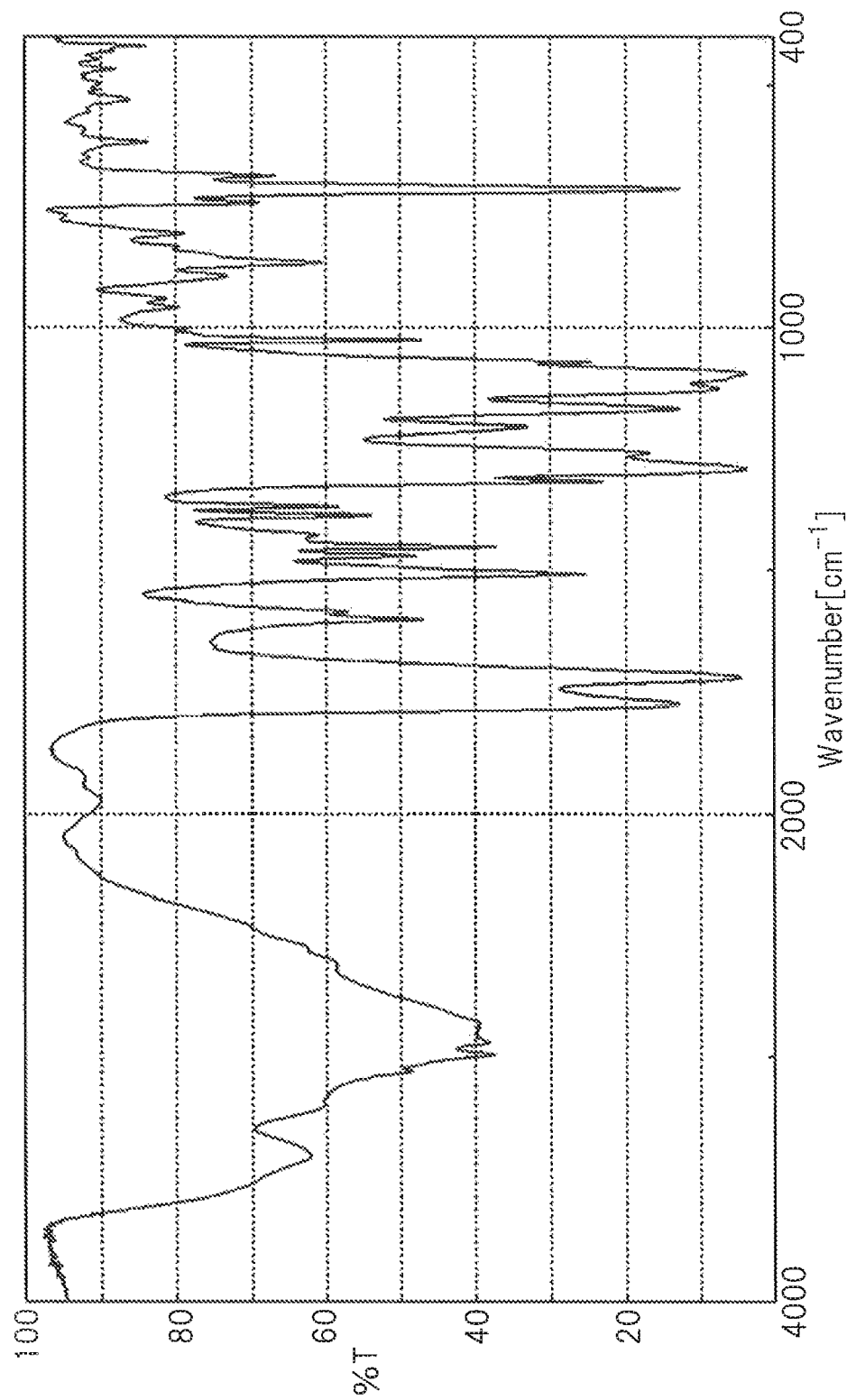

COMPOUND AND MEDICAL USE THEREOF

TECHNICAL FIELD

The present invention relates to (2S)-2-amino-3-(3,4-bis ((2-(benzoyloxy)-2-methylpropanoyl)oxy)phenyl)propanoic acid, a salt thereof, or a solvate thereof, and crystalline forms thereof, which is useful for prevention and/or treatment of Parkinson's disease and/or Parkinson's syndrome.

BACKGROUND ART

Parkinson's disease is one of the representative neurodegenerative diseases in the elderly caused by degeneration or loss of Dopamine neurons and is designated as a specified disease (intractable disease). The prevalence of Parkinson's disease is considered to be 100 to 300 people per 100,000 of the population, and the clinical symptoms can be roughly divided into motor symptoms and non-motor symptoms. As the motor symptoms, extrapyramidal symptoms such as tremor, akinesia, rigidity, and postural instability are observed, and among these, three symptoms: tremor, akinesia, and rigidity are known as three main characteristic features of Parkinson's disease.

On the other hand, as the non-motor symptoms, for example, gastrointestinal symptoms such as constipation and drooling, autonomic nervous symptoms such as orthostatic hypotension, postprandial hypotension, hyperhidrosis, oily skin, urination disorders, and erectile dysfunction, or psychiatric symptoms such as apathy, anhedonia, depressive symptoms, anxiety, and visual hallucination are developed. In addition, it is often the case that patients with Parkinson's disease also develop a cognitive impairment such as dementia.

Further, it is known that there are some cases where symptoms similar to those of Parkinson's disease are caused by diseases such as cerebrovascular disorders, brain tumors, and encephalitides, or side effects of drugs, intoxication, etc. other than Parkinson's disease. Those secondarily causing symptoms similar to those of Parkinson's disease are collectively called symptomatic parkinsonism, and symptomatic parkinsonism and primary parkinsonism such as Parkinson's disease are collectively called Parkinson's syndrome in some cases.

As a representative means for treating Parkinson's disease and/or Parkinson's syndrome, dopamine replacement therapy has been carried out. Levodopa (L-DOPA or L-3,4-dihydroxyphenylalanine), which is one of the drugs to be used in the dopamine replacement therapy, is a drug developed in the late 1960's, but has been still used at present as a first-choice drug in the treatment of Parkinson's disease.

However, levodopa has pharmacokinetic problems and also is one of the drugs whose blood concentration is difficult to be controlled at around an effective blood concentration. When levodopa is orally administered, levodopa is rapidly absorbed by an amino acid transporter present in the upper small intestine. The blood concentration of levodopa reaches a maximum value at about 30 minutes to 2 hours after oral administration, and the half-life of levodopa in the blood is about 1 hour, which is very short. Further, the absorption of levodopa is susceptible to the gastric residence time, the acidity of gastric acid, etc., and therefore is not stable.

Then, 95% or more of the absorbed levodopa is metabolized by an aromatic L-amino acid decarboxylase (AADC) in organs other than the central nervous system (particularly in liver) and rapidly converted into dopamine. Since dopamine cannot pass through the blood-brain barrier, dopamine produced in organs other than the central nervous system does not enter the brain. Therefore, it is considered that the percentage of levodopa which is distributed in the central nervous system and can exhibit its efficacy with respect to the absorbed levodopa is less than 1%.

As described above, since levodopa has pharmacokinetic problems that the absorption of levodopa is inconsistent, the blood retention time of levodopa is short, and the percentage of levodopa entered the central nervous system (brain uptake index) is low, levodopa is required to be taken 3 times or more per day, and some patients require to take levodopa as many as 12 times per day.

Moreover, levodopa also has a problem that the drug efficacy is gradually lost when several years have passed from the start of the treatment. This is because as the disease progresses, an ability to store dopamine in the brain decreases so that the range (therapeutic range) of blood concentration of levodopa, in which an appropriate therapeutic effect is obtained, is reduced. Due to this undesired property, even if a therapeutic effect is obtained by taking levodopa three times per day in a patient at present, after several years, the patient will have to take levodopa more than three times per day.

Since the problem of levodopa that "large number of doses are required" has been recognized from a long time ago, in order to overcome the problem and obtain even a slightly higher therapeutic effect on Parkinson's disease and/or Parkinson's syndrome, a method for administering levodopa at a high dose, or a method for inhibiting an aromatic L-amino acid decarboxylase in peripheral tissues was contemplated in the past. As for the inhibition of an aromatic L-amino acid decarboxylase in peripheral tissues, an inhibitor of the enzyme (DCI: a dopa decarboxylase inhibitor) has been developed, and a preparation obtained by adding a DCI to levodopa (a levodopa/DCI combination preparation) is clinically used at present. With respect to the levodopa/DCI combination preparation, the brain uptake index of levodopa has been improved as compared with the case where only levodopa is taken, and the dose of levodopa is decreased to about one-fifth. However, the half-life of levodopa in the blood does not change and is still about 1 hour or so even if a DCI is added, and therefore, from the viewpoint of maintaining the blood concentration of levodopa, there is nothing developed.

On the other hand, as for the administration of levodopa at a high dose, from the viewpoint of side effects, the implementation is not practical. The effective range of blood concentration of levodopa is narrow and also is close to the toxic range. In a case where a treatment was attempted by actually administering levodopa continuously at a dose close to the upper limit of the effective blood concentration or slightly exceeding the limit, side effects such as gastric symptoms, orthostatic hypotension, and palpitation were caused in the initial stage of the treatment, and after 2 to 3 months from the start of the treatment, dyskinesia and serious central nervous system side effects such as psychiatric symptoms were developed. Among the patients who require levodopa, there are not a few patients who cannot take levodopa at a sufficient dose due to such side effects.

The problem that levodopa requires "large number of doses" is not improved even by using levodopa and an inhibitor of levodopa metabolism in combination or by changing the administration route of levodopa itself. Further, side effects such as dyskinesia developed by frequent exposure to levodopa at a concentration exceeding the effective blood concentration are also problems which have been desired to be solved for patients who require levodopa.

In light of these circumstances, many prodrugs of levodopa itself have been reported so far for solving the problems attributed to the blood kinetics of levodopa such as "large number of doses" and "the incidence of side effects due to frequent dosing".

Examples of the prodrugs of levodopa include the following compounds:

a conjugate of levodopa and GABA represented by the general formula (A) described in WO 2009/101616:

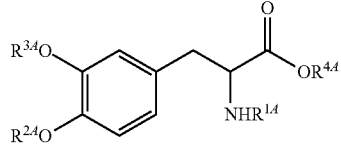

(A)

(wherein $R^{1A}$ to $R^{3A}$ each independently represent a hydrogen atom, a 4-aminobutyryl, or butyryl group; and $R^{4A}$ represents a hydrogen atom, an alkyl, butyryloxyalkyl, or 4-aminobutyryloxyalkyl group) (incidentally, the definitions of the respective groups are excerpts) (see PTL 1);

3,3-dimethyl-butyric acid 4-((S)-2-amino-2-methoxycarbonyl-ethyl)-2-(3,3-dimethyl-butyryloxy)phenyl ester represented by the formula (B) described in WO 2009/022098:

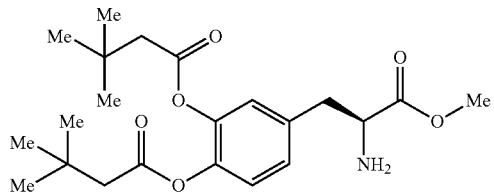

(B)

(see PTL 2);

a compound represented by the general formula (C) described in WO 2008/079387:

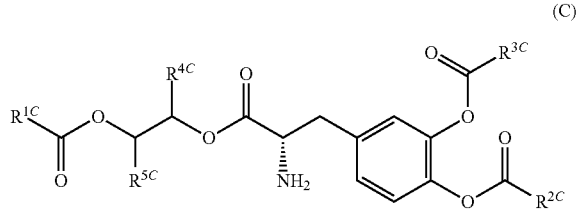

(C)

(wherein $R^{1C}$ represents C1-8 alkyl, substituted C1-8 alkyl, C1-8 alkoxy, or the like; $R^{2C}$ and $R^{1C}$ each independently represent C1-8 alkyl, substituted C1-8 alkyl, C1-8 alkoxy, or the like; and $R^{1C}$ and $R^{5C}$ each independently represent a hydrogen atom, C1-8 alkyl, substituted C1-8 alkyl, or the like) (incidentally, the definitions of the respective groups are excerpts) (see PTL 3);

a compound represented by the general formula (D) described in WO 2007/104959:

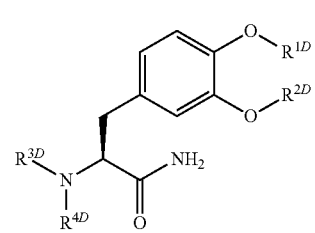

(D)

(wherein $R^{1D}$ and $R^{2D}$ each independently represent $-C(=O)R^{5D}$ or $-C(=O)OR^{5D}$, or at least one of $R^{1D}$ and $R^{2D}$ represents a hydrogen atom and the other represents $-C(=O)R^{5D}$ or $-C(=O)OR^{5D}$; $R^{3D}$ and $R^{4D}$ each independently represent a hydrogen atom, C1-C6 alkyl which may be substituted, C3-C6 cycloalkyl, or the like; $R^{5D}$ represents a hydrogen atom, C1-6 alkyl which may be substituted, or $-CH_2Q^D$; and $Q^D$ represents a 3- to 6-membered monocyclic carbocyclic ring or heterocyclic ring) (incidentally, the definitions of the respective groups are excerpts) (see PTL 4);

a compound represented by the general formula (E) described in WO 2007/109882:

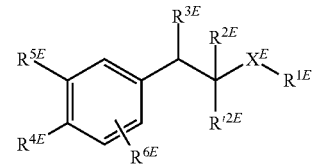

(E)

(wherein $X^E$ represents $NR^{7E}$ (wherein $R^{7E}$ represents a hydrogen atom, an acyl group, or the like); $R^{1E}$ represents a hydrogen atom, $NH_2$, C1-10 alkyl, or the like; $R^{2E}$ represents a hydrogen atom, C1-10 alkyl, or the like; $R'^{2E}$ represents a hydrogen atom, C1-10 alkyl, or the like; $R^{3E}$ represents a hydrogen atom, =O, $SR^{8E}$ (wherein $R^{8E}$ represents a hydrogen atom, C1-10 alkyl, or the like), or the like; $R^{4E}$ and $R^{5E}$ each independently represent OH, $NH_2$, or SH; and $R^{6E}$ represents a hydrogen atom, F, Cl, Br, I, or the like) (incidentally, the definitions of the respective groups are excerpts) (see PTL 5);

a compound represented by the general formula (F) described in WO 2006/119758:

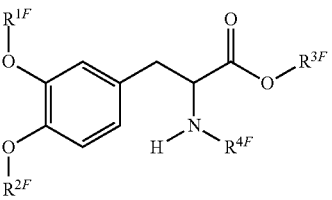

(F)

(wherein $R^{1F}$ and $R^{2F}$ each independently represent —H, —CO—H, —CO—CH$_3$, or the like; $R^{3F}$ represents —CH$_2$CH$_2$—$R^{5F}$, —H, —CH$_3$, —C$_2$H$_5$, or the like; $R^{1F}$ and $R^{5F}$ each independently represent —CO—$R^{6F}$, —CO—$R^{7F}$, —H, or the like; and $R^{6F}$ and $R^{7F}$ each independently represent a linear alkyl chain having 2 to 25 carbon atoms, a branched alkyl chain having 2 to 25 carbon atoms, or the like) (incidentally, the definitions of the respective groups are excerpts) (see PTL 6);

a compound represented by the general formula (G) described in WO 2005/121070:

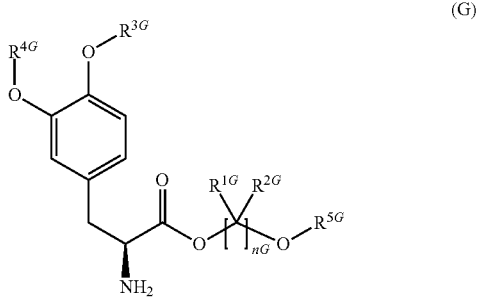

(G)

(wherein $R^{1G}$ and $R^{2G}$ each independently represent a hydrogen atom, alkyl, substituted alkyl, aryl, substituted aryl, or the like; $R^{3G}$ and $R^{4G}$ each independently represent a hydrogen atom, —C(O)OR$^{7G}$, C(O)R$^{7G}$, or the like; $R^{5G}$ is selected from alkyl, substituted alkyl, aryl, substituted aryl, and the like; $R^{7G}$ is selected from alkyl, substituted alkyl, cycloalkyl, substituted cycloalkyl, and the like; and nG represents an integer of 1 to 6) (incidentally, the definitions of the respective groups are excerpts) (see PTL 7);

a compound represented by the general formula (H) described in WO 2005/121069:

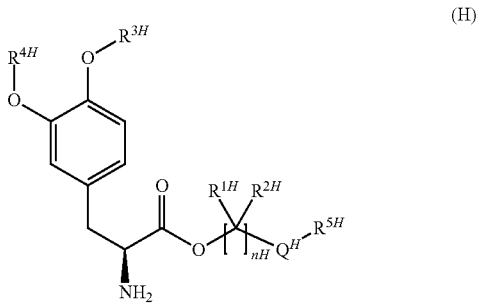

(H)

(wherein $Q^H$ is selected from —X$^H$—CO— and —CO—X$^H$—; X$^H$ is selected from —O— and —NR$^{6H}$; R$^{6H}$ is selected from a hydrogen atom, alkyl, substituted alkyl, aryl, substituted aryl, and the like; nH represents an integer of 2 to 4; $R^{1H}$ and $R^{2H}$ are each independently selected from a hydrogen atom, alkyl, substituted alkyl, aryl, substituted aryl, and the like; $R^{3H}$ and $R^{4H}$ are each independently selected from a hydrogen atom, —C(O)OR$^{7H}$, C(O)R$^{7H}$, and the like; R$^{5H}$ is selected from a hydrogen atom, alkyl, substituted alkyl, aryl, substituted aryl, and the like; and R$^{7H}$ is selected from alkyl, substituted alkyl, cycloalkyl, substituted cycloalkyl, and the like) (incidentally, the definitions of the respective groups are excerpts) (see PTL 8);

a compound represented by the general formula (J) described in European Patent Application Publication No. 728469:

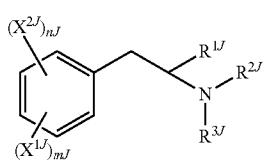

(J)

(wherein $X^{1J}$ represents a hydrogen atom, hydroxyl, methoxy, ethoxy, acetyloxy, or the like; $X^{2J}$ represents hydroxy, methoxy, ethoxy, acetyloxy, or the like; mJ+nJ is 5 or less; $R^{1J}$ represents carbonyl, alkoxycarbonyl, benzyloxycarbonyl, or the like; $R^{2J}$ represents a hydrogen atom, alkyl, alkylcarbonyl, alkyloxycarbonyl, benzyloxycarbonyl, or the like; and $R^{3J}$ represents a hydrogen atom, an alkyl group, or the like) (incidentally, the definitions of the respective groups are excerpts) (see PTL 9);

a compound represented by the general formula (K) described in Japanese Patent Application Publication No. S49-061135:

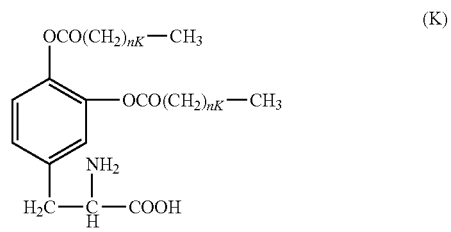

(K)

(wherein nK represents an integer of 0 to 2) (see PTL 10);

a compound represented by the general formula (L) described in German Patent Application Publication No. 2153800:

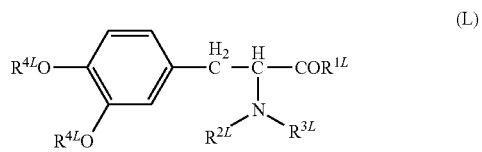

(L)

(wherein $R^{1L}$ represents C1-7 alkoxy, $C_{3-8}$ alkenylalkoxy, or phenyl C1-7 alkoxy; $R^{2L}$ represents a hydrogen atom; $R^{3L}$ represents a hydrogen atom, a substituent containing 1 to 18 carbon atoms, or the like; and $R^{4L}$ represents a substituent containing 1 to 18 carbon atoms or the like) (incidentally, the definitions of the respective groups are excerpts) (see PTL 11);

a compound represented by the general formula (M) described in U.S. Pat. No. 4,065,566:

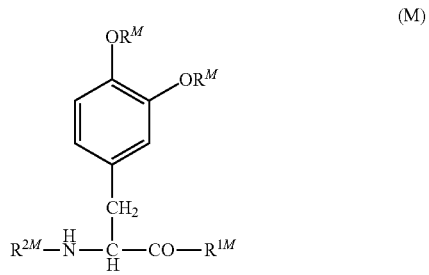

(M)

(wherein $R^M$ represents a hydrogen atom, an acyl group, or

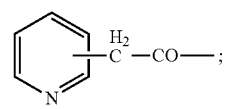

$R^{1M}$ represents a hydroxyl group or a —$OM^M$ group; $M^M$ represents an alkali metal or an ammonium ion; and $R^{2M}$ represents

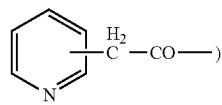

(incidentally, the definitions of the respective groups are excerpts) (see PTL 12);

a compound represented by the general formula (P) described in Japanese Patent Application Publication No. S47-031949:

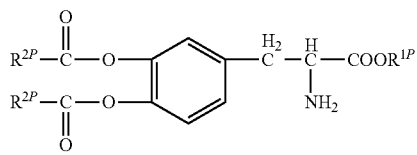

(P)

(wherein $R^{1P}$ represents a hydrogen atom or an ester residue; and $R^{2P}CO$ represents an organic acyl group) (incidentally, the definitions of the respective groups are excerpts) (see PTL 13);

a compound represented by the general formula (Q) described in Japanese Patent Application Publication No. S50-029527:

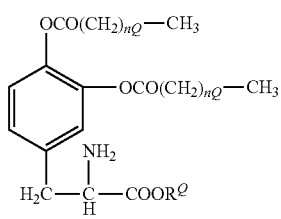

(Q)

(wherein nQ represents 0 to 2; and $R^Q$ represents $CH_3$ or $C_2H_5$) (see PTL 14);

a compound represented by the general formula (S) described in Japanese Patent Application Publication No. S48-072150:

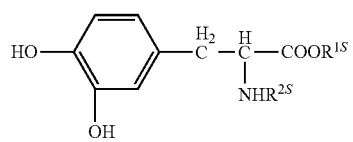

(S)

(wherein $R^{1S}$ represents a hydrogen atom, a lower alkyl group or a carboxyl-protecting group; and $R^{2S}$ represents an amino-protecting group) (see PTL 15);

a compound represented by the general formula (T) described in Japanese Patent Application Publication No. S47-031950:

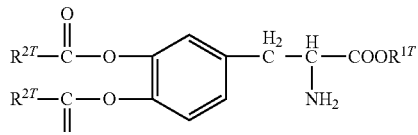

(T)

(wherein $R^{1T}$ represents a hydrogen atom or an ester residue; and $R^{2T}CO$ represents an organic acyl group) (incidentally, the definitions of the respective groups are excerpts) (see PTL 16);

a compound represented by the general formula (U) described in U.S. Pat. No. 3,998,799:

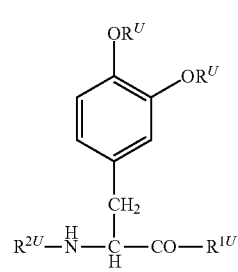

(U)

(wherein $R^U$ represents a hydrogen atom, an acyl group, or the like; $R^{1U}$ represents a hydroxyl group or a —$OM^U$ group; $M^U$ is selected from the group consisting of an alkali metal and an ammonium ion; $R^{2U}$ represents —$COR^{3U}$; and $R^{3U}$ represents an N,N—($C_1$-$C_2$)-dialkylamino acid, a $C_4$-$C_6$-cycloalkylamino acid, or the like) (incidentally, the definitions of the respective groups are excerpts) (see PTL 17); and a compound represented by the formula (V) described in Neuropsychobiology, 1988, Vol. 19, No. 4, PP. 180-185:

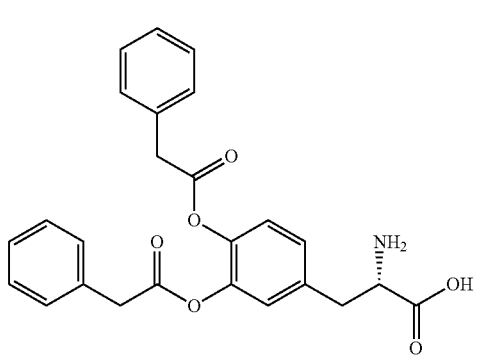

(V)

(see NPL 1).

However, (2S)-2-amino-3-(3,4-bis((2-(benzoyloxy)-2-methylpropanoyl)oxy)phenyl)propanoic acid, a salt thereof, or a solvate thereof, and the use thereof disclosed in the present invention are not described in any of these prior arts, and also are not derived from a combination of any of these prior arts.

CITATION LIST

Patent Literature

PTL 1: WO 2009/101616
PTL 2: WO 2009/022098

PTL 3: WO 2008/079387
PTL 4: WO 2007/104959
PTL 5: WO 2007/109882
PTL 6: WO 2006/119758
PTL 7: WO 2005/121070
PTL 8: WO 2005/121069
PTL 9: European Patent Application Publication No. 728469
PTL 10: Japanese Patent Application Publication No. S49-061135
PTL 11: German Patent Application Publication No. 2153800
PTL 12: U.S. Pat. No. 4,065,566
PTL 13: Japanese Patent Application Publication No. S47-031949
PTL 14: Japanese Patent Application Publication No. S50-029527
PTL 15: Japanese Patent Application Publication No. S48-072150
PTL 16: Japanese Patent Application Publication No. S47-031950
PTL 17: U.S. Pat. No. 3,998,799

Non Patent Literature

NPL 1: Neuropsychobiology, 1988, Vol. 19, No. 4, PP. 180-185

SUMMARY OF INVENTION

Technical Problem

An object of the present invention is to develop a levodopa prodrug that overcomes the pharmacokinetic problems of levodopa in patients with Parkinson's disease and/or Parkinson's syndrome and can provide an effective blood concentration of levodopa in small number of doses, more particularly, a levodopa prodrug that can provide an effective blood concentration (an effective plasma concentration: 0.4 to 1 μg/mL) of levodopa in humans with a flat blood concentration-time profile, and reduces the possibility of developing side effects such as dyskinesia or wearing-off as much as possible.

Solution to Problem

The inventors of the present invention made intensive studies in order to solve the above object, and as a result, they found that (2S)-2-amino-3-(3,4-bis((2-(benzoyloxy)-2-methylpropanoyl)oxy)phenyl)propanoic acid, which is a novel substance, solves the above object, and thus completed the present invention.

That is, the present invention relates to:

[1] (2S)-2-amino-3-(3,4-bis((2-(benzoyloxy)-2-methylpropanoyl)oxy)phenyl)propanoic acid, a salt thereof, or a solvate thereof;

[2] the compound according to the above [1], which is (2S)-2-amino-3-(3,4-bis((2-(benzoyloxy)-2-methylpropanoyl)oxy)phenyl)propanoic acid, (2S)-2-amino-3-(3,4-bis((2-(benzoyloxy)-2-methylpropanoyl)oxy)phenyl)propanoic acid tosylate, or (2S)-2-amino-3-(3,4-bis((2-(benzoyloxy)-2-methylpropanoyl)oxy)phenyl)propanoic acid hydrochloride;

[3] the compound according to the above [2], which is crystalline (2S)-2-amino-3-(3,4-bis((2-(benzoyloxy)-2-methylpropanoyl)oxy)phenyl)propanoic acid;

[4] the compound according to the above [3], which has a melting point of from about 177.0° C. to about 181.9° C.;

[5] the compound according to the above [3] or [4], which has at least peaks at 2θ of about 4.03, 7.21, 9.98, 10.72, 17.93, and 19.20 degrees in a powder X-ray diffraction spectrum;

[6] the compound according to any one of the above [3] to [5], which has peaks at 2θ of about 4.03, 7.21, 9.98, 10.72, 11.93, 12.90, 13.48, 14.65, 15.23, 15.99, 16.56, 17.23, 17.93, 19.20, 20.88, 21.66, 22.36, 22.50, and 24.58 degrees in a powder X-ray diffraction spectrum;

[7] the compound according to any one of the above [3] to [6], characterized by a powder X-ray diffraction spectrum chart shown in FIG. 4;

[8] the compound according to any one of the above [3] to [7], which has an exothermic peak at about 148.7° C. and also has endothermic peaks at about 184.7° C., about 194.7° C., and about 200.3° C. in differential scanning calorimetry;

[9] the compound according to any one of the above [3] to [8], characterized by a differential scanning calorimetry chart shown in FIG. 5;

[10] the compound according to any one of the above [3] to [9], which shows absorption at 1771, 1720, 1632, 1602, 1543, 1506, 1469, 1451, 1387, 1359, 1316, 1287, 1203, 1165, 1093, 1069, 1026, 957, 937, 898, 863, 802, 742, 710, 687, 615, 557, 526, 490, 482, 452, 424, 416, and 408 $cm^{-1}$ in an infrared absorption spectrum;

[11] the compound according to any one of the above [3] to [10], characterized by an infrared absorption spectrum chart shown in FIG. 6;

[12] the compound according to the above [3], which has a melting point of from about 174.7° C. to about 179.0° C.;

[13] the compound according to the above [3] or [12], which has at least a peak at 2θ of about 4.62 degrees in a powder X-ray diffraction spectrum;

[14] the compound according to any one of the above [3], [12], and [13], which has peaks at 2θ of about 4.62, 8.40, 9.54, 12.08, 15.38, and 18.16 degrees in a powder X-ray diffraction spectrum;

[15] the compound according to any one of the above [3] and [12] to [14], characterized by a powder X-ray diffraction spectrum chart shown in FIG. 7;

[16] the compound according to any one of the above [3] and [12] to [15], which has an exothermic peak at about 183.3° C. and also has endothermic peaks at about 192.2° C. and about 200.8° C. in differential scanning calorimetry;

[17] the compound according to any one of the above [3] and [12] to [16], characterized by a differential scanning calorimetry chart shown in FIG. 8;

[18] the compound according to any one of the above [3] and [12] to [17], which shows absorption at 1771, 1715, 1608, 1505, 1469, 1452, 1411, 1386, 1368, 1352, 1315, 1288, 1256, 1201, 1166, 1092, 1070, 1026, 955, 895, 865, 803, 744, 711, 675, 617, 605, 472, 444, 432, and 414 $cm^{-1}$ in an infrared absorption spectrum;

[19] the compound according to any one of the above [3] and [12] to [18], characterized by an infrared absorption spectrum chart shown in FIG. 9;

[20] the compound according to the above [2], which is crystalline (2S)-2-amino-3-(3,4-bis((2-(benzoyloxy)-2-methylpropanoyl)oxy)phenyl)propanoic acid tosylate;

[21] the compound according to the above [20], which has a melting point of from about 132.0° C. to about 136.0° C.;

[22] the compound according to the above [20] or [21], which has at least peaks at 2θ of about 10.97, 11.58, 14.83, 16.36, 16.70, 19.42, 20.58, and 21.69 degrees in a powder X-ray diffraction spectrum;

[23] the compound according to any one of the above [20] to [22], which has peaks at 2θ of about 5.15, 6.97, 7.46, 10.97, 11.58, 13.74, 14.83, 15.20, 16.10, 16.36, 16.70, 17.35, 18.30, 18.83, 19.42, 19.95, 20.58, 21.69, 22.63, 22.84, and 24.00 degrees in a powder X-ray diffraction spectrum;

[24] the compound according to any one of the above [20] to [23], characterized by a powder X-ray diffraction spectrum chart shown in FIG. 10;

[25] the compound according to any one of the above [20] to [24], which has an endothermic peak at about 135.95° C. in differential scanning calorimetry;

[26] the compound according to any one of the above [20] to [25], characterized by a differential scanning calorimetry chart shown in FIG. 11;

[27] the compound according to any one of the above [20] to [26], which shows absorption at 1780, 1712, 1599, 1508, 1452, 1388, 1316, 1289, 1217, 1166, 1120, 1090, 1071, 1036, 1026, 1010, 957, 900, 864, 817, 742, 713, 680, 622, 567, 550, 472, and 440 cm$^{-1}$ in an infrared absorption spectrum;

[28] the compound according to any one of the above [20] to [27], characterized by an infrared absorption spectrum chart shown in FIG. 12;

[29] the compound according to the above [20], which has a melting point of from about 132.3° C. to about 135.3° C.;

[30] the compound according to the above [20] or [29], which has at least peaks at 2θ of about 10.01, 11.88, 13.87, 15.01, 15.87, 16.07, 17.81, 18.65, 19.17, and 22.11 degrees in a powder X-ray diffraction spectrum;

[31] the compound according to any one of the above [20], [29], and [30], which has peaks at 2θ of about 4.04, 5.04, 5.54, 6.11, 6.60, 7.96, 8.62, 10.01, 10.32, 11.88, 12.88, 13.87, 15.01, 15.87, 16.07, 16.74, 17.17, 17.81, 18.65, 19.17, 19.72, 20.27, 20.93, 21.67, 22.11, 22.56, 23.11, 23.47, and 24.21 degrees in a powder X-ray diffraction spectrum;

[32] the compound according to any one of the above [20] and [29] to [31], characterized by a powder X-ray diffraction spectrum chart shown in FIG. 13;

[33] the compound according to any one of the above [20] and [29] to [32], which has an endothermic peak at about 134.54° C. in differential scanning calorimetry;

[34] the compound according to any one of the above [20] and [29] to [33], characterized by a differential scanning calorimetry chart shown in FIG. 14;

[35] the compound according to any one of the above [20] and [29] to [34], which shows absorption at 1781, 1711, 1600, 1507, 1315, 1287, 1220, 1203, 1166, 1119, 1088, 1070, 1036, 1027, 1010, 944, 898, 863, 816, 713, 681, 617, 567, 531, 517, 507, 484, 470, 452, 437, 421, and 413 cm$^{-1}$ in an infrared absorption spectrum;

[36] the compound according to any one of the above [20] and [29] to [35], characterized by an infrared absorption spectrum chart shown in FIG. 15;

[37] the compound according to the above [2], which is amorphous (2S)-2-amino-3-(3,4-bis((2-(benzoyloxy)-2-methylpropanoyl)oxy)phenyl)propanoic acid hydrochloride;

[38] the compound according to the above [37], which has a melting point of from about 112.0° C. to about 117.0° C.;

[39] the compound according to the above [37] or [38], characterized by a powder X-ray diffraction spectrum chart shown in FIG. 16;

[40] the compound according to any one of the above [37] to [39], which has an endothermic peak at about 82.83° C. in differential scanning calorimetry;

[41] the compound according to any one of the above [37] to [40], characterized by a differential scanning calorimetry chart shown in FIG. 17;

[42] the compound according to any one of the above [37] to [41], which shows absorption at 3409, 2992, 2944, 2865, 2629, 1970, 1774, 1718, 1655, 1601, 1585, 1508, 1470, 1452, 1428, 1388, 1369, 1317, 1290, 1258, 1204, 1168, 1125, 1093, 1070, 1026, 1003, 958, 866, 806, 741, 714, 687, 617, 530, 496, 467, 447, and 419 cm$^{-1}$ in an infrared absorption spectrum;

[43] the compound according to any one of the above [37] to [42], characterized by an infrared absorption spectrum chart shown in FIG. 18;

[44] a pharmaceutical composition comprising (2S)-2-amino-3-(3,4-bis((2-(benzoyloxy)-2-methylpropanoyl)oxy)phenyl)propanoic acid, a salt thereof, or a solvate thereof;

[45] the pharmaceutical composition according to the above [44], which is a preventive and/or therapeutic agent for Parkinson's disease and/or Parkinson's syndrome;

[46] a medicament comprising a combination of (2S)-2-amino-3-(3,4-bis((2-(benzoyloxy)-2-methylpropanoyl)oxy)phenyl)propanoic acid, a salt thereof, or a solvate thereof, and an aromatic L-amino acid decarboxylase inhibitor, and/or a catechol-O-methyltransferase inhibitor;

[47] the medicament according to the above [46], wherein the aromatic L-amino acid decarboxylase inhibitor is carbidopa hydrate or benserazide hydrochloride;

[48] the medicament according to the above [46], wherein the catechol-O-methyltransferase inhibitor is entacapone, tolcapone, nitecapone, BIA-3-202, or CGP-28014;

[49] the medicament according to any one of the above [46] to [48], which is a combination preparation;

[50] a method for preventing and/or treating Parkinson's disease and/or Parkinson's syndrome, characterized by comprising administering to a mammal an effective amount of (2S)-2-amino-3-(3,4-bis((2-(benzoyloxy)-2-methylpropanoyl)oxy)phenyl)propanoic acid, a salt thereof, or a solvate thereof;

[51] the method for prevention and/or treatment according to the above [50], which further comprises administering an effective amount of an aromatic L-amino acid decarboxylase inhibitor and/or a catechol-β-methyltransferase inhibitor;

[52] (2S)-2-amino-3-(3,4-bis((2-(benzoyloxy)-2-methylpropanoyl)oxy)phenyl)propanoic acid, a salt thereof, or a solvate thereof for preventing and/or treating Parkinson's disease and/or Parkinson's syndrome;

[53] (2S)-2-amino-3-(3,4-bis((2-(benzoyloxy)-2-methylpropanoyl)oxy)phenyl)propanoic acid, a salt thereof, or a solvate thereof to be used in combination with an aromatic L-amino acid decarboxylase inhibitor and/or a catechol-O-methyltransferase inhibitor upon preventing and/or treating Parkinson's disease and/or Parkinson's syndrome;

[54] use of (2S)-2-amino-3-(3,4-bis((2-(benzoyloxy)-2-methylpropanoyl)oxy)phenyl)propanoic acid, a salt thereof, or a solvate thereof for manufacture of a preventive and/or therapeutic agent for Parkinson's disease and/or Parkinson's syndrome;

[55] a preventive and/or therapeutic agent for Parkinson's disease and/or Parkinson's syndrome, which comprises (2S)-2-amino-3-(3,4-bis((2-(benzoyloxy)-2-methylpropanoyl)oxy)phenyl)propanoic acid, a salt thereof, or a solvate thereof;

[56] (S)-((4-(3-(benzyloxy)-2-((tert-butoxycarbonyl)amino)-3-oxopropyl)-1,2-phenylene)bis(oxy))bis(2-methyl-1-oxopropan-2,1-diyl)dibenzoate or a salt thereof; and

[57] (S)-3-(3,4-bis((2-(benzoyloxy)-2-methylpropanoyl)oxy)phenyl)-2-((tert-butoxycarbonyl)amino)propanoic acid or a salt thereof.

Advantageous Effects of Invention (2S)-2-Amino-3-(3,4-bis((2-(benzoyloxy)-2-methylpropanoyl)oxy)phenyl)propanoic acid, a salt thereof, or a solvate thereof (hereinafter, sometimes collectively abbreviated as "compound of the present invention") is a levodopa prodrug that overcomes the pharmacokinetic problems of levodopa and can provide an effective blood concentration of levodopa in small number of doses. By taking the compound of the present invention in place of levodopa, an effective blood concentration of levodopa can be maintained for about 16 hours in two doses per day (at most three doses per day) in patients with Parkinson's disease and/or Parkinson's syndrome who took levodopa in the past, preferably patients with Parkinson's disease and/or Parkinson's syndrome who took levodopa in combination with a DCI in the past. Since the same efficacy can be obtained by dosing two times per day, also the drug compliance can be improved in patients who had to take a levodopa preparation in 6 to 12 doses per day.

Further, the compound of the present invention is a prodrug capable of providing an effective blood concentration (an effective plasma concentration: 0.4 to 1 µg/mL) of levodopa for a long period of time in humans, and reduces the possibility of developing side effects such as dyskinesia or wearing-off as much as possible by providing a flat blood concentration-time profile of levodopa.

In addition, the compound of the present invention is a drug which raises no concern about mutagenicity. The examination made by the inventors of the present invention revealed that among levodopa prodrugs, particularly some compounds showing long blood retention, there are not a few compounds confirmed to have mutagenicity in a mutagenicity assay using mammalian cells. However, since the compound of the present invention does not have mutagenicity, even in the case where a drug has to be taken over a period as long as several years or several decades such as Parkinson's disease and/or Parkinson's syndrome, patients can continue to take the drug without worrying.

BRIEF DESCRIPTION OF DRAWINGS

FIG. 2 shows a simulation of a plasma concentration-time profile of levodopa in humans obtained using the kinetic data of levodopa or the compound of the present invention in dogs under the condition of using a DCI (carbidopa) in combination.

FIG. 3 shows a change in rotational behavior when levodopa or the compound of the present invention was administered under the condition of using a DCI (benserazide) in combination to a rat model injected with 6-hydroxydopamine into the medial forebrain bundle.

FIG. 18 shows an infrared absorption spectrum chart of amorphous (2S)-2-amino-3-(3,4-bis((2-(benzoyloxy)-2-methylpropanoyl)oxy)phenyl)propanoic acid hydrochloride obtained in Example 5.

DESCRIPTION OF EMBODIMENTS

Figure 1:
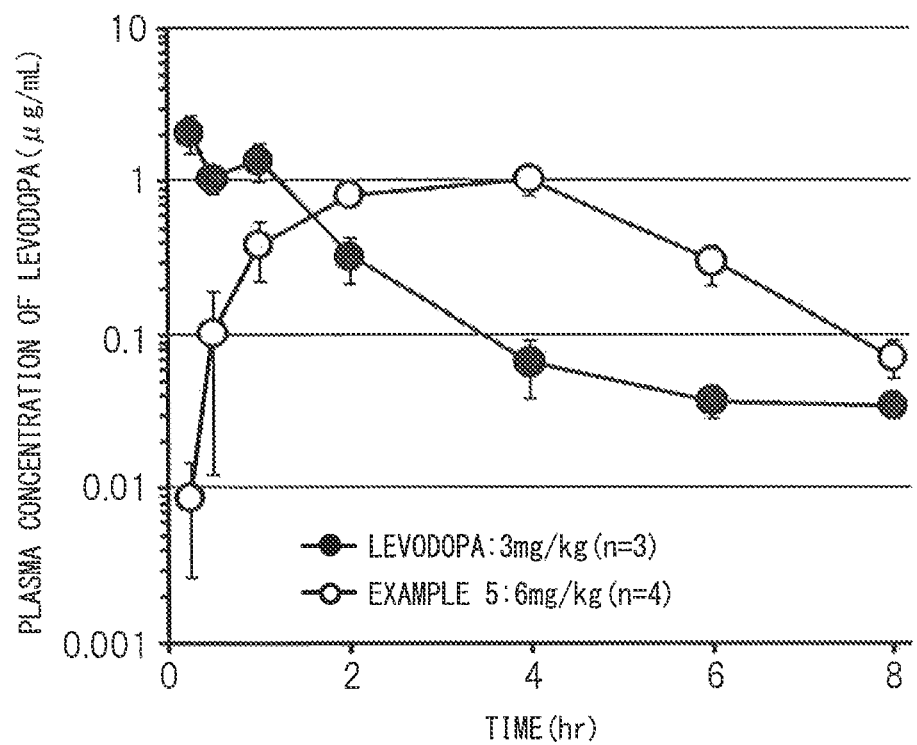
FIG. 1 shows a plasma concentration-time profile of levodopa when levodopa or the compound of the present invention was administered to dogs under the condition of using a DCI (carbidopa) in combination.

In the present invention, (2S)-2-amino-3-(3,4-bis((2-(benzoyloxy)-2-methylpropanoyl)oxy)phenyl)propanoic acid is a compound represented by the following formula.

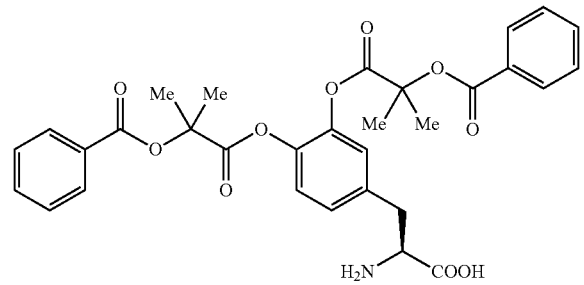 [SMILES: CC(C)(OC(=O)c1ccccc1)C(=O)Oc1ccc(C[C@H](N)C(=O)O)cc1OC(=O)C(C)(C)OC(=O)c1ccccc1]

As is appreciated by those skilled in the art, in the present invention, unless otherwise specified, the symbol

⦚ indicates that the substituent attached thereto is behind the sheet (i.e. α-configuration); the symbol

╱ indicates that the substituent attached thereto is in front of the sheet (i.e. β-configuration); and the symbol

╱ indicates that the substituent attached thereto is in α-configuration, β-configuration, or a mixture thereof at an arbitrary ratio.

In the present invention, unless otherwise specified, all isomers are included. For example, isomers due to the presence of asymmetric carbon or the like (R-isomer, S-isomer, α-configuration, β-configuration, enantiomers, and diastereomers), optically active isomers having optical activity (D-isomer, L-isomer, d-isomer, and 1-isomer), polar compounds in chromatographic separation (high-polar compounds and low-polar compounds), equilibrium compounds (such as tautomers with an amide bond), rotational isomers, mixtures thereof at an arbitrary ratio, and racemic mixtures are all included in the present invention.

In the present invention, (2S)-2-amino-3-(3,4-bis((2-(benzoyloxy)-2-methylpropanoyl)oxy)phenyl)propanoic acid is converted into a corresponding salt by a known method. As the salt, a water-soluble salt is preferred. Examples of a suitable salt include acid addition salts (such as inorganic acid salts such as hydrochlorides, hydrobromides, hydroiodides, sulfates, phosphates, and nitrates; and organic acid salts such as acetates, lactates, tartrates, benzoates, citrates, methanesulfonates, ethanesulfonates, benzenesulfonates, toluenesulfonates, p-toluenesulfonates (tosylates), isethionates, glucuronates, and gluconates), salts of natural acidic amino acids (such as aspartic acid and glutamic acid), salts of alkali metals (such as potassium and sodium), salts of alkaline earth metals (such as calcium and magnesium), ammonium salts, tetramethyl ammonium salts, tetrabutyl ammonium salts, salts of pharmaceutically acceptable organic amines (such as alkylamines (such as methylamine, dimethylamine, trimethylamine, and triethylamine), heterocyclic amines (such as pyridine, picoline, and piperidine), alkanolamines (such as ethanolamine, diethanolamine, and triethanolamine), dicyclohexylamine, N,N'-dibenzylethylenediamine, cyclopentylamine, benzylamine, dibenzylamine, phenethylamine, tris (hydroxymethyl)methylamine, and N-methyl-D-glucamine), and salts of natural basic amino acids (such as arginine, lysine, ornithine, and histidine).

(2S)-2-Amino-3-(3,4-bis((2-(benzoyloxy)-2-methylpropanoyl)oxy)phenyl)propanoic acid and a salt thereof can also be converted into a solvate. The solvate is preferably low-toxic and water-soluble. Examples of a suitable solvate include solvates with, for example, water or an alcoholic solvent (such as ethanol).

In addition, each atom constituting (2S)-2-amino-3-(3,4-bis((2-(benzoyloxy)-2-methylpropanoyl)oxy)phenyl)propanoic acid, a salt thereof, or a solvate thereof may be substituted with an isotope thereof (such as $^2H$, $^3H$, $^{13}Cr$, $^{14}C$, $^{35}S$, or $^{125}I$), or the like as needed.

In the present invention, (2S)-2-amino-3-(3,4-bis((2-(benzoyloxy)-2-methylpropanoyl)oxy)phenyl)propanoic acid, a salt thereof, or a solvate thereof, that is, the compound of the present invention is not limited to the crystal form thereof, and may be crystalline or amorphous, or may be a mixture of a crystalline compound and an amorphous compound at an arbitrary ratio. It can be determined as to what crystal form the compound of the present invention has by performing measurement using known analytical methods to be used for crystallographic analysis such as powder X-ray diffraction spectrometry, differential scanning calorimetry, infrared absorption spectrometry, and a melting point determination method alone or in combination.

It has been confirmed that among the compounds of the present invention, for example, (2S)-2-amino-3-(3,4-bis((2-(benzoyloxy)-2-methylpropanoyl)oxy)phenyl)propanoic acid has at least two crystal forms (which are referred to as type A crystal and type B crystal in a distinguishable manner in the present description for the sake of convenience).

Figure 4:
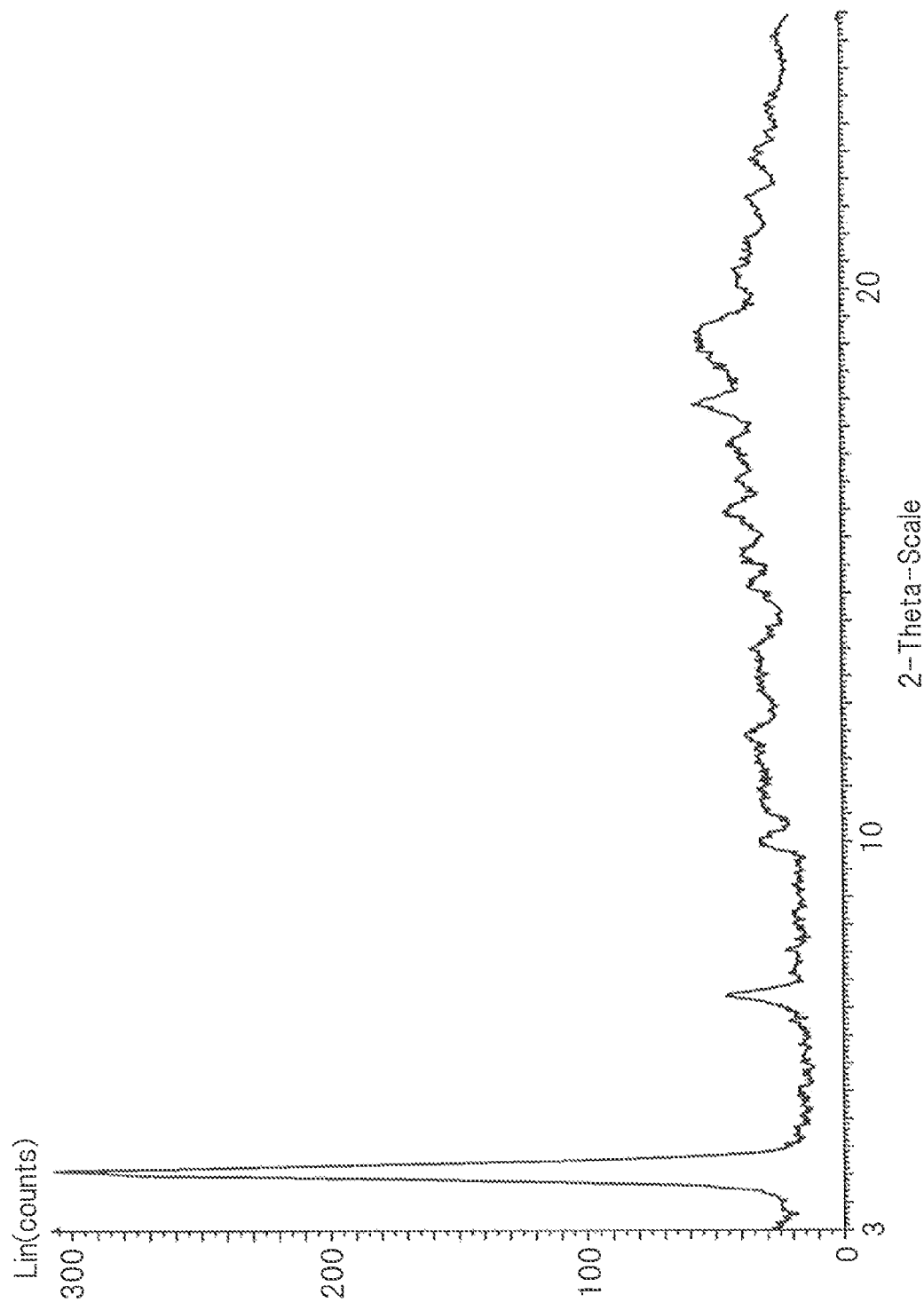
FIG. 4 shows a powder X-ray diffraction spectrum chart of crystalline (2S)-2-amino-3-(3,4-bis((2-(benzoyloxy)-2-methylpropanoyl)oxy)phenyl)propanoic acid (type A crystal) obtained in Example 9.

The type A crystal of (2S)-2-amino-3-(3,4-bis((2-(benzoyloxy)-2-methylpropanoyl)oxy)phenyl)propanoic acid is characterized in that, for example, in an analysis by powder X-ray diffraction spectrometry, it has at least peaks at 2θ of about 4.03, 7.21, 9.98, 10.72, 17.93, and 19.20 degrees, preferably it has peaks at 2θ of about 4.03, 7.21, 9.98, 10.72, 11.93, 12.90, 13.48, 14.65, 15.23, 15.99, 16.56, 17.23, 17.93, 19.20, 20.88, 21.66, 22.36, 22.50, and 24.58 degrees, more preferably it shows data shown in Table 3 in the below-described Example 9, particularly preferably it shows substantially the same data as a powder X-ray diffraction spectrum chart shown in FIG. 4.

Figure 5:
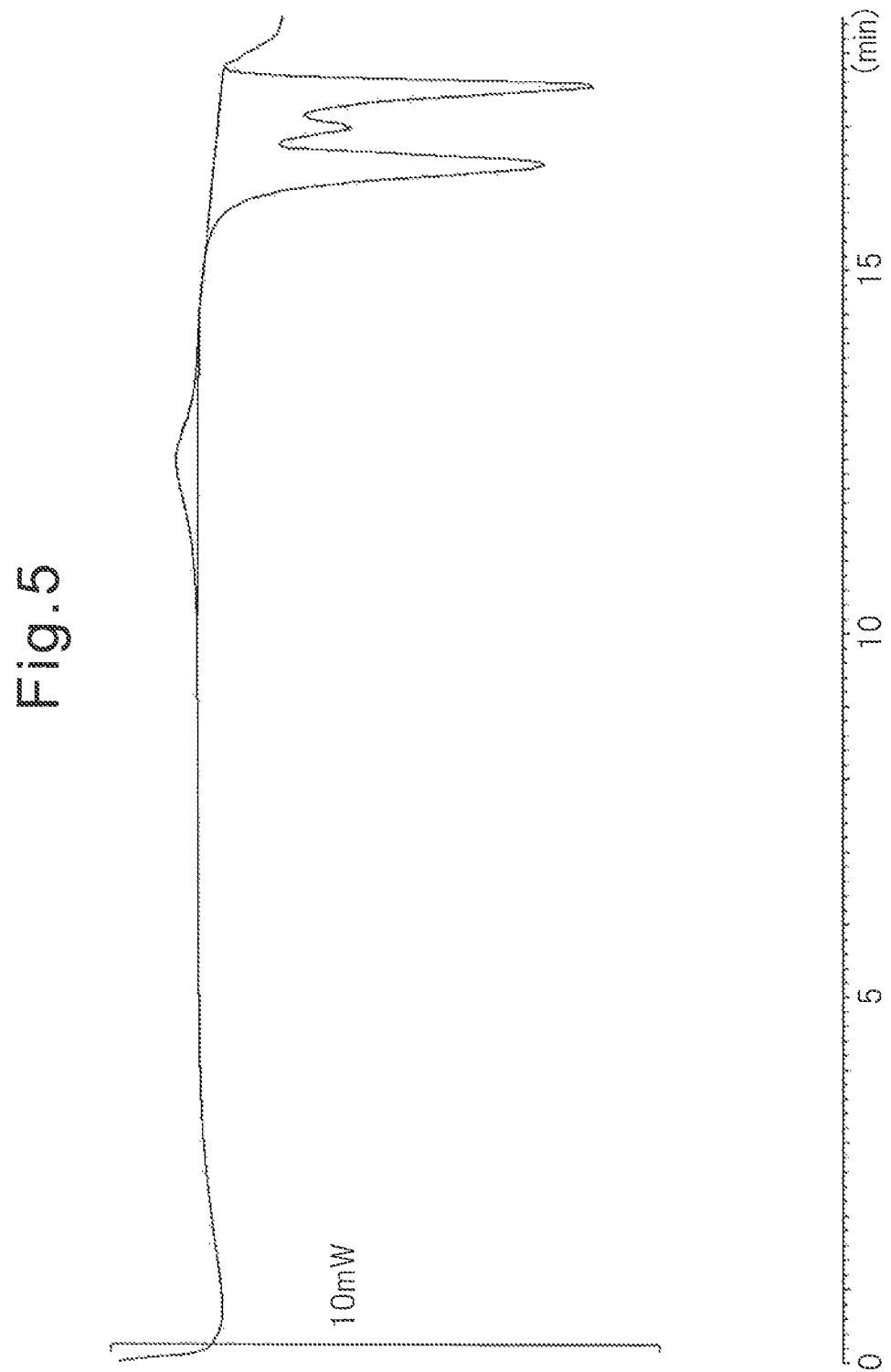
FIG. 5 shows a differential scanning calorimetry chart of crystalline (2S)-2-amino-3-(3,4-bis((2-(benzoyloxy)-2-methylpropanoyl)oxy)phenyl)propanoic acid (type A crystal) obtained in Example 9.

The type A crystal of (2S)-2-amino-3-(3,4-bis((2-(benzoyloxy)-2-methylpropanoyl)oxy)phenyl)propanoic acid is characterized in that, for example, in an analysis by differential scanning calorimetry, it has an exothermic peak at around 148.7° C. and also has endothermic peaks at around 184.7° C., 194.7° C., and 200.3° C., preferably it shows substantially the same data as a differential scanning calorimetry chart shown in FIG. 5.

Figure 6:
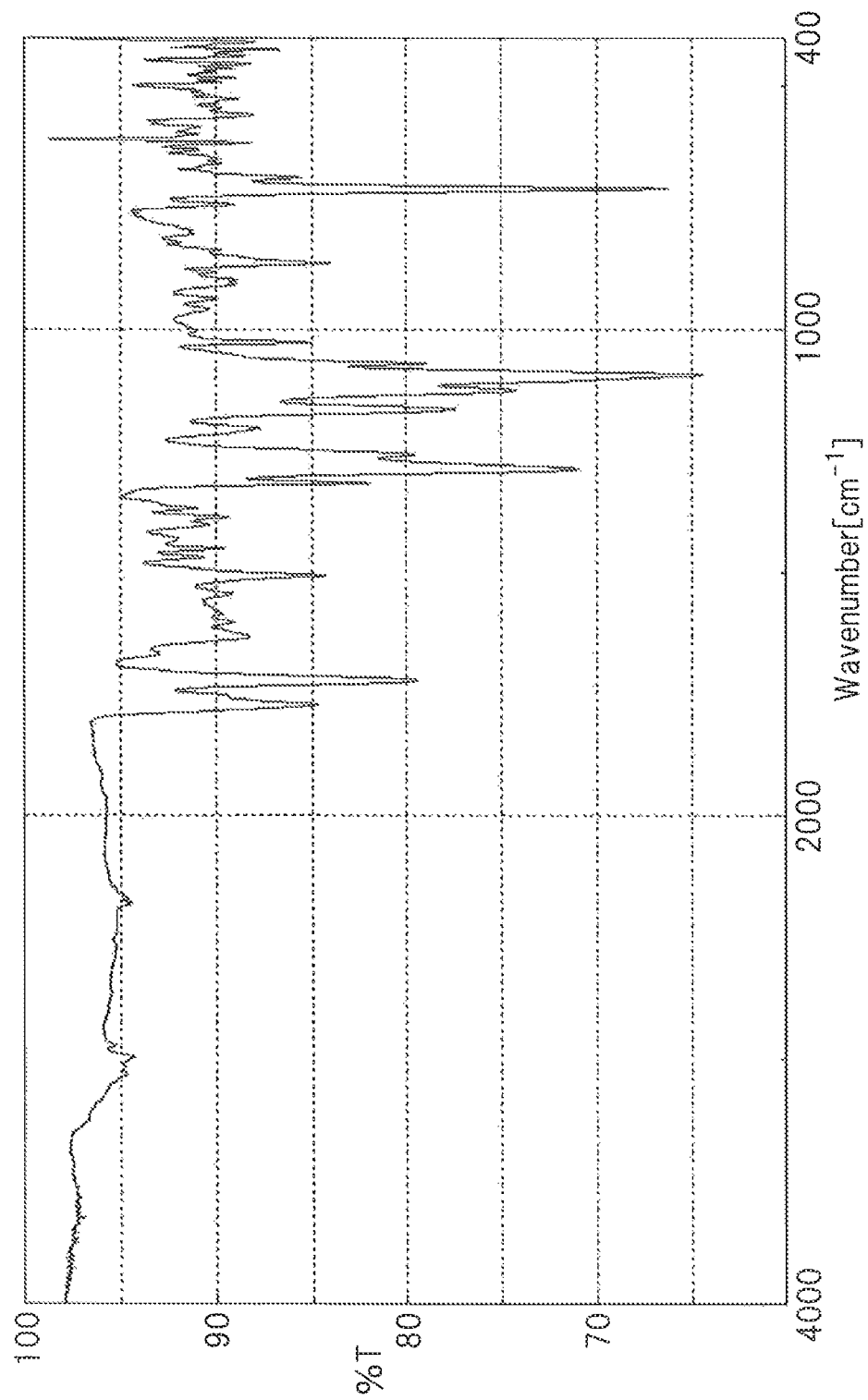
FIG. 6 shows an infrared absorption spectrum chart of crystalline (2S)-2-amino-3-(3,4-bis((2-(benzoyloxy)-2-methylpropanoyl)oxy)phenyl)propanoic acid (type A crystal) obtained in Example 9.

The type A crystal of (2S)-2-amino-3-(3,4-bis((2-(benzoyloxy)-2-methylpropanoyl)oxy)phenyl)propanoic acid is characterized in that, for example, in an analysis by infrared absorption spectrometry, it shows absorption at 1771, 1720, 1632, 1602, 1543, 1506, 1469, 1451, 1387, 1359, 1316, 1287, 1203, 1165, 1093, 1069, 1026, 957, 937, 898, 863, 802, 742, 710, 687, 615, 557, 526, 490, 482, 452, 424, 416, and 408 $cm^{-1}$, preferably it shows substantially the same data as an infrared absorption spectrum chart shown in FIG. 6.

The type A crystal of (2S)-2-amino-3-(3,4-bis((2-(benzoyloxy)-2-methylpropanoyl)oxy)phenyl)propanoic acid is characterized in that, for example, in an analysis by a melting point determination method, it has a melting point of from about 177.0° C. to 181.9° C.

The type B crystal of (2S)-2-amino-3-(3,4-bis((2-(benzoyloxy)-2-methylpropanoyl)oxy)phenyl)propanoic acid is characterized in that, for example, in an analysis by powder X-ray diffraction spectrometry, it has at least a peak at 2θ of about 4.62 degrees, preferably it has peaks at 2θ of about 4.62, 8.40, 9.54, 12.08, 15.38, and 18.16 degrees, more preferably it shows data shown in Table 4 in the below-described Example 10, particularly preferably it shows substantially the same data as a powder X-ray diffraction spectrum chart shown in FIG. 7.

Figure 8:
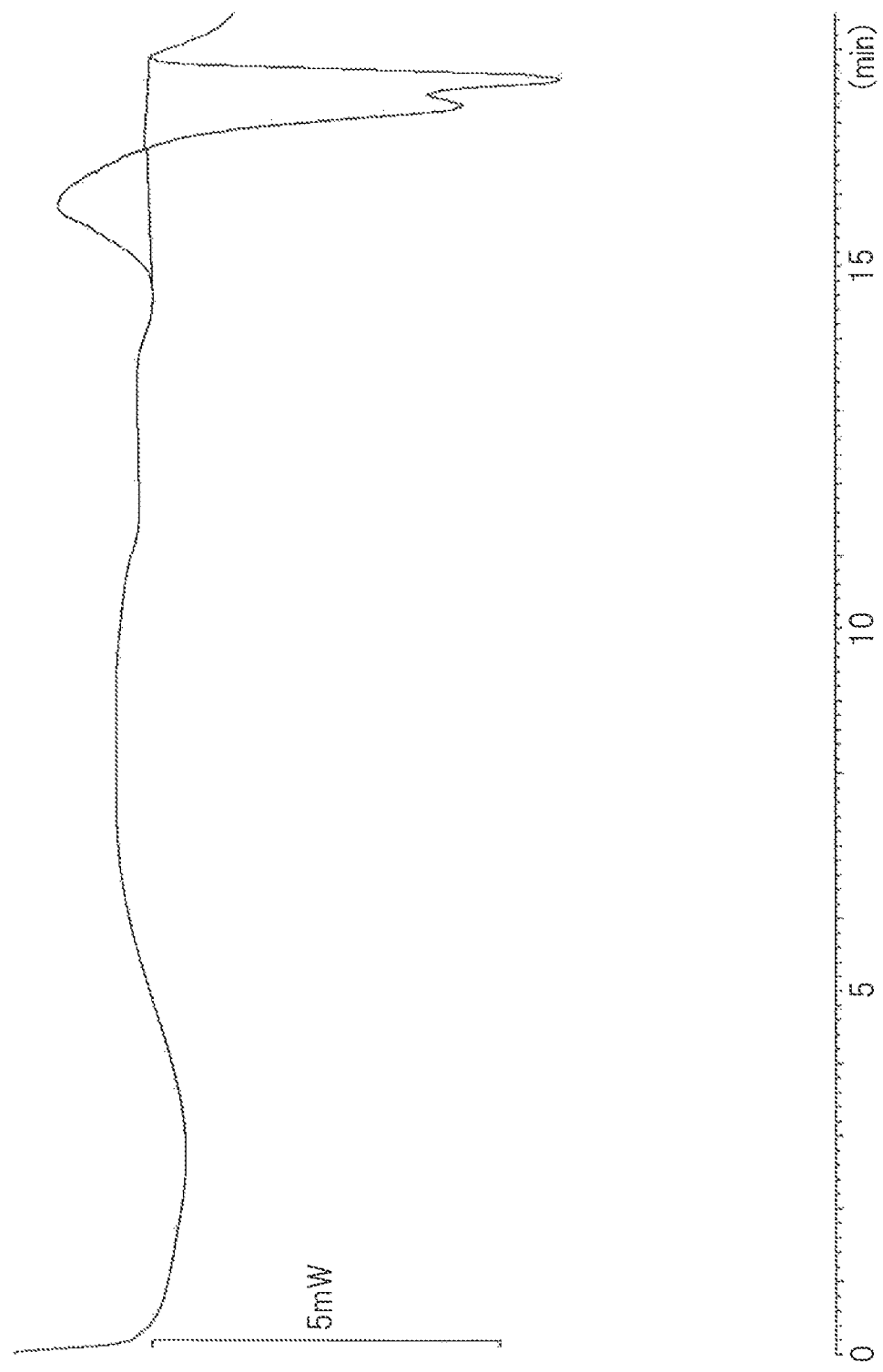
FIG. 8 shows a differential scanning calorimetry chart of crystalline (2S)-2-amino-3-(3,4-bis((2-(benzoyloxy)-2-methylpropanoyl)oxy)phenyl)propanoic acid (type B crystal) obtained in Example 10.

The type B crystal of (2S)-2-amino-3-(3,4-bis((2-(benzoyloxy)-2-methylpropanoyl)oxy)phenyl)propanoic acid is characterized in that, for example, in an analysis by differential scanning calorimetry, it has an exothermic peak at around 183.3° C. and also has endothermic peaks at around 192.2° C. and 200.8° C., preferably it shows substantially the same data as a differential scanning calorimetry chart shown in FIG. 8.

Figure 9:
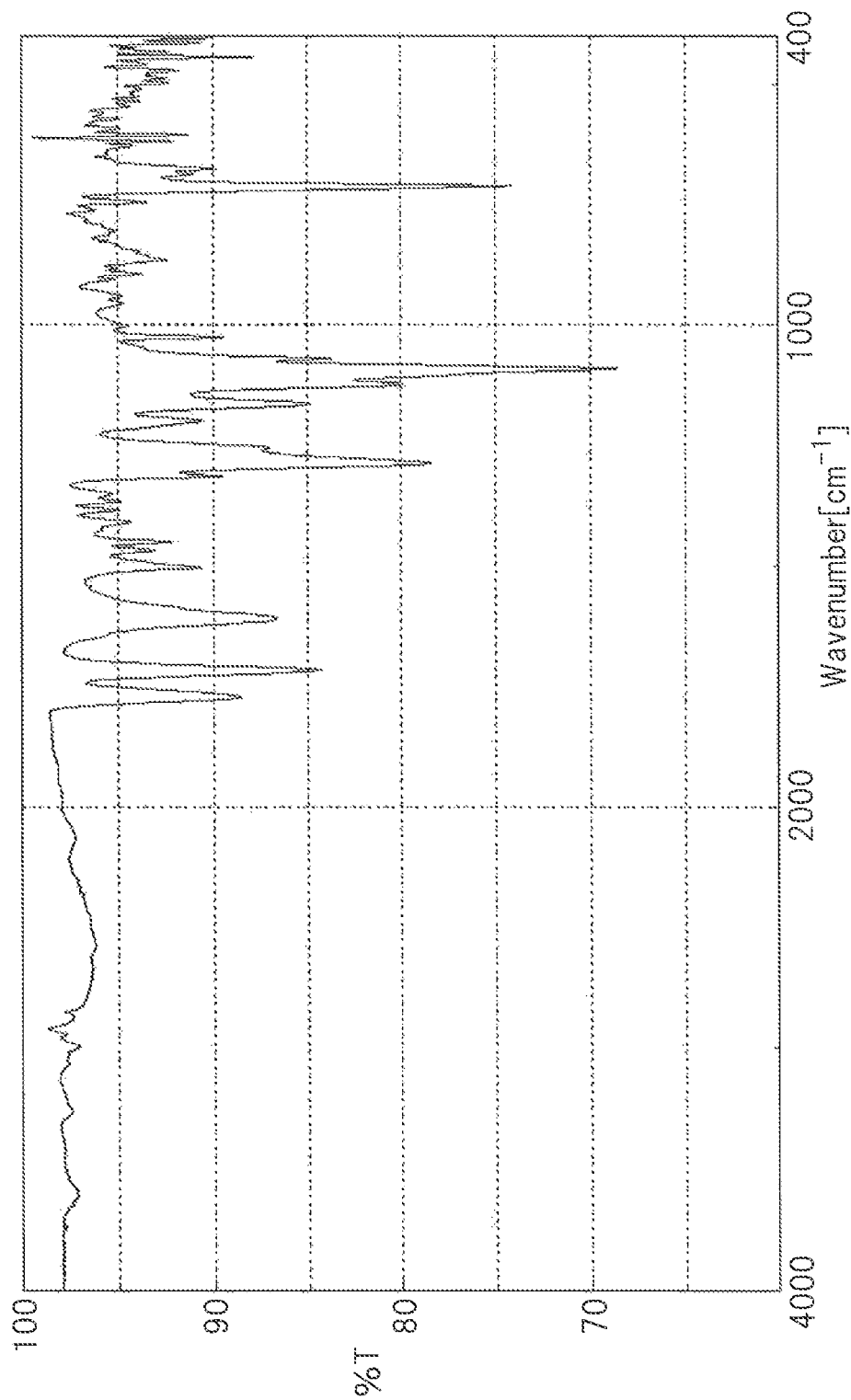
FIG. 9 shows an infrared absorption spectrum chart of crystalline (2S)-2-amino-3-(3,4-bis((2-(benzoyloxy)-2-methylpropanoyl)oxy)phenyl)propanoic acid (type B crystal) obtained in Example 10.

The type B crystal of (2S)-2-amino-3-(3,4-bis((2-(benzoyloxy)-2-methylpropanoyl)oxy)phenyl)propanoic acid is characterized in that, for example, in an analysis by infrared absorption spectrometry, it shows absorption at 1771, 1715, 1608, 1505, 1469, 1452, 1411, 1386, 1368, 1352, 1315, 1288, 1256, 1201, 1166, 1092, 1070, 1026, 955, 895, 865, 803, 744, 711, 675, 617, 605, 472, 444, 432, and 414 cm$^{-1}$, preferably it shows substantially the same data as an infrared absorption spectrum chart shown in FIG. 9.

The type B crystal of (2S)-2-amino-3-(3,4-bis((2-(benzoyloxy)-2-methylpropanoyl)oxy)phenyl)propanoic acid is characterized in that, for example, in an analysis by a melting point determination method, it has a melting point of from about 174.7° C. to 179.0° C.

Further, it has been confirmed that among the compounds of the present invention, for example, (2S)-2-amino-3-(3,4-bis((2-(benzoyloxy)-2-methylpropanoyl)oxy)phenyl)propanoic acid tosylate has at least two crystal forms (which are referred to as type A crystal and type B crystal in a distinguishable manner in the present description for the sake of convenience).

Figure 10:
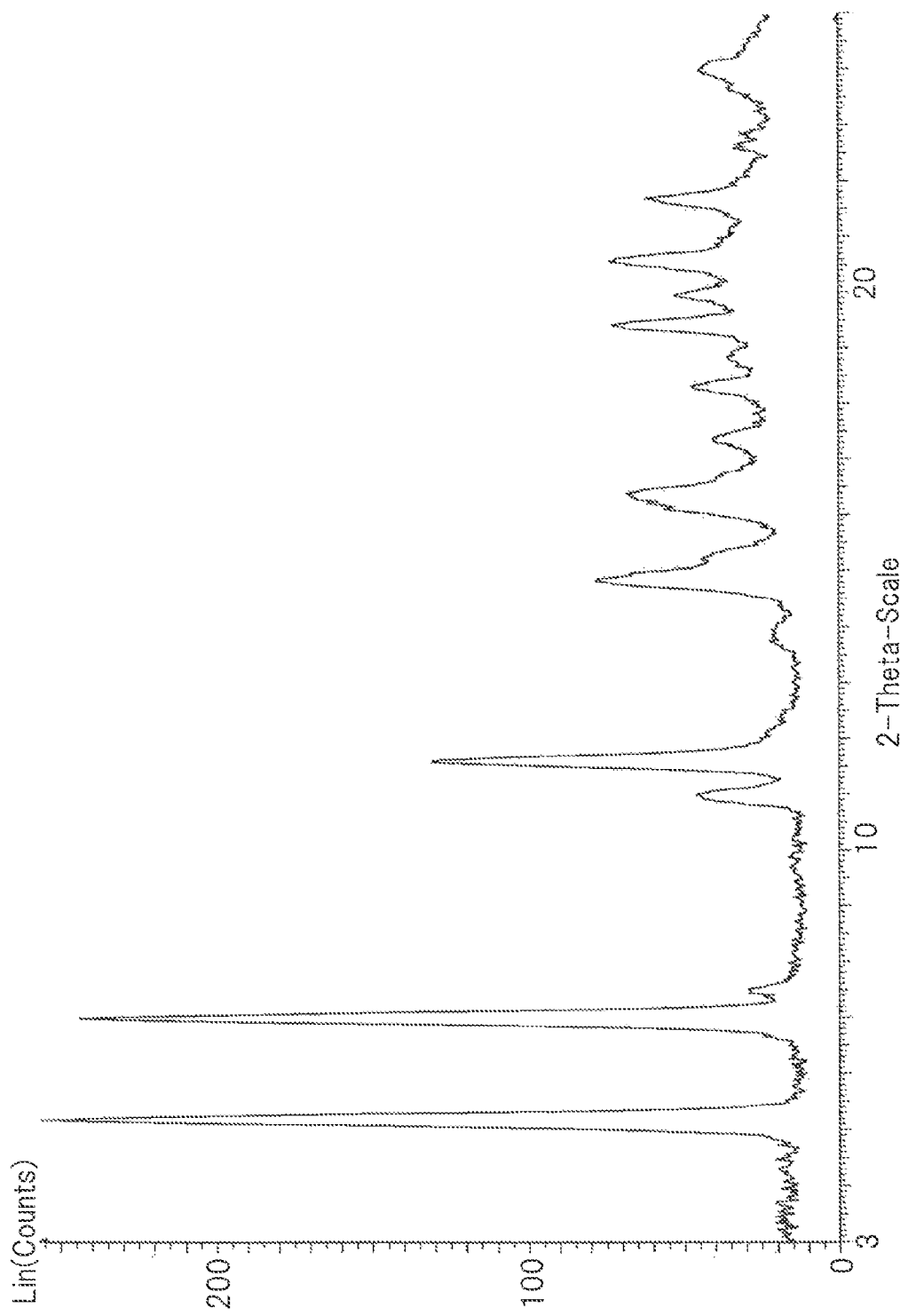
FIG. 10 shows a powder X-ray diffraction spectrum chart of crystalline (2S)-2-amino-3-(3,4-bis((2-(benzoyloxy)-2-methylpropanoyl)oxy)phenyl)propanoic acid tosylate (type A crystal) obtained in Example 6.

The type A crystal of (2S)-2-amino-3-(3,4-bis((2-(benzoyloxy)-2-methylpropanoyl)oxy)phenyl)propanoic acid tosylate is characterized in that, for example, in an analysis by powder X-ray diffraction spectrometry, it has at least peaks at 2θ of about 10.97, 11.58, 14.83, 16.36, 16.70, 19.42, 20.58, and 21.69 degrees, preferably it has peaks at 2θ of about 5.15, 6.97, 7.46, 10.97, 11.58, 13.74, 14.83, 15.20, 16.10, 16.36, 16.70, 17.35, 18.30, 18.83, 19.42, 19.95, 20.58, 21.69, 22.63, 22.84, and 24.00 degrees, more preferably it shows data shown in Table 1 in the below-described Example 6, particularly preferably it shows substantially the same data as a powder X-ray diffraction spectrum chart shown in FIG. 10.

Figure 11:
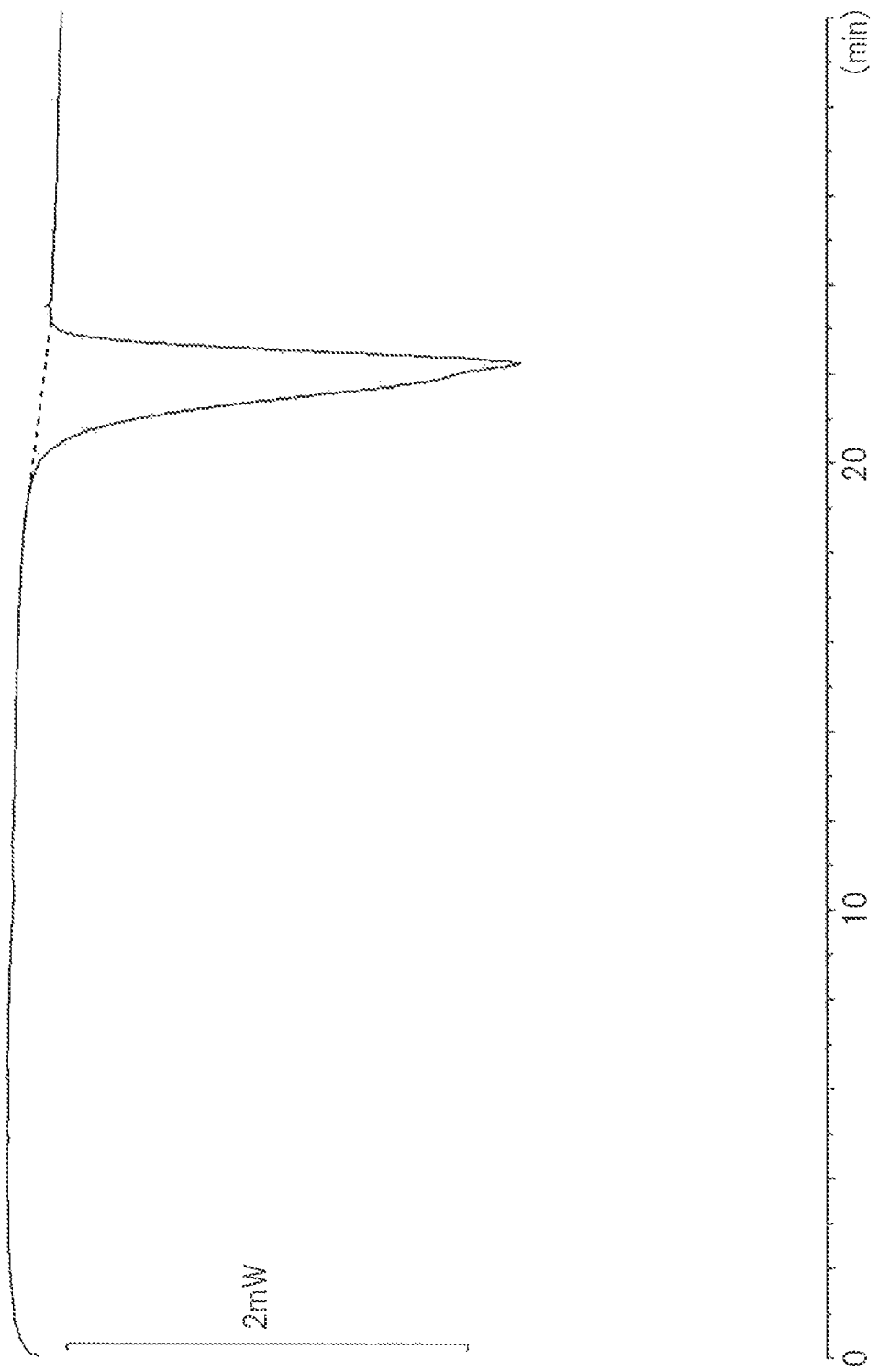
FIG. 11 shows a differential scanning calorimetry chart of crystalline (2S)-2-amino-3-(3,4-bis((2-(benzoyloxy)-2-methylpropanoyl)oxy)phenyl)propanoic acid tosylate (type A crystal) obtained in Example 6.

The type A crystal of (2S)-2-amino-3-(3,4-bis((2-(benzoyloxy)-2-methylpropanoyl)oxy)phenyl)propanoic acid tosylate is characterized in that, for example, in an analysis by differential scanning calorimetry, it has an endothermic peak at around 135.95° C., preferably it shows substantially the same data as a differential scanning calorimetry chart shown in FIG. 11.

Figure 12:
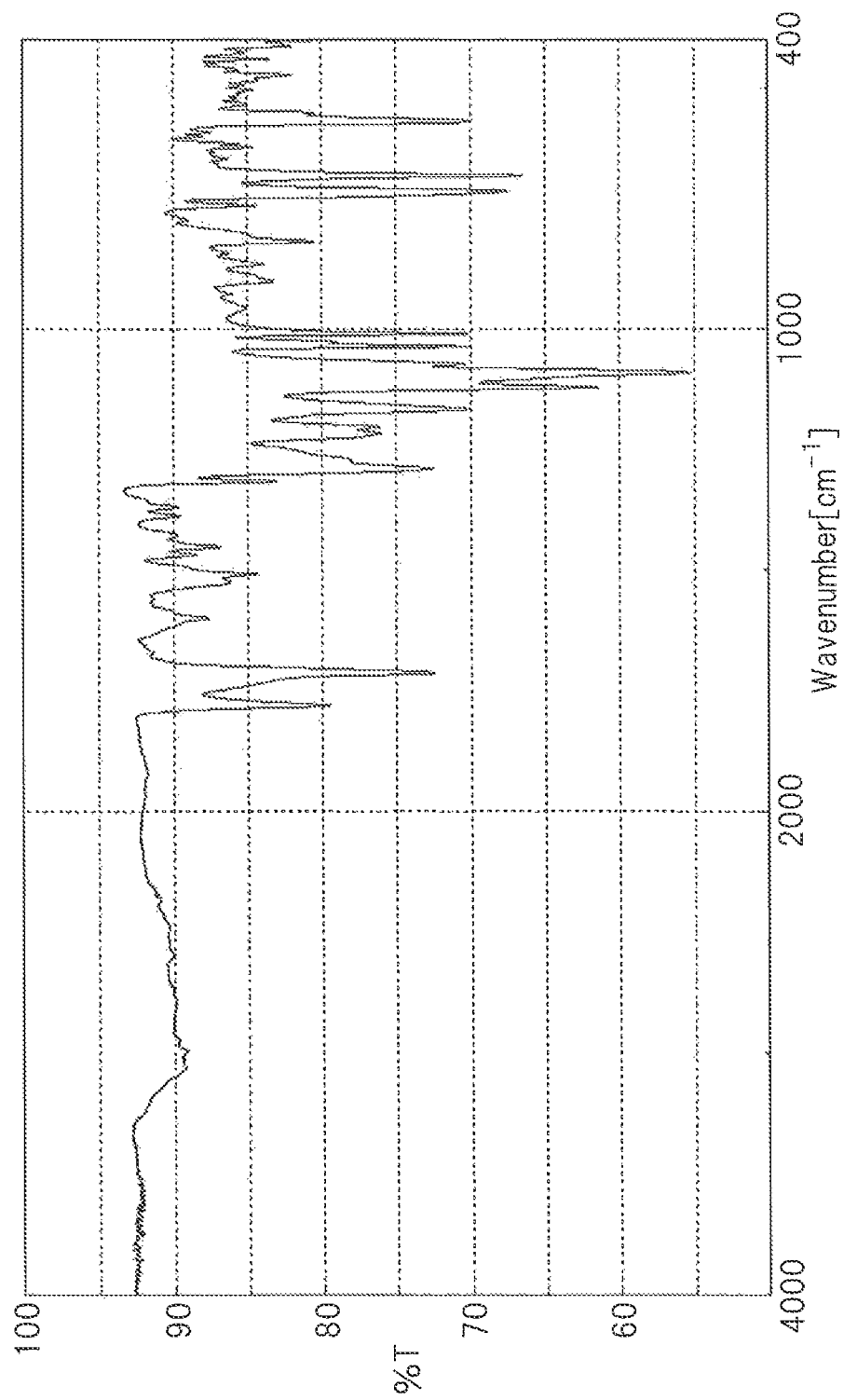
FIG. 12 shows an infrared absorption spectrum chart of crystalline (2S)-2-amino-3-(3,4-bis((2-(benzoyloxy)-2-methylpropanoyl)oxy)phenyl)propanoic acid tosylate (type A crystal) obtained in Example 6.

The type A crystal of (2S)-2-amino-3-(3,4-bis((2-(benzoyloxy)-2-methylpropanoyl)oxy)phenyl)propanoic acid tosylate is characterized in that, for example, in an analysis by infrared absorption spectrometry, it shows absorption at 1780, 1712, 1599, 1508, 1452, 1388, 1316, 1289, 1217, 1166, 1120, 1090, 1071, 1036, 1026, 1010, 957, 900, 864, 817, 742, 713, 680, 622, 567, 550, 472, and 440 cm$^{-1}$, preferably it shows substantially the same data as an infrared absorption spectrum chart shown in FIG. 12.

The type A crystal of (2S)-2-amino-3-(3,4-bis((2-(benzoyloxy)-2-methylpropanoyl)oxy)phenyl)propanoic acid tosylate is characterized in that, for example, in an analysis by a melting point determination method, it has a melting point of from about 132.0° C. to 136.0° C.

Figure 13:
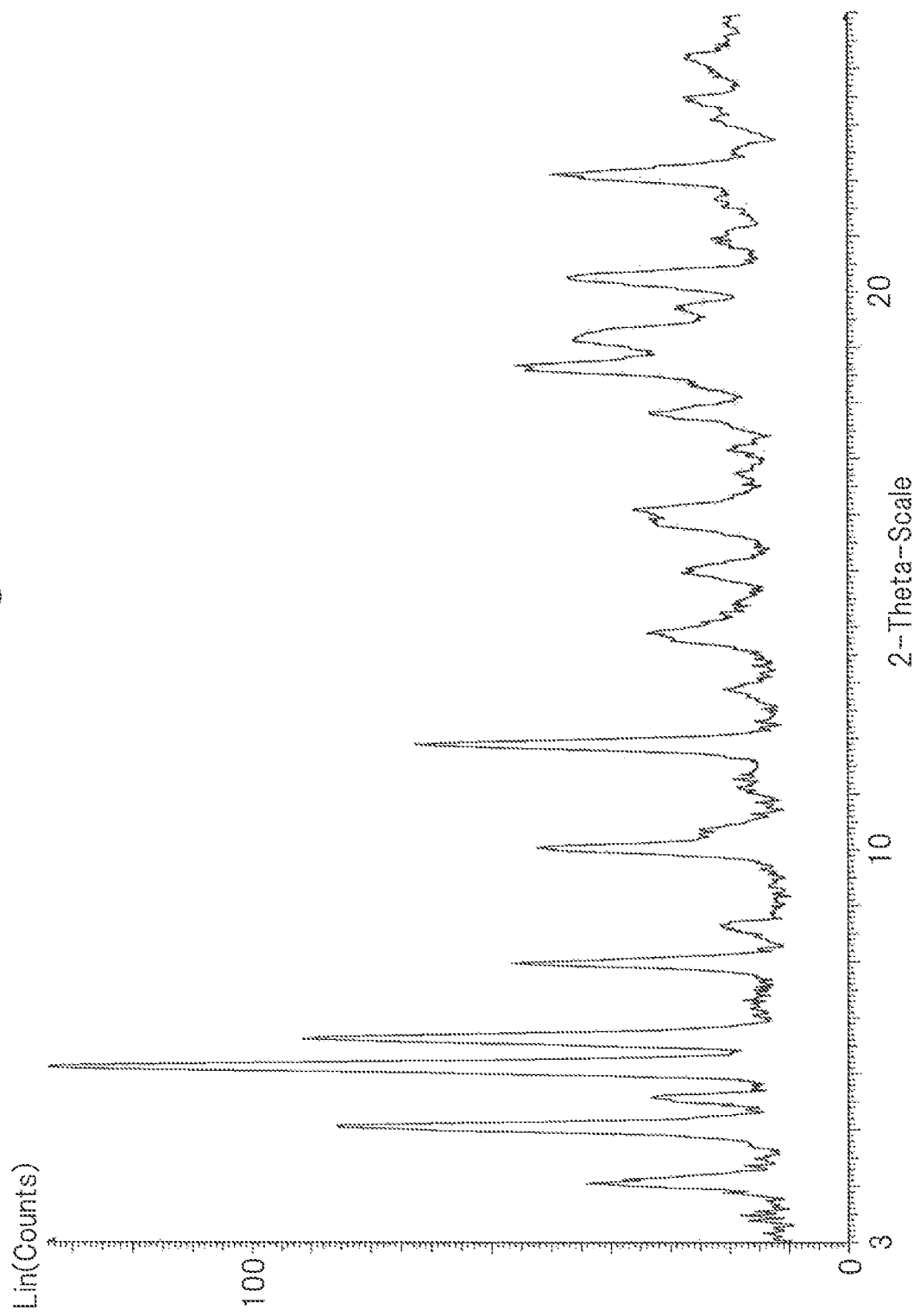
FIG. 13 shows a powder X-ray diffraction spectrum chart of crystalline (2S)-2-amino-3-(3,4-bis((2-(benzoyloxy)-2-methylpropanoyl)oxy)phenyl)propanoic acid tosylate (type B crystal) obtained in Example 7.

The type B crystal of (2S)-2-amino-3-(3,4-bis((2-(benzoyloxy)-2-methylpropanoyl)oxy)phenyl)propanoic acid tosylate is characterized in that, for example, in an analysis by powder X-ray diffraction spectrometry, it has at least peaks at 2θ of about 10.01, 11.88, 13.87, 15.01, 15.87, 16.07, 17.81, 18.65, 19.17, and 22.11 degrees, preferably it has peaks at 2θ of about 4.04, 5.04, 5.54, 6.11, 6.60, 7.96, 8.62, 10.01, 10.32, 11.88, 12.88, 13.87, 15.01, 15.87, 16.07, 16.74, 17.17, 17.81, 18.65, 19.17, 19.72, 20.27, 20.93, 21.67, 22.11, 22.56, 23.11, 23.47, and 24.21 degrees, more preferably it shows data shown in Table 2 in the below-described Example 7, particularly preferably it shows substantially the same data as a powder X-ray diffraction spectrum chart shown in FIG. 13.

Figure 14:
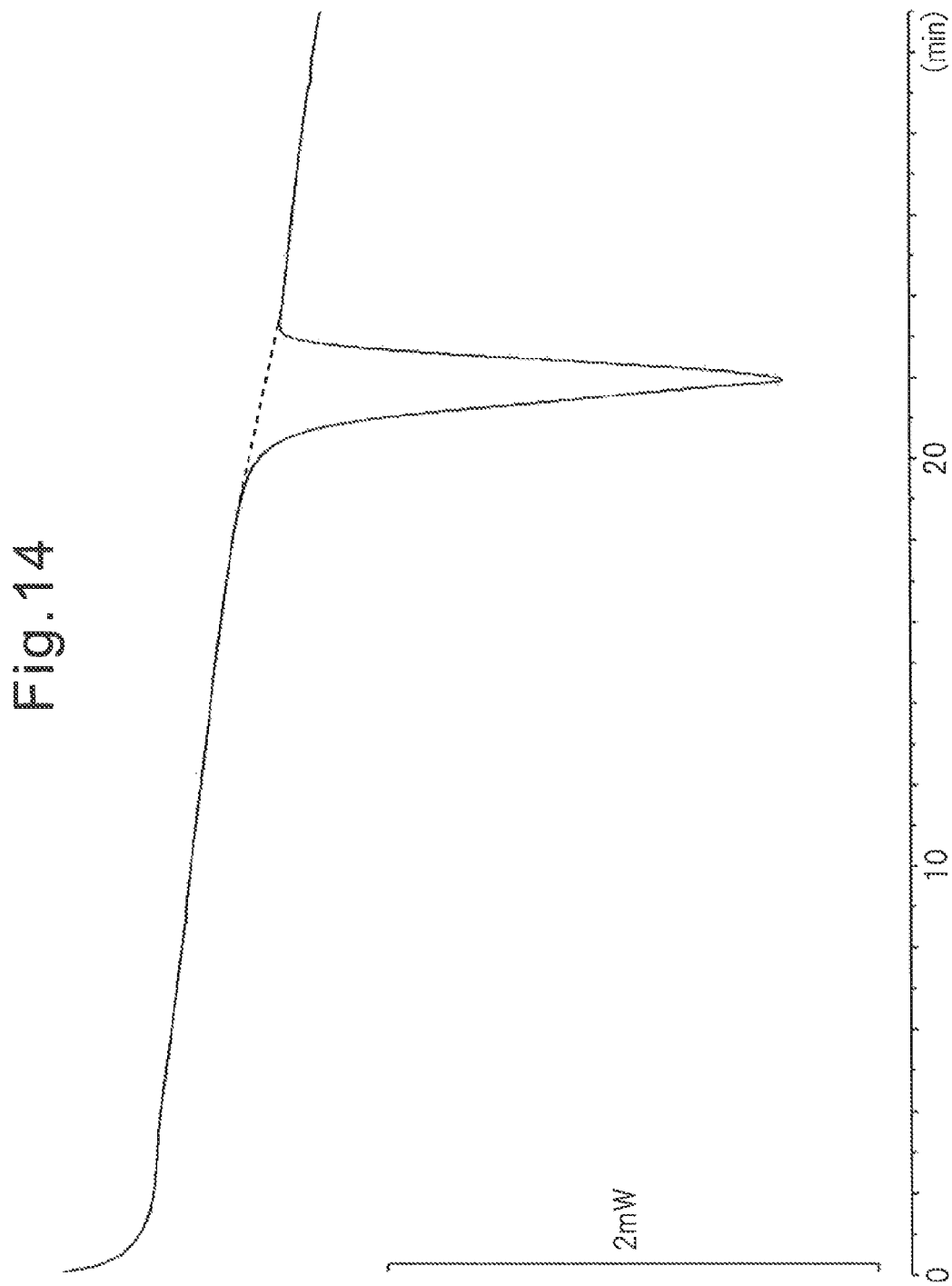
FIG. 14 shows a differential scanning calorimetry chart of crystalline (2S)-2-amino-3-(3,4-bis((2-(benzoyloxy)-2-methylpropanoyl)oxy)phenyl)propanoic acid tosylate (type B crystal) obtained in Example 7.

The type B crystal of (2S)-2-amino-3-(3,4-bis((2-(benzoyloxy)-2-methylpropanoyl)oxy)phenyl)propanoic acid tosylate is characterized in that, for example, in an analysis by differential scanning calorimetry, it has an endothermic peak at around 134.54° C., preferably it shows substantially the same data as a differential scanning calorimetry chart shown in FIG. 14.

Figure 15:
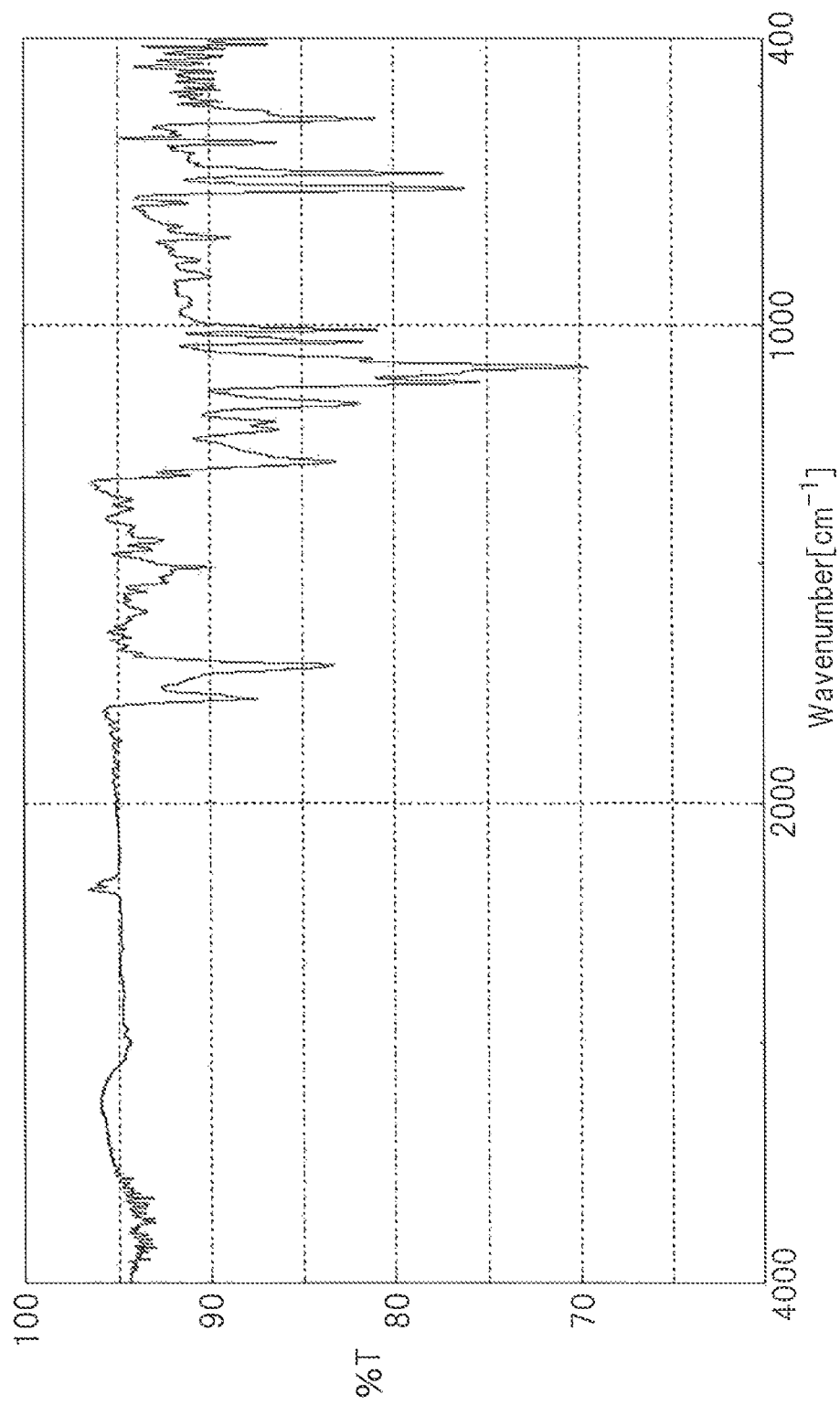
FIG. 15 shows an infrared absorption spectrum chart of crystalline (2S)-2-amino-3-(3,4-bis((2-(benzoyloxy)-2-methylpropanoyl)oxy)phenyl)propanoic acid tosylate (type B crystal) obtained in Example 7.

The type B crystal of (2S)-2-amino-3-(3,4-bis((2-(benzoyloxy)-2-methylpropanoyl)oxy)phenyl)propanoic acid tosylate is characterized in that, for example, in an analysis by infrared absorption spectrometry, it shows absorption at 1781, 1711, 1600, 1507, 1315, 1287, 1220, 1203, 1166, 1119, 1088, 1070, 1036, 1027, 1010, 944, 898, 863, 816, 713, 681, 617, 567, 531, 517, 507, 484, 470, 452, 437, 421, and 413 cm$^{-1}$, preferably it shows substantially the same data as an infrared absorption spectrum chart shown in FIG. 15.

The type B crystal of (2S)-2-amino-3-(3,4-bis((2-(benzoyloxy)-2-methylpropanoyl)oxy)phenyl)propanoic acid tosylate is characterized in that, for example, in an analysis by a melting point determination method, it has a melting point of from about 132.3° C. to 135.3° C.

Further, it has been confirmed that among the compounds of the present invention, for example, (2S)-2-amino-3-(3,4-bis((2-(benzoyloxy)-2-methylpropanoyl)oxy)phenyl)propanoic acid hydrochloride has an amorphous crystal form.

The amorphous (2S)-2-amino-3-(3,4-bis((2-(benzoyloxy)-2-methylpropanoyl)oxy)phenyl)propanoic acid hydrochloride is characterized in that, for example, in an analysis by powder X-ray diffraction spectrometry, no crystalline peaks are observed.

Figure 17:
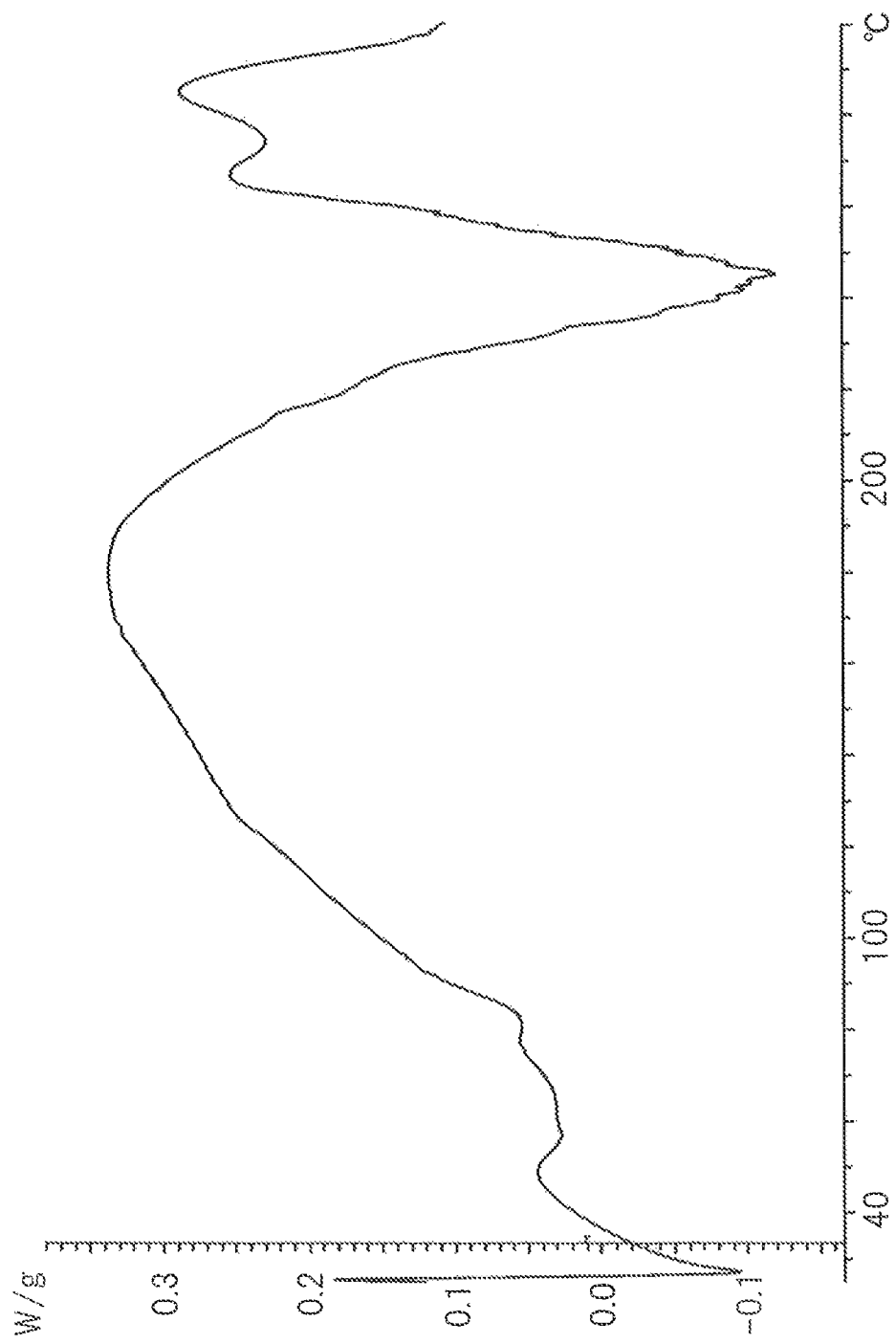
FIG. 17 shows a differential scanning calorimetry chart of amorphous (2S)-2-amino-3-(3,4-bis((2-(benzoyloxy)-2-methylpropanoyl)oxy)phenyl)propanoic acid hydrochloride obtained in Example 5.

The amorphous (2S)-2-amino-3-(3,4-bis((2-(benzoyloxy)-2-methylpropanoyl)oxy)phenyl)propanoic acid hydrochloride is characterized in that, for example, in an analysis by differential scanning calorimetry, it has an endothermic peak at around 82.83° C., preferably it shows substantially the same data as a differential scanning calorimetry chart shown in FIG. 17.

The amorphous (2S)-2-amino-3-(3,4-bis((2-(benzoyloxy)-2-methylpropanoyl)oxy)phenyl)propanoic acid hydrochloride is characterized in that, for example, in an analysis by infrared absorption spectrometry, it shows absorption at 3409, 2992, 2944, 2865, 2629, 1970, 1774, 1718, 1655, 1601, 1585, 1508, 1470, 1452, 1428, 1388, 1369, 1317, 1290, 1258, 1204, 1168, 1125, 1093, 1070, 1026, 1003, 958, 866, 806, 741, 714, 687, 617, 530, 496, 467, 447, and 419 cm$^{-1}$, preferably it shows substantially the same data as an infrared absorption spectrum chart shown in FIG. 18.

The amorphous (2S)-2-amino-3-(3,4-bis((2-(benzoyloxy)-2-methylpropanoyl)oxy)phenyl)propanoic acid hydrochloride is characterized in that, for example, in an analysis by a melting point determination method, it has a melting point of from about 112.0° C. to 117.0° C.

The crystal form of the compound of the present invention is specified by physicochemical properties disclosed in the present description, however, the respective data can slightly vary due to the nature thereof, and therefore, should not be strictly interpreted.

For example, the data obtained by powder X-ray diffraction spectrometry, for example, the relative intensity can slightly vary depending on the direction of crystal growth, the grain size, the measurement condition, etc. due to the nature thereof, and therefore, a diffraction angle (2θ) or an overall pattern is important for the determination of the identification of crystal forms. Further, in the determination of the identification of crystal forms, if necessary, a half-width is read from a powder X-ray diffraction spectrum chart, and may be used in combination with a diffraction angle (2θ), an overall pattern, or a relative intensity.

Further, the data obtained by differential scanning calorimetry or infrared absorption spectrometry can slightly vary depending on the measurement condition, etc. due to the nature thereof, and therefore, an overall pattern is important for the determination of the identification of crystal forms.

Therefore, compounds showing an overall pattern of at least one data obtained by powder X-ray diffraction spectrometry, differential scanning calorimetry, and infrared absorption spectrometry similar to that of the crystal form of the compound of the present invention disclosed in the present description are all included in the present invention.

Incidentally, although it can be easily understood by those skilled in the art, in the below-described drawings in the present description, in the powder X-ray diffraction spectrum chart, a diffraction angle (2θ) (degrees) is indicated on the horizontal axis (2-theta-scale), and a diffraction intensity is indicated on the vertical axis (Lin (counts)); in the differential scanning calorimetry chart, a time (min) or a temperature (° C.) is indicated on the horizontal axis, and a heat flux is indicated on the vertical axis; and in the infrared absorption spectrum chart, a wavelength is indicated on the horizontal axis (wavenumber [$cm^{-1}$]), and a transmittance is indicated on the vertical axis (% T).

The compound of the present invention is a levodopa prodrug and produces levodopa by being metabolized in vivo through, for example, all or some of the following (1) to (7) intermediates:
(1) (S)-2-amino-3-(3-((2-(benzoyloxy)-2-methylpropanoyl)oxy)-4-((2-hydroxy-2-methylpropanoyl)oxy)phenyl)propanoic acid;
(2) (S)-2-amino-3-(4-((2-(benzoyloxy)-2-methylpropanoyl)oxy)-3-((2-hydroxy-2-methylpropanoyl)oxy)phenyl)propanoic acid;
(3) (S)-2-amino-3-(3-((2-(benzoyloxy)-2-methylpropanoyl)oxy)-4-hydroxyphenyl)propanoic acid;
(4) (S)-2-amino-3-(3,4-bis((2-hydroxy-2-methylpropanoyl)oxy)phenyl)propanoic acid;
(5) (S)-2-amino-3-(4-((2-(benzoyloxy)-2-methylpropanoyl)oxy)-3-hydroxyphenyl)propanoic acid;
(6) (S)-2-amino-3-(4-hydroxy-3-((2-hydroxy-2-methylpropanoyl)oxy)phenyl)propanoic acid; and
(7) (S)-2-amino-3-(3-hydroxy-4-((2-hydroxy-2-methylpropanoyl)oxy)phenyl)propanoic acid.

As described above, the compound of the present invention is a prodrug capable of providing an effective blood concentration (an effective plasma concentration: 0.4 to 1 μg/mL) of levodopa for a long period of time in humans, and reduces the possibility of developing side effects such as dyskinesia or wearing-off as much as possible by providing a flat blood concentration-time profile of levodopa.

Although a description will be also given in the following Examples, such properties of the compound of the present invention are brought about by a combination of pharmacokinetic parameters of the compound of the present invention, for example, (1) an "area under the blood concentration-time curve (area under the curve (AUC))" calculated from a blood concentration-time profile of levodopa when the compound of the present invention is administered and (2) a "ratio (Cmax/C6 hr)" of a plasma concentration at 6 hours after oral administration (C6 hr) and a maximum plasma concentration Cmax)" calculated from a blood concentration-time profile of levodopa when the compound of the present invention is administered.

Here, (1) the "area under the blood concentration-time curve (area under the curve (AUC))" calculated from a blood concentration-time profile of levodopa when the compound of the present invention is administered can be used as an index of exposure to levodopa, and (2) the "ratio (Cmax/C6 hr) of a plasma concentration at 6 hours after oral administration (C6 hr) and a maximum plasma concentration (Cmax)" calculated from a blood concentration-time profile of levodopa when the compound of the present invention is administered can be used as an index indicating the "degree of flatness" of the blood concentration-time profile of levodopa.

In dogs in which the organ distribution of carboxyesterase is most similar to that of humans, in the case where the compound of the present invention is orally administered at a dose of, for example, 3 mg/kg expressed in terms of levodopa, the compound of the present invention shows an AUC described in the above (1) of, for example, 0.6 μg·hr/mL or more, preferably 0.7 μg·hr/mL or more, more preferably 0.8 μg·hr/mL or more, particularly preferably 0.85 μg·hr/mL or more. The values serving as the upper limits of the respective ranges are the values of the AUC (as the value in Examples, 0.96 μg·hr/mL is disclosed) of levodopa when an equivalent amount of levodopa (here, 3 mg/kg) is orally administered.

Further, under the same condition, the compound of the present invention shows a Cmax/C6 hr described in the above (2) of, for example 100 or less, preferably 75 or less, more preferably 50 or less, further more preferably 20 or less, particularly preferably 10 or less.

The compound of the present invention can be a "prodrug capable of providing an effective blood concentration of levodopa for a long period of time" in humans by showing preferred values of AUC described in the above (1) and Cmax/C6 hr described in the above (2) in combination in a kinetic study in dogs, and can be "a prodrug that reduces the possibility of developing side effects such as dyskinesia or wearing-off as much as possible by providing a flat blood concentration-time profile of levodopa".

[Method for Producing Compound of the Present Invention]

The compound of the present invention can be produced according to a method shown in the below-described Examples. In addition, the compound of the present invention can also be produced according to a method shown below or a method similar thereto, however, the production method is not limited thereto.

The compound of the present invention can be produced using levodopa:

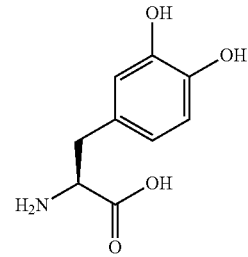

as a starting material according to the following procedure: (A) protection of the amino group→(B) protection of the carboxyl group→(C) acylation of the hydroxyl group→(D) deprotection of the protecting groups. Further, the order of the steps (A) and (B) may be reversed as needed.

(A) Protection of Amino Group

A protection reaction for the amino group is well known, and for example, (1) a method using an acid halide, (2) a method using a mixed acid anhydride, (3) a method using a condensing agent, etc. can be exemplified.

These methods will be specifically described below.

(1) The method using an acid halide is carried out, for example, as follows. A carboxylic acid is reacted with an acid halide agent (such as oxalyl chloride or thionyl chloride) in an organic solvent (such as chloroform, dichloromethane, diethyl ether, or tetrahydrofuran) or in the absence of any solvent at −20° C. to reflux temperature, and the obtained acid halide is reacted with an amine in the presence of a base (such as pyridine, triethylamine, dimethylaniline, dimethylaminopyridine, or diisopropylethylamine) in an organic solvent (such as chloroform, dichloromethane, diethyl ether, or tetrahydrofuran) at 0 to 40° C. Further, the method can also be carried out by reacting the obtained acid halide with an amine using an alkaline aqueous solution (such as an aqueous sodium bicarbonate solution or a sodium hydroxide solution) in an organic solvent (such as dioxane or tetrahydrofuran) at 0 to 40° C.

(2) The method using a mixed acid anhydride is carried out, for example, as follows. A carboxylic acid is reacted with an acid halide (such as pivaloyl chloride, tosyl chloride, or mesyl chloride), an acid derivative (such as ethyl chloroformate or isobutyl chloroformate), or an acid anhydride derivative (such as di-tert-butyl-dicarbonate) in an organic solvent (such as chloroform, dichloromethane, diethyl ether, or tetrahydrofuran) or in the absence of any solvent in the presence of a base (such as pyridine, triethylamine, dimethylaniline, dimethylaminopyridine, or diisopropylethylamine) at 0 to 40° C., and the obtained mixed acid anhydride is reacted with an amine in an organic solvent (such as chloroform, dichloromethane, diethyl ether, or tetrahydrofuran) at 0 to 40° C.

(3) The method using a condensing agent is carried out, for example, as follows. A carboxylic acid is reacted with an amine in an organic solvent (such as chloroform, dichloromethane, dimethyl formamide, diethyl ether, or tetrahydrofuran) or in the absence of any solvent in the presence or absence of a base (such as pyridine, triethylamine, dimethylaniline, or dimethylaminopyridine) using a condensing agent (such as 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, or 1-propanephosphonic acid cyclic anhydride (T3P)) and using or not using 1-hydroxybenztriazole (HOBt) at 0 to 40° C.

The reactions in these methods (1), (2), and (3) are preferably carried out in an inert gas (such as argon or nitrogen) atmosphere under an anhydrous condition.

Examples of the protecting group for the amino group include a benzyloxycarbonyl (Cbz) group, a tert-butoxycarbonyl (Boc) group, an aryloxycarbonyl (Alloc) group, a 1-methyl-1-(4-biphenyl)ethoxycarbonyl (Bpoc) group, a trifluoroacetyl group, a 9-fluorenylmethoxycarbonyl (Fmoc) group, a benzyl (Bn) group, a p-methoxybenzyl group, a benzyloxymethyl (BOM) group, a 2-(trimethylsilyl)ethoxymethyl (SEM) group, and the like.

(B) Protection of Carboxyl Group

A protection reaction for the carboxyl group is well known, and for example, (1) a method using an acid halide, (2) a method using a mixed acid anhydride, (3) a method using a condensing agent, etc. can be exemplified.

These methods will be specifically described below.

(1) The method using an acid halide is carried out, for example, as follows. A carboxylic acid is reacted with an acid halide agent (such as oxalyl chloride or thionyl chloride) in an organic solvent (such as chloroform, dichloromethane, diethyl ether, or tetrahydrofuran) or in the absence of any solvent at −20° C. to reflux temperature, and the obtained acid halide is reacted with an alcohol in the presence or absence of a base (such as pyridine, triethylamine, dimethylaniline, dimethylaminopyridine, or diisopropylethylamine) in an organic solvent (such as chloroform, dichloromethane, diethyl ether, or tetrahydrofuran) at 0° C. to the reflux temperature of the solvent used. Further, the method can also be carried out by reacting the acid halide using an alkaline aqueous solution (such as an aqueous sodium bicarbonate solution or a sodium hydroxide solution) in an organic solvent (such as dioxane or tetrahydrofuran) at 0 to 40° C.

(2) The method using a mixed acid anhydride is carried out, for example, as follows. A carboxylic acid is reacted with an acid halide (such as pivaloyl chloride, tosyl chloride, or mesyl chloride) or an acid derivative (such as ethyl chloroformate or isobutyl chloroformate) in an organic solvent (such as chloroform, dichloromethane, diethyl ether, or tetrahydrofuran) or in the absence of any solvent in the presence of a base (such as pyridine, triethylamine, dimethylaniline, dimethylaminopyridine, or diisopropylethylamine) at 0 to 40° C., and the obtained mixed acid anhydride is reacted with an alcohol in an organic solvent (such as chloroform, dichloromethane, diethyl ether, or tetrahydrofuran) at 0 to 40° C.

(3) The method using a condensing agent is carried out, for example, as follows. A carboxylic acid is reacted with an alcohol in an organic solvent (such as chloroform, dichloromethane, dimethyl formamide, diethyl ether, or tetrahydrofuran) or in the absence of any solvent in the presence or absence of a base (such as pyridine, triethylamine, dimethylaniline, or dimethylaminopyridine) using a condensing agent (such as 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, or 1-propanephosphonic acid cyclic anhydride (T3P)) and using or not using 1-hydroxybenztriazole (HOBt) at 0 to 40° C.

The reactions in these methods (1), (2), and (3) are preferably carried out in an inert gas (such as argon or nitrogen) atmosphere under an anhydrous condition.

Examples of the protecting group for the carboxyl group include methyl, ethyl, tert-butyl, trichloroethyl, benzyl (Bn), phenacyl, p-methoxybenzyl, trityl, 2-chlorotrityl, and the like.

(C) Acylation of Hydroxyl Group

The acylation of the hydroxyl group of a compound obtained by protecting the amino group and the carboxyl group of levodopa, that is, a compound represented by the formula:

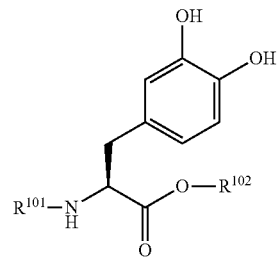

(wherein $R^{101}$ represents a protecting group for the amino group, and $R^{102}$ represents a protecting group for the carboxyl group) is carried out as follows. A carboxylic acid represented by the formula:

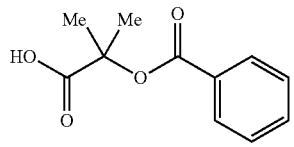 [SMILES: CC(C)(OC(=O)c1ccccc1)C(=O)O]

is reacted with an acid halide agent (such as oxalyl chloride or thionyl chloride) in an organic solvent (such as chloroform, dichloromethane, diethyl ether, or tetrahydrofuran) or in the absence of any solvent at −20° C. to reflux temperature, and the obtained acid halide is reacted with an alcohol in the presence of a base (such as pyridine, triethylamine, dimethylaniline, dimethylaminopyridine, or diisopropylethylamine) in an organic solvent (such as chloroform, dichloromethane, diethyl ether, tetrahydrofuran, or acetonitrile) at 0 to 40° C. Further, the method can also be carried out by reacting the acid halide using an alkaline aqueous solution (such as an aqueous sodium bicarbonate solution or a sodium hydroxide solution) in an organic solvent (such as dioxane or tetrahydrofuran) at 0 to 40° C.

(D) Deprotection of Protecting Groups

A deprotection reaction for the protecting groups represented by $R^{101}$ and $R^{102}$ is known, and can be carried out by the following method. Examples of the deprotection reaction include:

(1) a deprotection reaction by an alkali hydrolysis,
(2) a deprotection reaction in an acidic condition,
(3) a deprotection reaction by hydrogenolysis,
(4) a deprotection reaction for a silyl group,
(5) a deprotection reaction using a metal, and
(6) a deprotection reaction using a metal complex.

These methods will be specifically described below.

(1) A deprotection reaction by alkali hydrolysis is carried out, for example, in an organic solvent (such as methanol, tetrahydrofuran, or dioxane) using an alkali metal hydroxide (such as sodium hydroxide, potassium hydroxide, or lithium hydroxide), an alkaline earth metal hydroxide (such as barium hydroxide or calcium hydroxide), or a carbonate (such as sodium carbonate or potassium carbonate), or a solution thereof or a mixture thereof at 0 to 40° C.

(2) A deprotection reaction in an acidic condition is carried out, for example, in an organic solvent (such as dichloromethane, chloroform, dioxane, ethyl acetate, or anisole) and in an organic acid (such as acetic acid, trifluoroacetic acid, methanesulfonic acid, or p-toluenesulfonic acid) or an inorganic acid (such as hydrochloric acid or sulfuric acid) or a mixture thereof (such as a mixture of hydrogen bromide and acetic acid) at 0 to 100° C.

(3) A deprotection reaction by hydrogenolysis is carried out, for example, in a solvent (such as an ether-type solvent (such as tetrahydrofuran, dioxane, dimethoxyethane, or diethyl ether), an alcohol-type solvent (such as methanol or ethanol), a benzene-type solvent (such as benzene or toluene), a ketone-type solvent (such as acetone or methyl ethyl ketone), a nitrile-type solvent (such as acetonitrile), an amide-type solvent (such as dimethylformamide), water, ethyl acetate, acetic acid, or a mixed solvent of two or more of these solvents) in the presence of a catalyst (such as palladium-carbon, palladium black, palladium hydroxide, platinum oxide, or Raney nickel) under normal or increased pressure in a hydrogen atmosphere or in the presence of ammonium formate at 0 to 200° C.

(4) A deprotection reaction for a silyl group is carried out, for example, in an organic solvent miscible with water (such as tetrahydrofuran or acetonitrile) using tetrabutyl ammonium fluoride at 0 to 40° C.

(5) A deprotection reaction using a metal is carried out, for example, in an acidic solvent (such as acetic acid, a buffer with a pH of from 4.2 to 7.2, or a mixed liquid of such a solution and an organic solvent such as tetrahydrofuran) in the presence of zinc powder at 0 to 40° C., if necessary, by applying an ultrasonic wave.

(6) A deprotection reaction using a metal complex is carried out, for example, in an organic solvent (such as dichloromethane, dimethylformamide, tetrahydrofuran, ethyl acetate, acetonitrile, dioxane, or ethanol), water, or a mixed solvent thereof in the presence of a trap reagent (such as tributyltin hydride, triethylsilane, dimedone, morpholine, diethylamine, or pyrrolidine), an organic acid (such as acetic acid, formic acid, or 2-ethylhexanoic acid), and/or an organic acid salt (such as sodium 2-ethylhexanoate or potassium 2-ethylhexanoate) in the presence or absence of a phosphine reagent (such as triphenylphosphine) using a metal complex (such as tetrakistriphenylphosphine palladium(0), bis(triphenylphosphine)palladium(II)dichloride, palladium(II) acetate, or tris(triphenylphosphine)rhodium(I) chloride) at 0 to 40° C.

Further, the deprotection reaction can be carried out by a method other than the methods described above, for example, by a method described in Protective Groups in Organic Synthesis (written by T. W. Greene, John Wiley & Sons, Inc., 1999).

Although it can be easily understood by those skilled in the art, the target compound of the present invention can be easily produced by selecting a suitable deprotection reaction from the above deprotection reactions.

Incidentally, as described above, the compound of the present invention is not limited to the crystal form thereof. In other words, the compound of the present invention may be crystalline or amorphous, or may be a mixture of a crystalline compound and an amorphous compound at an arbitrary ratio.

As for several crystal forms of the compound of the present invention, detailed production methods therefor are disclosed in the below-described Examples, and the production thereof can be carried out according to the procedure. Further, such production can be carried out according to a method described below or a method similar thereto, however, the production method is not limited thereto.

For example, crystalline (2S)-2-amino-3-(3,4-bis((2-(benzoyloxy)-2-methylpropanoyl)oxy)phenyl)propanoic acid tosylate can be produced according to a method described below, a method similar thereto, or a method described in Examples.

More specifically, a type A crystal of (2S)-2-amino-3-(3,4-bis((2-(benzoyloxy)-2-methylpropanoyl)oxy)phenyl)propanoic acid tosylate can be produced by the reaction of either of the following Methods 1 and 2:

(Method 1) a method in which after (2S)-3-(3,4-bis((2-(benzoyloxy)-2-methylpropanoyl)oxy)phenyl)-2-((tert-butoxycarbonyl)amino)propanoic acid is subjected to a deprotection reaction using p-toluenesulfonic acid, a solvate of (2S)-2-amino-3-(3,4-bis((2-(benzoyloxy)-2-methylpropanoyl)oxy)phenyl)propanoic acid tosylate is produced without performing an isolation operation, followed by drying by heating under reduced pressure, whereby a type A crystal is produced; and (Method 2) a method in which after (2S)-3-(3,4-bis((2-(benzoyloxy)-2-methylpropanoyl)oxy)phenyl)-2-((tert-butoxycarbonyl)amino)propanoic acid is subjected to a deprotection reaction using p-toluenesulfonic acid, an amorphous compound is taken out from the reaction mixture, and then recrystallized, whereby a type A crystal is produced.

Hereinafter, the respective methods will be described in detail.

(Method 1)

Method 1 is a method in which after (2S)-3-(3,4-bis((2-(benzoyloxy)-2-methylpropanoyl)oxy)phenyl)-2-((tert-butoxycarbonyl)amino)propanoic acid is subjected to a deprotection reaction using p-toluenesulfonic acid, a solvate of (2S)-2-amino-3-(3,4-bis((2-(benzoyloxy)-2-methylpropanoyl)oxy)phenyl)propanoic acid tosylate is produced without performing an isolation operation, followed by drying by heating under reduced pressure, whereby a type A crystal is produced.

A deprotection reaction for a tert-butoxycarbonyl group using p-toluenesulfonic acid is known, and can be carried out, for example, in an organic solvent (such as acetonitrile, ethanol, ethyl acetate, tert-butylmethyl ether, n-heptane, isopropyl ether, or a mixed solvent of two or more of these solvents) or in a mixed solvent of such an organic solvent and water in the presence of 0.5 to 10 equivalents, preferably 0.5 to 3 equivalents, more preferably 0.5 to 1.5 equivalents of p-toluenesulfonic acid or a monohydrate thereof at 0° C. to the boiling point of the solvent used, preferably at 0 to 90° C.

Thereafter, a solvate obtained by subjecting the resulting mixture to slurry stirring at 0° C. to the boiling point of the solvent used, preferably at 0 to 90° C. without performing an isolation operation is dried by heating under reduced pressure at 30 to 100° C., preferably at 30 to 70° C., whereby a type A crystal can be produced.

Incidentally, as the solvent to be used in Method 1, a mixed solvent of acetonitrile and tert-butylmethyl ether, a mixed solvent of ethyl acetate and tert-butylmethyl ether, or a mixed solvent of acetonitrile and water is preferred.

(Method 2)

Method 2 is a method in which after (2S)-3-(3,4-bis((2-(benzoyloxy)-2-methylpropanoyl)oxy)phenyl)-2-((tert-butoxycarbonyl)amino)propanoic acid is subjected to a deprotection reaction using p-toluenesulfonic acid, an amorphous compound is taken out from the reaction mixture, and then recrystallized, whereby a type A crystal is produced.

The amorphous compound to be subjected to recrystallization can be prepared by concentrating the solvent used under reduced pressure after the deprotection reaction described above (in Method 1).

The obtained amorphous compound is recrystallized in an organic solvent (such as acetonitrile, ethanol, ethyl acetate, tert-butylmethyl ether, n-heptane, isopropyl ether, or a mixed solvent of two or more of these solvents) or in a mixed solvent of such an organic solvent and water, or the obtained amorphous compound is subjected to slurry stirring at 0° C. to the boiling point of the solvent used, preferably at 0 to 90° C., whereby a solvate is obtained. Then, the obtained solvate is dried by heating under reduced pressure at 30 to 100° C., preferably at 30 to 70° C., whereby a type A crystal can be produced.

Incidentally, as the solvent to be used for the deprotection reaction in Method 2, acetonitrile, ethyl acetate, a mixed solvent of acetonitrile and water, or a mixed solvent of ethyl acetate and water is preferred, and particularly a mixed solvent of acetonitrile and water is preferred. Further, the recrystallization operation is preferably carried out in a mixed solvent of ethyl acetate and tert-butylmethyl ether, a mixed solvent of acetonitrile and tert-butylmethyl ether, a mixed solvent of ethyl acetate and n-heptane, or a mixed solvent of ethanol and isopropyl ether, and particularly preferably carried out in a mixed solvent of acetonitrile and tert-butylmethyl ether.

On the other hand, a type B crystal of (2S)-2-amino-3-(3,4-bis((2-(benzoyloxy)-2-methylpropanoyl)oxy)phenyl)propanoic acid tosylate can be produced by the reaction of either of the following Methods 3 and 4:

(Method 3) a method in which after (2S)-3-(3,4-bis((2-(benzoyloxy)-2-methylpropanoyl)oxy)phenyl)-2-((tert-butoxycarbonyl)amino)propanoic acid is subjected to a deprotection reaction using p-toluenesulfonic acid, a solvate of (2S)-2-amino-3-(3,4-bis((2-(benzoyloxy)-2-methylpropanoyl)oxy)phenyl)propanoic acid tosylate is produced without performing an isolation operation, followed by drying by heating under reduced pressure, whereby a type B crystal is produced; and (Method 4) a method in which after a type A crystal is produced by the above-described Method 1 or 2, a solvate obtained by performing recrystallization or slurry stirring in an organic solvent (such as acetone) or in a mixed solvent of such an organic solvent and water is dried by heating under reduced pressure, whereby a type B crystal is produced.

Hereinafter, the respective methods will be described in detail.

(Method 3)

Method 3 is a method in which after (2S)-3-(3,4-bis((2-(benzoyloxy)-2-methylpropanoyl)oxy)phenyl)-2-((tert-butoxycarbonyl)amino)propanoic acid is subjected to a deprotection reaction using p-toluenesulfonic acid, a solvate of (2S)-2-amino-3-(3,4-bis((2-(benzoyloxy)-2-methylpropanoyl)oxy)phenyl)propanoic acid tosylate is produced without performing an isolation operation, followed by drying by heating under reduced pressure, whereby a type B crystal is produced.

A deprotection reaction for (2S)-3-(3,4-bis((2-(benzoyloxy)-2-methylpropanoyl)oxy)phenyl)-2-((tert-butoxycarbonyl)amino)propanoic acid is carried out in acetone or a mixed solvent of acetone and water in the presence of 0.5 to 10 equivalents, preferably 0.5 to 3 equivalents, more preferably 0.5 to 1.5 equivalents of p-toluenesulfonic acid or a monohydrate thereof at 0 to 60° C.

Thereafter, a solvate obtained by subjecting the resulting mixture to slurry stirring at 0 to 60° C. without performing an isolation operation is dried by heating under reduced pressure at 30 to 100° C., preferably at 30 to 70° C., whereby a type B crystal can be produced.

Incidentally, as the solvent to be used in Method 3, acetone is preferred.

(Method 4)

Method 4 is a method in which after a type A crystal is produced by the above-described Method 1 or 2, a solvate obtained by performing recrystallization or slurry stirring in an organic solvent (such as acetone) or in a mixed solvent of such an organic solvent and water is dried by heating under reduced pressure, whereby a type B crystal is produced.

A solvate obtained by suspending a type A crystal of (2S)-2-amino-3-(3,4-bis((2-(benzoyloxy)-2-methylpropanoyl)oxy)phenyl)propanoic acid tosylate produced by Method 1 or 2 in acetone or in a mixed solvent of acetone and water, and then, subjecting the resulting suspension to slurry stirring at 0 to 60° C. is dried by heating under reduced pressure at 25 to 100° C., preferably at 25 to 70° C., whereby a type B crystal can be produced.

Incidentally, as the solvent to be used in Method 4, acetone is preferred.

Further, crude (2S)-2-amino-3-(3,4-bis((2-(benzoyloxy)-2-methylpropanoyl)oxy)phenyl)propanoic acid can be produced according to a method described below, a method similar thereto, or a method described in Examples.

More specifically, the crude product can be produced by subjecting (2S)-2-amino-3-(3,4-bis((2-(benzoyloxy)-2-methylpropanoyl)oxy)phenyl)propanoic acid hydrochloride to the reaction of any of the following Methods 5 to 7 using an inorganic base, an organic base, or an organic epoxide compound:

(Method 5) a method in which (2S)-2-amino-3-(3,4-bis((2-(benzoyloxy)-2-methylpropanoyl)oxy)phenyl)propanoic acid hydrochloride is desalted with an inorganic base;

(Method 6) a method in which (2S)-2-amino-3-(3,4-bis((2-(benzoyloxy)-2-methylpropanoyl)oxy)phenyl)propanoic acid hydrochloride is desalted with an organic base; and (Method 7) a method in which (2S)-2-amino-3-(3,4-bis((2-(benzoyloxy)-2-methylpropanoyl)oxy)phenyl)propanoic acid hydrochloride is desalted with an organic epoxide compound, or subjecting (2S)-2-amino-3-(3,4-bis((2-(benzoyloxy)-2-methylpropanoyl)oxy)phenyl)propanoic acid tosylate to the reaction of either of the following Methods 8 and 9 using an inorganic base or an organic base:

(Method 8) a method in which (2S)-2-amino-3-(3,4-bis((2-(benzoyloxy)-2-methylpropanoyl)oxy)phenyl)propanoic acid tosylate is desalted with an inorganic base; and (Method 9) a method in which (2S)-2-amino-3-(3,4-bis((2-(benzoyloxy)-2-methylpropanoyl)oxy)phenyl)propanoic acid tosylate is desalted with an organic base.

Hereinafter, the respective methods will be described in detail.

(Method 5)

Method 5 is a method in which (2S)-2-amino-3-(3,4-bis((2-(benzoyloxy)-2-methylpropanoyl)oxy)phenyl)propanoic acid hydrochloride is desalted with an inorganic base. A desalting reaction for an amino acid hydrochloride with an inorganic base is known, and the desalting is carried out by, for example, performing the reaction in a solvent (such as acetonitrile, ethyl acetate, tetrahydrofuran, dioxane, methanol, ethanol, water, or a mixed solvent of two or more of these solvents) using 0.5 to 10 equivalents, preferably 0.5 to 3 equivalents, more preferably 0.5 to 1.5 equivalents of an inorganic base (such as sodium hydroxide, potassium hydroxide, or barium hydroxide) or an aqueous solution thereof at 0° C. to the boiling point of the solvent used, preferably at 0 to 40° C.

(Method 6)

Method 6 is a method in which (2S)-2-amino-3-(3,4-bis((2-(benzoyloxy)-2-methylpropanoyl)oxy)phenyl)propanoic acid hydrochloride is desalted with an organic base. A desalting reaction for an amino acid hydrochloride with an organic base is known, and the desalting is carried out by, for example, performing the reaction in a solvent (such as acetonitrile, ethyl acetate, tetrahydrofuran, dioxane, methanol, ethanol, water, or a mixed solvent of two or more of these solvents) using 0.5 to 10 equivalents, preferably 0.5 to 3 equivalents, more preferably 0.5 to 1.5 equivalents of an organic base (such as triethylamine, diisopropylethylamine, or N-methylpiperidine) at 0° C. to the boiling point of the solvent used, preferably at 0 to 40° C.

(Method 7)

Method 7 is a method in which (2S)-2-amino-3-(3,4-bis((2-(benzoyloxy)-2-methylpropanoyl)oxy)phenyl)propanoic acid hydrochloride is desalted with an organic epoxide compound. A desalting reaction for an amino acid hydrochloride with an organic epoxide compound is known, and the desalting is carried out by, for example, performing the reaction in a solvent (such as acetonitrile, ethyl acetate, tetrahydrofuran, dioxane, methanol, ethanol, water, or a mixed solvent of two or more of these solvents) using 0.5 to 10 equivalents of an organic epoxide compound (such as epichlorohydrin, ethylene oxide, or styrene oxide) at 0° C. to the boiling point of the solvent used, preferably at 0 to 60° C.

(Method 8)

Method 8 is a method in which (2S)-2-amino-3-(3,4-bis((2-(benzoyloxy)-2-methylpropanoyl)oxy)phenyl)propanoic acid tosylate is desalted with an inorganic base. Here, (2S)-2-amino-3-(3,4-bis((2-(benzoyloxy)-2-methylpropanoyl)oxy)phenyl)propanoic acid tosylate to be used as a starting material may be crystalline or amorphous, or may be a mixture of a crystalline compound and an amorphous compound at an arbitrary ratio. A desalting reaction for an amino acid tosylate with an inorganic base is known, and the desalting is carried out by, for example, performing the reaction in a solvent (such as acetonitrile, ethyl acetate, tetrahydrofuran, dioxane, methanol, ethanol, water, or a mixed solvent of two or more of these solvents) using 0.5 to 10 equivalents, preferably 0.5 to 3 equivalents, more preferably 0.5 to 1.5 equivalents of an inorganic base (such as sodium hydroxide, potassium hydroxide, or barium hydroxide) or an aqueous solution thereof at 0° C. to the boiling point of the solvent used, preferably at 0 to 40° C.

(Method 9)

Method 9 is a method in which (2S)-2-amino-3-(3,4-bis((2-(benzoyloxy)-2-methylpropanoyl)oxy)phenyl)propanoic acid tosylate is desalted with an organic base. Here, (2S)-2-amino-3-(3,4-bis((2-(benzoyloxy)-2-methylpropanoyl)oxy)phenyl)propanoic acid tosylate to be used as a starting material may be crystalline or amorphous, or may be a mixture of a crystalline compound and an amorphous compound at an arbitrary ratio. A desalting reaction for an amino acid tosylate with an organic base is known, and the desalting is carried out by, for example, performing the reaction in a solvent (such as acetonitrile, ethyl acetate, tetrahydrofuran, dioxane, methanol, ethanol, water, or a mixed solvent of two or more of these solvents) using 0.5 to 10 equivalents, preferably 0.5 to 3 equivalents, more preferably 0.5 to 1.5 equivalents of an organic base (such as triethylamine, diisopropylethylamine, or N-methylpiperidine) at 0° C. to the boiling point of the solvent used, preferably at 0 to 40° C.

Then, crystalline (2S)-2-amino-3-(3,4-bis((2-(benzoyloxy)-2-methylpropanoyl)oxy)phenyl)propanoic acid can be produced according to a method described below, a method similar thereto, or a method described in Examples.

More specifically, a type A crystal of (2S)-2-amino-3-(3,4-bis((2-(benzoyloxy)-2-methylpropanoyl)oxy)phenyl)propanoic acid can be produced by the reaction of either of the following Methods 10 and 11:

(Method 10) a method in which after crude (2S)-2-amino-3-(3,4-bis((2-(benzoyloxy)-2-methylpropanoyl)oxy)phenyl)propanoic acid is produced by any of the above-described Methods 5 to 9, a type A crystal is produced without isolating the crude product; and (Method 11) a method in which after crude (2S)-2-amino-3-(3,4-bis((2-(benzoyloxy)-2-methylpropanoyl)oxy)phenyl)propanoic acid is produced by any of the above-described Methods 5 to 9, the crude product is isolated and converted into a type A crystal.

Hereinafter, the respective methods will be described in detail.

(Method 10)

Method 10 is a method in which after crude (2S)-2-amino-3-(3,4-bis((2-(benzoyloxy)-2-methylpropanoyl)oxy)phenyl)propanoic acid is produced by any of the above-described Methods 5 to 9, a type A crystal is produced without isolating the crude product.

A crude product produced by any of the above-described Methods 5 to 9, preferably Method 7 or 9 is subjected to slurry stirring in a solvent used in the desalting reaction (such as acetonitrile) at 0 to 80° C., preferably 0 to 50° C., more preferably 0 to 30° C., followed by drying by heating under reduced pressure at 25 to 100° C., preferably 25 to 70° C., whereby a type A crystal can be produced.

Incidentally, as the solvent to be used in Method 10, acetonitrile is preferred.

(Method 11)

Method 11 is a method in which after crude (2S)-2-amino-3-(3,4-bis((2-(benzoyloxy)-2-methylpropanoyl)oxy)phenyl)propanoic acid is produced by any of the above-described Methods 5 to 9, the crude product is isolated and converted into a type A crystal.

A crude product produced by any of the above-described Methods 5 to 9 is isolated, and then suspended in an organic solvent (such as acetonitrile). Subsequently, the resulting suspension is subjected to slurry stirring at 0 to 80° C., preferably 0 to 50° C., more preferably 0 to 30° C., followed by drying by heating under reduced pressure at 25 to 100° C., preferably 25 to 70° C., whereby a type A crystal can be produced.

Incidentally, as the solvent to be used in Method 11, acetonitrile is preferred.

On the other hand, a type B crystal of (2S)-2-amino-3-(3,4-bis((2-(benzoyloxy)-2-methylpropanoyl)oxy)phenyl)propanoic acid can be produced by the reaction of either of the following Methods 12 and 13:

(Method 12) a method in which after crude (2S)-2-amino-3-(3,4-bis((2-(benzoyloxy)-2-methylpropanoyl)oxy)phenyl)propanoic acid is produced by any of the above-described Methods 5 to 9, a type B crystal is produced without isolating the crude product; and (Method 13) a method in which after crude (2S)-2-amino-3-(3,4-bis((2-(benzoyloxy)-2-methylpropanoyl)oxy)phenyl)propanoic acid is produced by any of the above-described Methods 5 to 9, the crude product is isolated and converted into a type B crystal.

Hereinafter, the respective methods will be described in detail.

(Method 12)

Method 12 is a method in which after crude (2S)-2-amino-3-(3,4-bis((2-(benzoyloxy)-2-methylpropanoyl)oxy)phenyl)propanoic acid is produced by any of the above-described Methods 5 to 9, a type B crystal is produced without isolating the crude product.

A crude product produced by any of the above-described Methods 5 to 9 is subjected to stirring in a mixed solvent of a solvent used in the desalting reaction (such as acetonitrile) and water at a ratio of from 100:1 to 100:50, preferably from 100:1 to 100:10, more preferably from 100:5 to 100:10 at 0 to 80° C., preferably 0 to 60° C., followed by recrystallization by adding an organic solvent (such as acetonitrile) thereto. The resulting crystal is then dried by heating under reduced pressure at 25 to 100° C., preferably 25 to 70° C., whereby a type B crystal can be produced.

Incidentally, as the solvent to be used in Method 12, acetonitrile is preferred.

(Method 13)

Method 13 is a method in which after crude (2S)-2-amino-3-(3,4-bis((2-(benzoyloxy)-2-methylpropanoyl)oxy)phenyl)propanoic acid is produced by any of the above-described Methods 5 to 9, the crude product is isolated and converted into a type B crystal.

A crude product produced by any of the above-described Methods 5 to 9 is isolated, and then dissolved in a mixed solvent of an organic solvent and water at a ratio of from 100:1 to 100:50, preferably from 100:1 to 100:10, more preferably from 100:5 to 100:10, and the resulting solution is stirred at 0 to 80° C., preferably 0 to 60° C., followed by recrystallization by adding an organic solvent (such as acetonitrile) thereto. The resulting crystal is then dried by heating under reduced pressure at 25 to 100° C., preferably 25 to 70° C., whereby a type B crystal can be produced.

Incidentally, as the solvent to be used in Method 13, acetonitrile is preferred.

It is also possible to mutually convert the type A crystal and the type B crystal of (2S)-2-amino-3-(3,4-bis((2-(benzoyloxy)-2-methylpropanoyl)oxy)phenyl)propanoic acid to each other. That is, by subjecting the type A crystal to the reaction of the above-described Method 12 or 13, the type B crystal can be obtained. Meanwhile, by subjecting the type B crystal to the reaction of the above-described Method 10 or 11, the type A crystal can be obtained.

The compound of the present invention can be produced by a known method other than the methods described above, for example, by using a method described in Comprehensive Organic Transformations: A Guide to Functional Group Preparations 2nd Edition (Richard C. Larock, John Wiley & Sons. Inc, 1999) or the like, or a partial modification of a known method, etc. in combination.

In each reaction in the present description, the compound used as the starting material is known per se, or can be easily produced by a known method.

In each reaction in the present description, the reaction with heating can be carried out, as is appreciated by those skilled in the art, by using a water bath, an oil bath, a sand bath, or a microwave.

In each reaction described in the present description, a solid-phase supported reagent supported on a high-molecular polymer (such as polystyrene, polyacrylamide, polypropylene, or polyethylene glycol) may be used as needed.

In each reaction described in the present description, the reaction product can be purified by a common purification method such as distillation under normal or reduced pressure, high-performance liquid chromatography using a silica gel or magnesium silicate, thin-layer chromatography, an ion-exchange resin, a scavenger resin or column chromatography, or washing or recrystallization. Purification may be carried out after each reaction or after a few reactions.

[Toxicity]

The compound of the present invention has low toxicity, and therefore can be used safely as a pharmaceutical product. In particular, since the compound of the present invention does not have mutagenicity, even in the case where a drug has to be taken over a period as long as several years or several decades such as Parkinson's disease and/or Parkinson's syndrome, patients can continue to take the drug without worrying.

[Application to Pharmaceutical Product]

The compound of the present invention is useful for prevention and/or treatment of Parkinson's disease and/or Parkinson's syndrome. Here, the prevention and/or treatment of Parkinson's disease and/or Parkinson's syndrome literally refers to prevention or treatment of Parkinson's disease or Parkinson's syndrome, and also includes, for example, prevention of the development of dyskinesia, reduction of the severity of dyskinesia, inhibition of the progression of the symptoms of Parkinson's disease or Parkinson's syndrome (protective effect on dopamine newron), and prevention and/or treatment of non-motor symptoms of Parkinson's disease or Parkinson's syndrome (such as sleep disorders (such as sleep-onset insomnia, frequent nocturnal awakening, REM sleep behavior disorder, sleep-disordered breathing, sleep arousal disorder, delayed sleep phase syndrome, sleep terror, nocturia, sleep paralysis, and sleep-related eating disorder), psychiatric symptoms (such as depressive symptoms, anxiety, apathy, anhedonia, visual hallucination, delusion, impulse control disorder, and dopamine dysregulation), autonomic nervous symptoms (such as gastrointestinal symptoms (such as nausea, constipation, and drooling), orthostatic hypotension, postprandial hypotension, hyperhidrosis, oily skin, urination disorders, and erectile dysfunction), cognitive impairments, fatigue, sexual dysfunction, numbness, and pain). Further, the compound of the present invention is a levodopa prodrug, and therefore is also useful for prevention and/or treatment of other diseases, for which levodopa is used as a therapeutic agent, or against which levodopa is expected to have an effect, such as Lewy body disease, depression, attention deficit disorder, schizophrenia, manic-depressive illness, cognitive impairments, RLS (restless legs syndrome), periodic limb movement disorder, tardive dyskinesia, Huntington's disease, Tourette's syndrome, hypertension, addiction disorder, congestive heart failure, pain accompanying diabetic neuropathy, postherpetic neuralgia, fibromyalgia, autism, drug dependence, disease such as narcolepsy or excessive daytime sleepiness, dopa-responsive dystonia, vegetative state, Perry syndrome, Segawa's disease, malignant syndrome, ejaculation disorder, gastroparesis, Lesch-Nyhan disease, amblyopia, pulmonary hypertension, corticobasal degeneration, phenylketonuria, panic attack, decreased libido, swallowing reflex disorder, and multiple system atrophy.

The Lewy body disease may be any disease as long as it is a disease in which Lewy bodies are pathologically observed, and for example, Lewy body dementia, etc. are included.

Further, the compound of the present invention is also useful for prevention and/or treatment of a disease which is expected to be improved by dopamine stimulation and a disease which is induced by a decrease in noradrenaline other than the diseases described above.

Here, examples of the disease which is expected to be improved by dopamine stimulation include hyperkinetic child syndrome, toxemia of pregnancy, malignant hypertension, and epilepsy.

Further, examples of the disease which is induced by a decrease in noradrenaline include orthostatic hypotension, subarachnoid hemorrhage, cerebral infarction, bronchospasm accompanying bronchial asthma, whooping cough, or the like, hypoglycemic symptoms due to insulin injection, and iris adhesion in iridocyclitis.

The compound of the present invention may be used in combination with, for example, a drug which is used for prevention and/or treatment of Parkinson's disease and/or Parkinson's syndrome for the purpose of, for example, (1) complementation and/or enhancement of the preventive, therapeutic, and/or symptom improving effect thereof, (2) improvement of the kinetics and absorption thereof and reduction of the dose thereof, and/or (3) reduction of side effects thereof. Examples of the drug to be used in combination include levodopa or an analog thereof, an aromatic L-amino acid decarboxylase inhibitor, a catechol-O-methyltransferase inhibitor, a combination preparation for dopamine replacement therapy containing such agents in combination, a dopamine receptor agonist, a dopamine releaser, a monoamine oxidase (MAO) inhibitor, a dopamine uptake inhibitor, an anticholinergic agent, a nicotinic acetylcholine receptor agonist, a noradrenaline receptor agonist, an α2 receptor antagonist, a serotonin receptor agonist, a 5-HT1A selective agonist/D2 receptor antagonist, an adenosine receptor (A2A) antagonist, an NMDA receptor antagonist, a cannabinoid receptor (CB1) agonist, an AMPA receptor antagonist, a glutamate release inhibitor, an antihistamine agent, an antiepileptic agent, an antidepressant, a stimulant drug, a mixed lineage kinase inhibitor, an estrogen analog, an antipsychotic drug, a neurotrophic factor, a neuroprotective drug, an immunophilin ligand, a gene therapeutic agent, a cell-based therapeutic agent, and a botulinum toxin.

Here, examples of levodopa or an analog thereof include levodopa, melevodopa, etilevodopa, and the like.

Examples of the aromatic L-amino acid decarboxylase inhibitor include benserazide, benserazide hydrochloride, carbidopa, carbidopa hydrate, and the like.

Examples of the catechol-O-methyltransferase inhibitor include entacapone, tolcapone, nitecapone, BIA-3-202, CGP-28014, and the like.

Examples of the combination preparation for dopamine replacement therapy containing such agents in combination include a levodopa/benserazide combination preparation, a levodopa/carbidopa combination preparation, a levodopa/carbidopa/entacapone combination preparation, a melevodopa/carbidopa combination preparation, and the like.

Examples of the dopamine receptor agonist include cabergoline, pergolide, pergolide mesylate, bromocryptine, bromocryptine mesylate, pramipexole, pramipexole hydrochloride hydrate, ropinirole, ropinirole hydrochloride, talipexole, α-dihydroergocryptine, apomorphine, apomorphine hydrochloride, sumanirole, terguride, bifeprunox, piribedil, lisuride, lisuride maleate, rotigotine, DAR-0100, SLV-308, and the like.

Examples of the dopamine releaser include amantadine, amantadine hydrochloride, budipine, and the like.

Examples of the monoamine oxidase (MAO) inhibitor include selegiline, safinamide, safrazine, deprenil, mofegiline, rasagiline, rasagiline mesylate, lazabemide, lazabemide hydrochloride, and the like.

Examples of the dopamine uptake inhibitor include modafinil, NS-2330, and the like.

Examples of the anticholinergic agent include trihexyphenidyl, trihexyphenidyl hydrochloride, biperiden, profenamine, metixene, metixene hydrochloride, piroheptine, piroheptine hydrochloride, mazaticol, mazaticol hydrochloride, and the like.

Examples of the nicotinic acetylcholine receptor agonist include altinicline, altinicline maleate, and the like.

Examples of the noradrenaline receptor agonist include droxidopa and the like.

Examples of the α2 receptor antagonist include fipamezole and the like.

Examples of the serotonin receptor agonist include ACP-103 and the like.

Examples of the 5-HT1A selective agonist/D2 receptor antagonist include sarizotan, sarizotan hydrochloride, and the like.

Examples of the adenosine receptor (A2A) antagonist include istradefylline, Sch-63390, VR-2006, and the like.

Examples of the NMDA receptor antagonist include remacemide, remacemide hydrochloride, and the like.

Examples of the cannabinoid receptor (CB1) agonist include AVE-1625 and the like.

Examples of the AMPA receptor antagonist include talampanel, E-2007, and the like.

Examples of the glutamate release inhibitor include riluzole and the like.

Examples of the antihistamine agent include promethazine and the like.

Examples of the antiepileptic agent include zonisamide and the like.

Examples of the antidepressant include nortriptyline, imipramine, amitriptyline, clomipramine, desipramine, maprotiline, mianserin, setiptiline, fluoxetine, fluvoxamine, sertraline, paroxetine, mirtazapine, duloxetine, and the like.

Examples of the stimulant drug include methylphenidate and the like.

Examples of the mixed lineage kinase inhibitor include CEP-1347 and the like.

Examples of the estrogen analog include MITO-4509 and the like.

Examples of the antipsychotic drug include clozapine, quetiapine, quetiapine fumarate, olanzapine, risperidone, tiapride, aripiprazole, and the like.

Examples of the neurotrophic factor include GDNF, PYM-50028, SR-57667, leteprinim potassium, and the like. Examples of the neuroprotective drug include TCH-346 and the like.

Examples of the immunophilin ligand include GPI-1485 and the like.

Examples of the gene therapeutic agent include CERE-120, NLX-XI, P63, and the like.

Examples of the cell-based therapeutic agent include spheramine and the like.

In particular, when the compound of the present invention is administered, by administering the compound of the present invention in combination with carbidopa, carbidopa hydrate, benserazide, or benserazide hydrochloride, each of which is an aromatic L-amino acid decarboxylase inhibitor, and/or entacapone, tolcapone, nitecapone, BIA-3-202, or CGP-28014, each of which is a catechol-O-methyltransferase inhibitor, the sustained blood concentration-time profile of levodopa brought about by the compound of the present invention is further prolonged. Therefore, it becomes possible to maintain the blood concentration of levodopa in a range of from 0.1 to 1.5 μg/mL, preferably from 0.2 to 1.4 μg/mL, more preferably from 0.3 to 1.2 μg/mL, and particularly preferably in a range of from 0.4 to 1 μg/mL, which is regarded as an effective blood concentration of levodopa, for about 12 hours or more, preferably 14 hours or more, particularly preferably 16 hours or more by dosing three times per day, preferably two times per day.

The combined drug of the compound of the present invention and any of these other drugs may be administered in the form of a combination preparation containing both components in a single formulation, or may be administered in the form of separate formulations. The administration in the form of separate formulations includes simultaneous administration and time lag administration. In the case of time lag administration, the other drug may be administered after the compound of the present invention is administered, or the compound of the present invention may be administered after the other drug is administered. The respective administration routes may be the same or different.

The dose of the other drug can be appropriately selected on the basis of a clinically used dose. Further, the mixing ratio of the compound of the present invention and the other drug can be appropriately selected according to the age and body weight of the subject to be treated, administration route, dosing period, disease to be treated, symptoms, combination, etc. For example, with respect to one part by mass of the compound of the present invention, 0.01 to 100 parts by mass of the other drug may be used. As the other drug, two or more arbitrary drugs may be combined in an appropriate ratio and administered. Further, the above-described other drug includes not only drugs found to date but also drugs found in future.

In order to use the compound of the present invention or the combined drug of the compound of the present invention and other drug for the above-described purpose, it is generally administered systemically or locally in the form of an oral or parenteral formulation.

The dose of the compound of the present invention varies depending on the age, body weight, symptoms, therapeutic effect, administration route, treatment time, etc., however, the compound of the present invention is generally orally administered at a dose of from 100 mg to 3 g per human adult one to several times per day, or is parenterally administered at a dose of from 10 mg to 1 g per human adult one to several times per day, or is continuously administered intravenously during a period of from 1 hour to 24 hours in a day.

As described above, it is a matter of course that the dose varies depending on various conditions, and therefore, a dose less than the above-described dose may be sufficient in some cases, whereas a dose exceeding the above range may be required in some cases.

When the compound of the present invention or the combined drug of the compound of the present invention and other drug is administered, it is used by being formulated into a solid preparation for internal use or a liquid preparation for internal use for oral administration, a sustained-release preparation for oral administration or an injectable preparation, a preparation for external use, an inhalant, or a suppository for parenteral administration, or the like.

Examples of the solid preparation for internal use for oral administration include tablets, pills, capsules, powders, and granules. Examples of the capsules include hard capsules and soft capsules.

In such a solid preparation for internal use, one or more active substance(s) is/are formulated into a preparation according to a common procedure without being mixed with any additives or by being mixed with an excipient (such as lactose, mannitol, glucose, microcrystalline cellulose, or starch), a binder (such as hydroxypropyl cellulose, polyvinylpyrrolidone, or magnesium aluminometasilicate), a disintegrant (such as calcium glycolate cellulose), a lubricant (such as magnesium stearate), a stabilizer, a dissolution aid (such as glutamic acid or aspartic acid) or the like. Further, if necessary, the preparation may be coated with a coating agent (such as white soft sugar, gelatin, hydroxypropyl cellulose, or hydroxypropylmethy cellulose phthalate), or may be coated with two or more layers. Further, capsules made of an absorbable substance such as gelatin are also included.

Examples of the liquid preparation for internal use for oral administration include pharmaceutically acceptable liquid preparations, suspensions, emulsions, syrups, and elixirs. In such a liquid preparation, one or more active substance(s) is/are dissolved, suspended, or emulsified in a generally used diluent (such as purified water, ethanol, or a mixed liquid thereof). Further, this liquid preparation may contain a wetting agent, a suspending agent, an emulsifying agent, a sweetening agent, a flavoring agent, an aromatizing agent, a preservative, or a buffer.

Further, a sustained-release preparation for oral administration is also effective. A gel forming substance to be used in such a sustained-release preparation is a substance which can swell by absorbing a solvent and form a jelly-like substance in which the fluidity has been lost by connecting the resulting colloidal particles to one another to form a three-dimensional net like structure. The gel forming substance is used mainly as a binder, a viscosity increasing agent, and a sustained-release base in pharmaceutical use. For example, gum arabic, agar, polyvinylpyrrolidone, sodium alginate, propylene glycol alginate ester, a carboxyvinyl polymer, carboxymethyl cellulose, sodium carboxymethyl cellulose, guar gum, gelatin, hydroxypropylmethyl cellulose, hydroxypropyl cellulose, polyvinyl alcohol, methyl cellulose, or hydroxyethylmethyl cellulose can be used.

Examples of the injectable preparation for parenteral administration include solutions, suspension, emulsions, and solid injectable preparations which are dissolved or suspended in a solvent before use. The injectable preparation is used by dissolving, suspending, or emulsifying one or more active substance(s) in a solvent. Examples of the solvent include injectable distilled water, physiological saline, vegetable oils, propylene glycol, polyethylene glycol, alcohols such as ethanol, and a combination thereof. The injectable preparation may contain a stabilizer, a dissolution aid (such as glutamic acid, aspartic acid, or Polysorbate 80 (registered trademark)), a suspending agent, an emulsifying agent, a soothing agent, a buffer, a preservative, or the like. The injectable preparation is produced by sterilization in a final step or by an aseptic procedure. It is also possible to use the injectable preparation as an aseptic solid preparation (for example, a lyophilized product is produced and dissolved in sterilized or aseptic injectable distilled water or another solvent before use).

Examples of the dosage form of the preparation for external use for parenteral administration include propellants, inhalants, sprays, aerosols, ointments, gels, creams, poultices, plasters, liniments, and nasal agents. Such a preparation contains one or more active substance(s) and is prepared according to a known method or a commonly used formulation.

The propellant, inhalant, and spray may contain, other than a generally used diluent, a stabilizer such as sodium hydrogen sulfite and a buffer which provides isotonicity, for example, an isotonic agent such as sodium chloride, sodium citrate, or citric acid. A method for producing the spray is described in detail in, for example, U.S. Pat. Nos. 2,868,691 and 3,095,355.

Examples of the inhalant for parenteral administration include aerosols, powders for inhalation, and liquids for inhalation. The liquid for inhalation may be in such a form that it is used by being dissolved or suspended in water or another appropriate vehicle before use.

Such an inhalant is prepared according to a known method.

For example, a liquid for inhalation is prepared by appropriately selecting a preservative (such as benzalkonium chloride or paraben), a colorant, a buffer (such as sodium phosphate or sodium acetate), an isotonic agent (such as sodium chloride or concentrated glycerin), a viscosity increasing agent (such as carboxyvinyl polymer), an absorption enhancer, or the like according to need.

A powder for inhalation is prepared by appropriately selecting a lubricant (such as stearic acid or a salt thereof), a binder (such as starch or dextrin), an excipient (such as lactose or cellulose), a colorant, a preservative (such as benzalkonium chloride or paraben), an absorption enhancer, or the like according to need.

When a liquid for inhalation is administered, a sprayer (such as an atomizer or a nebulizer) is usually used, and when a powder for inhalation is administered, an inhalator for a powder preparation is usually used.

The ointment is produced according to a known or commonly used formulation. For example, an ointment is prepared by mixing or melting one or more active substance(s) in a base. The ointment base is selected from known or commonly used bases. Examples of the ointment base include higher fatty acids and higher fatty acid esters (such as adipic acid, myristic acid, palmitic acid, stearic acid, oleic acid, adipate, myristate, palmitate, stearate, and oleate), waxes (such as beeswax, spermaceti wax, and ceresin), surfactants (such as polyoxyethylene alkyl ether phosphate), higher alcohols (such as cetanol, stearyl alcohol, and cetostearyl alcohol), silicone oils (such as dimethylpolysiloxane), hydrocarbons (such as hydrophilic petrolatum, white petrolatum, purified lanolin, and liquid paraffin), glycols (such as ethylene glycol, diethylene glycol, propylene glycol, polyethylene glycol, and Macrogol), vegetable oils (such as castor oil, olive oil, sesame oil, and terrapin oil), animal oils (such as mink oil, egg yolk oil, squalane, and squalene), water, absorption enhancers, and anti-rash agents. From these bases, one base is selected and used alone or two or more bases are selected and used in admixture. The ointment may further contain a moisturizer, a preservative, a stabilizer, an antioxidant, an aromatizing agent, or the like.

The gel is produced according to a known or commonly used formulation. For example, a gel may be prepared by melting one or more active substance(s) in a base. The gel base is selected from known or commonly used bases. Examples of the gel base include lower alcohols (such as ethanol and isopropyl alcohol), gelling agents (such as carboxymethyl cellulose, hydroxyethyl cellulose, hydroxypropyl cellulose, and ethyl cellulose), neutralizing agents (such as triethanolamine and diisopropanolamine), surfactants (such as polyethylene glycol monostearate), gums, water, absorption enhancers, and anti-rash agents. From these bases, one base is selected and used alone or two or more bases are selected and used in admixture. The gel may further contain a preservative, an antioxidant, an aromatizing agent, or the like.

The cream is produced according to a known or commonly used formulation. For example, a cream is produced by melting or emulsifying one or more active substance(s) in a base. The cream base is selected from known or commonly used bases. Examples of the cream base include higher fatty acid esters, lower alcohols, hydrocarbons, polyhydric alcohols (such as propylene glycol and 1,3-butylene glycol), higher alcohols (such as 2-hexyldecanol and cetanol), emulsifying agents (such as polyoxyethylene alkyl ethers and fatty acid esters), water, absorption enhancers, and anti-rash agents. From these bases, one base is selected and used alone or two or more bases are selected and used in admixture. The cream may further contain a preservative, an antioxidant, an aromatizing agent, or the like.

The poultice is produced according to a known or commonly used formulation. For example, a poultice is produced by melting one or more active substance(s) in a base to form a kneaded material, followed by applying and spreading the kneaded material on a support. The poultice base is selected from known or commonly used bases. Examples of the poultice base include viscosity increasing agents (such as polyacrylic acid, polyvinylpyrrolidone, gum arabic, starch, gelatin, and methyl cellulose), wetting agents (such as urea, glycerin, and propylene glycol), fillers (such as kaolin, zinc oxide, talc, calcium, and magnesium), water, dissolution aids, tackifiers, and anti-rash agents. From these bases, one base is selected and used alone or two or more bases are selected and used in admixture. The poultice may further contain a preservative, an antioxidant, an aromatizing agent, or the like.

The plaster is produced according to a known or commonly used formulation. For example, a plaster is produced by melting one or more active substance(s) in a base and applying and spreading the melt on a support. The plaster base is selected from known or commonly used bases. Examples of the plaster base include polymeric bases, oils and fats, higher fatty acids, tackifiers, and anti-rash agents. From these bases, one base is selected and used alone or two or more bases are selected and used in admixture. The plaster may further contain a preservative, an antioxidant, an aromatizing agent, or the like.

The liniment is produced according to a known or commonly used formulation. For example, a liniment is prepared by dissolving, suspending, or emulsifying one or more active substance(s) in one or more material(s) selected from water, an alcohol (such as ethanol or polyethylene glycol), a higher fatty acid, glycerin, a soap, an emulsifying agent, and a suspending agent. The liniment may further contain a preservative, an antioxidant, an aromatizing agent, or the like.

As other compositions for parenteral administration, suppositories for intrarectal administration, pessaries for intravaginal administration, etc. each containing one or more active substance(s) and formulated according to a common procedure are included.

The entire contents of all Patent Literature and Non Patent Literature or Reference Literature explicitly cited in this description can be incorporated herein by reference as a part of this description.

EXAMPLES

Hereinafter, the present invention will be described in detail with reference to Examples and Biological Examples, however, the present invention is not limited thereto. The compound of the present invention and the compounds shown in Examples were named using ACD/Name (Version 6.00, manufactured by Advanced Chemistry Development, Inc.) or Chemdraw Ultra (Version 12.0, manufactured by Cambridge Soft Corporation).

The solvents in the parentheses indicated in a part of chromatographic separation and TLC denote the used elution solvents or developing solvents, and the ratio is expressed on a volume basis. The numerical values indicated in a part of NMR denote the measurement values by $^1$H-NMR when using the indicated measuring solvents.

Example 1

2-(Benzoyloxy)-2-methylpropanoic acid

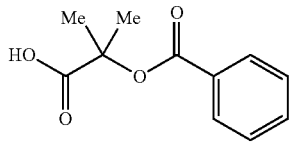 [SMILES: CC(C)(OC(=O)c1ccccc1)C(=O)O]

2-Hydroxyisobutyric acid (50 g) was dissolved in acetonitrile (480 mL). To this solution, pyridine (78 mL) was added, and then, benzoyl chloride (56 mL) was added thereto. The resulting solution was stirred at room temperature for 40 minutes. To the reaction mixture, 2 N hydrochloric acid (300 mL) was added to acidify the solution, and then, extraction was performed with ethyl acetate (400 mL×2). The organic layers were combined and dried over magnesium sulfate. After magnesium sulfate was removed by filtration, the solvent was concentrated under reduced pressure. The resulting residue was recrystallized from tert-butylmethyl ether/n-heptane, whereby the title compound (82 g, 82%) having the following physical properties was obtained.

TLC (Rf value): 0.37 (ethyl acetate)

NMR (300 MHz, CDCl$_3$): δ 8.20-9.40 (br, 1H), 8.01-8.06 (m, 2H), 7.53-7.59 (m, 1H), 7.40-7.46 (m, 2H), 1.73 (s, 6H)

Example 2

(2S)-Benzyl 2-((tert-butoxycarbonyl)amino)-3-(3,4-dihydroxyphenyl)propanoate

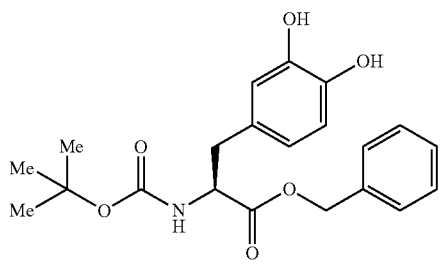 [SMILES: CC(C)(C)OC(=O)N[C@@H](Cc1ccc(O)c(O)c1)C(=O)OCc1ccccc1]

To (S)-3,4-dihydroxyphenylalanine (L-DOPA, 10.0 g), purified water (30 mL) was added under an argon atmosphere to form a suspension. To this solution, triethylamine (14.2 mL) was added, and then, a solution of di-tert-butyl-dicarbonate (Boc$_2$O, 13.3 g) in tetrahydrofuran (30 mL) was added thereto at room temperature. The resulting solution was stirred at room temperature for 14 hours. To the reaction mixture, 2 N hydrochloric acid (61 mL) was added under ice-cooling to acidify the solution, and then, extraction was performed with ethyl acetate (200 mL×2). The organic layers were combined and washed with a saturated aqueous solution of sodium chloride (200 mL), and then dried over magnesium sulfate. After magnesium sulfate was removed by filtration, the solvent was concentrated under reduced pressure. The resulting residue was used in the subsequent step without purification.

TLC (Rf value): 0.37 (dichloromethane:methanol:acetic acid=17:3:1)

The crude product obtained in the previous step was dissolved in N,N-dimethylformamide (51 mL). To this solution, potassium hydrogen carbonate (7.6 g) was added under an argon atmosphere, and then, benzyl bromide (7.3 mL) was added thereto. The resulting solution was stirred at room temperature for 7 hours. To the reaction mixture, 2 N hydrochloric acid (92 mL) was added under ice-cooling to acidify the solution, and then, extraction was performed with a mixed solution of n-heptane and ethyl acetate (1:1) (150 mL×2). The organic layers were combined and washed with water (75 mL×2) and a saturated aqueous solution of sodium chloride (75 mL), and then dried over magnesium sulfate. After magnesium sulfate was removed by filtration, the solvent was concentrated under reduced pressure. The resulting residue was recrystallized from ethyl acetate/n-heptane, whereby the title compound (16.2 g, 2-step yield: 82%) having the following physical properties was obtained.

TLC (Rf value): 0.64 (n-hexane:ethyl acetate:acetic acid=50:50:1)

NMR (300 MHz, CDCl$_3$): δ 7.31-7.40 (m, 5H), 6.98 (d, J=7.8 Hz, 1H), 6.44 (dd, J=7.8, 1.8 Hz, 1H), 6.40 (d, J=1.8 Hz, 1H), 5.26-5.64 (br, 2H), 5.05-5.23 (m, 2H), 5.00 (d, J=8.1 Hz, 1H), 4.50-4.58 (m, 1H), 2.94 (d, J=5.7 Hz, 2H), 1.41 (s, 9H)

Example 3

(2S)-((4-(3-Benzyloxy)-2-((tert-butoxycarbonyl)amino)-3-oxopropyl-1,2-phenylene)bis(oxy))bis(2-methyl-1-oxopropan-2,1-diyl)dibenzoate

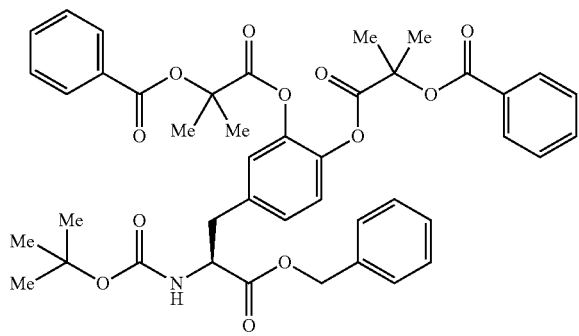 [SMILES: CC(C)(C)OC(=O)N[C@@H](Cc1ccc(OC(=O)C(C)(C)OC(=O)c2ccccc2)c(OC(=O)C(C)(C)OC(=O)c2ccccc2)c1)C(=O)OCc1ccccc1]

To the compound (90.7 g) produced in Example 1, toluene (227 mL) was added to form a suspension. To this solution, N,N-dimethylformamide (0.8 mL) was added under an argon atmosphere, and then, thionyl chloride (38.2 mL) was added thereto. The reaction mixture was stirred at 70° C. for 1 hour. The reaction mixture was cooled to room temperature and then concentrated under reduced pressure. To the residue, toluene (170 mL) was added, and the resulting solution was concentrated under reduced pressure. This procedure was repeated twice, whereby an acid chloride was obtained.

The compound (76.7 g) produced in Example 2 was dissolved in acetonitrile (100 mL) under an argon atmosphere. To this solution, triethylamine (83 mL) was added under ice-cooling, and subsequently, the acid chloride produced by the previous reaction was added thereto over 15 minutes. The resulting solution was stirred for 1 hour under ice-cooling. To the reaction mixture, an aqueous solution of 10% sodium hydrogen carbonate (800 mL) was added, and then, extraction was performed with ethyl acetate (800 mL×2). The organic layers were combined, and washed with a saturated aqueous solution of sodium chloride (800 mL), and then dried over sodium sulfate. After sodium sulfate was removed by filtration, the filtrate was concentrated under reduced pressure. The resulting residue was purified by silica gel chromatography (a medium-pressure preparative liquid chromatograph, Redisep manufactured by Teledyne Isco, Inc. (column: main column 1.5 kg, n-hexane:ethyl acetate=8:2-7:3 (gradient time: 15 minutes), fractionation mode), whereby the title compound (118 g, 95%) having the following physical properties was obtained.

TLC (Rf value): 0.44 (n-hexane:ethyl acetate=3:1)

NMR (300 MHz, CDCl$_3$): δ 8.01-8.07 (m, 4H), 7.52-7.60 (m, 2H), 7.38-7.49 (m, 4H), 7.25-7.32 (m, 5H), 7.15 (d, J=8.1 Hz, 1H), 7.05 (s, 1H), 6.91 (d, J=8.1 Hz, 1H), 5.12 (s, 2H), 5.02 (d, J=7.8 Hz, 1H), 4.55-4.63 (m, 1H), 3.09 (d, J=5.4 Hz, 2H), 1.81-1.85 (m, 12H), 1.39 (s, 9H)

Example 4

(2S)-3-(3,4-Bis((2-benzoyloxy)-2-methylpropanoyl)oxy)phenyl)-2-((tert-butoxycarbonyl)amino)propanoic acid

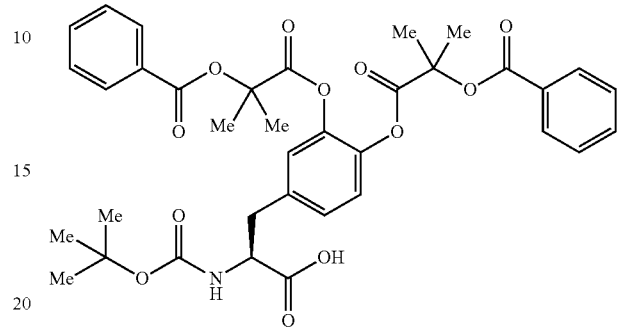

The compound (134.4 g) produced in Example 3 was dissolved in ethanol (400 mL). To this solution, 10% palladium-carbon (50% hydrated, 14.6 g) was added under an argon atmosphere. This solution was stirred at room temperature for 2 hours under a hydrogen atmosphere. To the reaction mixture, ethyl acetate (400 mL) was added, and the resulting mixture was filtered through Celite (trade name). Then, the filtrate was concentrated under reduced pressure. The resulting residue was purified by silica gel chromatography (a medium-pressure preparative liquid chromatograph, W-prep 2XY manufactured by Yamazen Corporation (column: main column 5L, inject column 3L, n-hexane:ethyl acetate=3:7-0:1 (gradient time: 20 minutes), fractionation mode GR), whereby the title compound (110 g, 86%) having the following physical properties was obtained.

TLC (Rf value): 0.38 (n-hexane:ethyl acetate:acetic acid=100:100:1)

NMR (300 MHz, CD$_3$OD): δ 8.02-8.07 (m, 4H), 7.59-7.66 (m, 2H), 7.46-7.52 (m, 4H), 7.13-7.21 (m, 3H), 4.33 (dd, J=9.0, 5.1 Hz, 1H), 3.18 (dd, J=13.5, 5.1 Hz, 1H), 2.93 (dd, J=13.5, 9.0 Hz, 1H), 1.82 (s, 12H), 1.33 (s, 9H)

Example 5

(2S)-2-Amino-3-(3,4-bis((2-(benzoyloxy)-2-methylpropanoyl)oxy)phenyl)propanoic acid hydrochloride

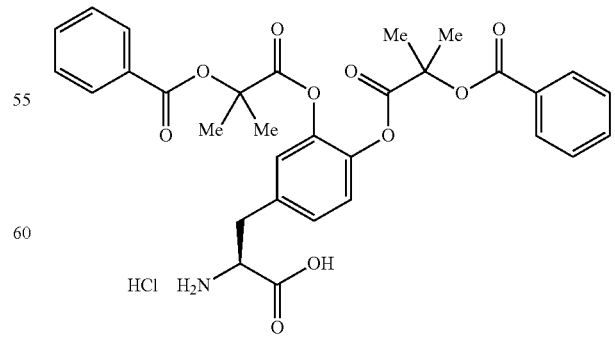

To the compound (110 g) produced in Example 4, a 4 N hydrochloric acid-dioxane solution (500 mL) was added. The resulting solution was stirred at room temperature for 1 hour. Then, the reaction mixture was concentrated under reduced pressure, whereby the title compound (93.2 g, 94%) having the following physical properties was obtained. The obtained title compound was amorphous and had a melting point of from about 112.0 to 117.0° C. (measured by the capillary method described in the Japanese Pharmacopoeia).

TLC (Rf value): 0.64 (ethyl acetate:acetic acid:water=5:5:1)

NMR (300 MHz, CD$_3$OD): δ 8.02-8.06 (m, 4H), 7.60-7.67 (m, 2H), 7.46-7.52 (m, 4H), 7.25-7.30 (m, 3H), 4.24 (dd, J=8.4, 5.1 Hz, 1H), 3.37 (dd, J=15.0, 5.1 Hz, 1H), 3.13 (dd, J=15.0, 8.4 Hz, 1H), 1.83 (s, 6H), 1.82 (s, 6H)

Figure 16:
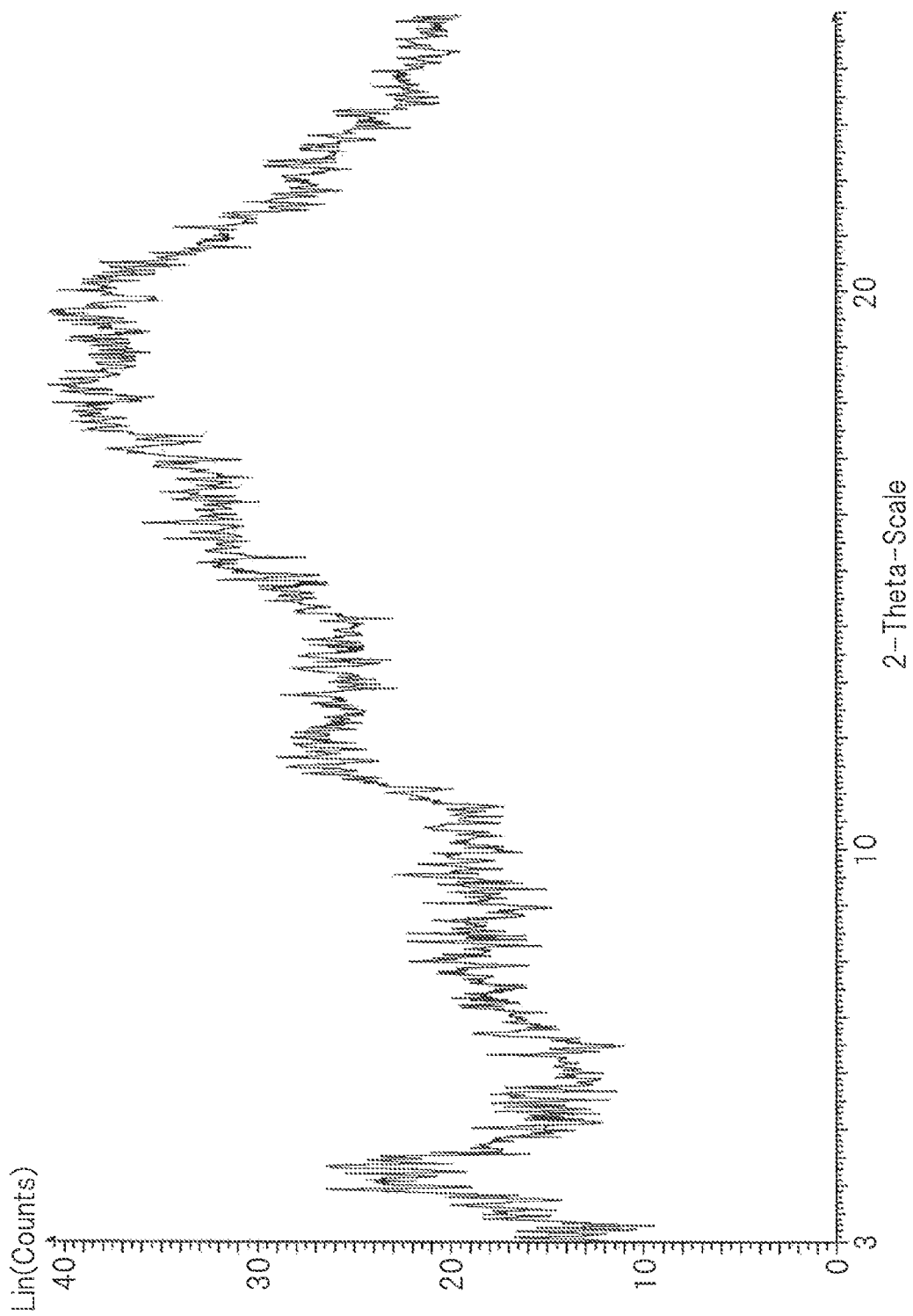
FIG. 16 shows a powder X-ray diffraction spectrum chart of amorphous (2S)-2-amino-3-(3,4-bis((2-(benzoyloxy)-2-methylpropanoyl)oxy)phenyl)propanoic acid hydrochloride obtained in Example 5.

The powder X-ray diffraction spectrum chart, differential scanning calorimetry chart, and infrared absorption spectrum chart of the thus obtained amorphous (2S)-2-amino-3-(3,4-bis((2-(benzoyloxy)-2-methylpropanoyl)oxy)phenyl)propanoic acid hydrochloride are shown in FIG. 16, FIG. 17, and FIG. 18, respectively.

(1) Powder X-Ray Diffraction Spectroscopy

[Measurement Conditions]

Apparatus: BRUKER DISCOVER with GADDS (C2)

Target: Cu

Filter: Not used

Voltage: 40 kV

Current: 40 mA

Exposure time: 180 sec

[Results]

In the powder X-ray diffraction spectroscopy using Cu—Kα radiation, no crystalline peaks were observed.

(2) Differential Scanning calorimetry

[Measurement Conditions]

Apparatus: SEIKO INSTRUMENT DSC 6200

Amount of sample: 3.73 mg

Sample cell: Aluminum Standard 40 μL (having a lid with a pinhole)

Nitrogen flow rate: 40 mL/min

Temperature elevation rate: 10° C./min

Temperature elevation starting temperature: 25° C.

[Results]

As a result, it was found that the compound has an endothermic peak at around 82.83° C.

(3) Infrared Absorption Spectroscopy

[Measurement Conditions]

Apparatus: FTIR-660 Plus/SENSIR DuraScope, JASCO Corporation

Resolution: 4 cm$^{-1}$

Number of scanning times: 32

[Results]

IR (Attenuated total reflectance method (hereinafter abbreviated as "ATR method"): 3409, 2992, 2944, 2865, 2629, 1970, 1774, 1718, 1655, 1601, 1585, 1508, 1470, 1452, 1428, 1388, 1369, 1317, 1290, 1258, 1204, 1168, 1125, 1093, 1070, 1026, 1003, 958, 866, 806, 741, 714, 687, 617, 530, 496, 467, 447, and 419 cm$^{-1}$ Reference Example 1

Benzyl 3-hydroxy-2,2-dimethylpropanoate

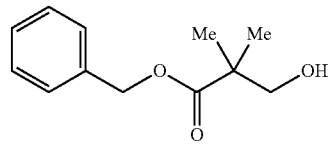 [SMILES: CC(C)(CO)C(=O)OCc1ccccc1]

2,2-Dimethyl-3-hydroxypropanoic acid (10.0 g) was dissolved in N,N-dimethylformamide (150 mL). To this solution, potassium hydrogen carbonate (10.2 g) was added, and then, benzyl bromide (10.7 mL) was added thereto. The resulting solution was stirred at room temperature for 16 hours. To the reaction mixture, water (300 mL) was added, and extraction was performed with a mixed solution of n-hexane and ethyl acetate (1:4) (200 mL×2). The organic layers were combined and washed with a saturated aqueous solution of sodium chloride (200 mL), and then dried over magnesium sulfate. After magnesium sulfate was removed by filtration, the solvent was concentrated under reduced pressure. The resulting residue was purified by silica gel chromatography (a medium-pressure preparative liquid chromatograph, W-prep 2XY manufactured by Yamazen Corporation (column: main column 4L, inject column 3L, n-hexane:ethyl acetate=1:0-1:1 (gradient time: 15 minutes), fractionation mode GR), whereby the title compound (17.6 g, 100%) having the following physical properties was obtained.

TLC (Rf value): 0.39 (n-hexane:ethyl acetate=3:1)

NMR (CDCl$_3$): δ 7.29-7.41 (m, 5H), 5.15 (s, 2H), 3.57 (d, J=6.3 Hz, 2H), 1.22 (s, 6H)

Reference Example 2

3-(Benzyloxy)-2,2-dimethyl-3-oxopropylthiophene-2-carboxylate

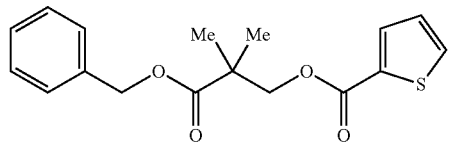 [SMILES: CC(C)(COC(=O)c1cccs1)C(=O)OCc1ccccc1]

The compound (2.0 g) produced in Reference Example 1 was dissolved in dichloromethane (30 mL). To this solution, triethylamine (2.7 mL) was added, and then, 2-thiophenecarboxylic acid chloride (1.5 mL) was added thereto under ice-cooling. The resulting solution was stirred for 2 hours under ice-cooling. To the reaction mixture, a saturated aqueous solution of sodium carbonate (30 mL) was added, and then, extraction was performed with ethyl acetate (100 mL×2). The organic layers were combined, and washed with a saturated aqueous solution of sodium chloride (30 mL), and then dried over magnesium sulfate. After magnesium sulfate was removed by filtration, the solvent was concentrated under reduced pressure. The resulting residue was purified by silica gel chromatography (a medium-pressure preparative liquid chromatograph, W-prep 2XY manufactured by Yamazen Corporation (column: main column 2L, inject column L, n-hexane:ethyl acetate=1:0-8:2 (gradient time: 15 minutes), fractionation mode GR), whereby the title compound (3.0 g, 100%) having the following physical properties was obtained.

TLC (Rf value): 0.65 (n-hexane:ethyl acetate=3:1)

NMR (CDCl$_3$): δ 7.67-7.69 (m, 1H), 7.52-7.55 (m, 1H), 7.26-7.34 (m, 5H), 7.05-7.08 (m, 1H), 5.16 (s, 2H), 4.34 (s, 2H), 1.28 (s, 6H)

Reference Example 3

2,2-Dimethyl-3-((thiophene-2-carbonyl)oxy)propanoic acid

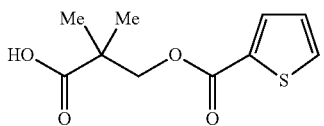 [SMILES: CC(C)(COC(=O)c1cccs1)C(=O)O]

The compound (3.0 g) produced in Reference Example 2 was dissolved in ethanol (20 mL). To this solution, 10% palladium-carbon (50% hydrated, 500 mg) was added under an argon atmosphere. This solution was stirred at room temperature for 1 hour under a hydrogen atmosphere. To the reaction mixture, ethyl acetate (20 mL) was added, and the resulting mixture was filtered through Celite (trade name). Then, the filtrate was concentrated under reduced pressure. The resulting residue was purified by silica gel chromatography (a medium-pressure preparative liquid chromatograph, W-prep 2XY manufactured by Yamazen Corporation (column: main column 2L, inject column L, n-hexane:ethyl acetate=8:2-0:1 (gradient time: 15 minutes), fractionation mode GR), whereby the title compound (719 mg, 33%) having the following physical properties was obtained.

TLC (Rf value): 0.60 (ethyl acetate)

NMR (CDCl$_3$): δ 7.77-7.79 (m, 1H), 7.53-7.55 (m, 1H), 7.06-7.10 (m, 1H), 4.34 (s, 2H), 1.33 (s, 6H)

Reference Example 4

(2S)-((4-(3-(Benzyloxy)-2-((tert-butoxycarbonyl)amino)-3-oxopropyl)-1,2-phenylene)bis(oxy))bis(2,2-dimethyl-3-oxopropan-3,1-diyl)bis(thiophene-2-carboxylate)

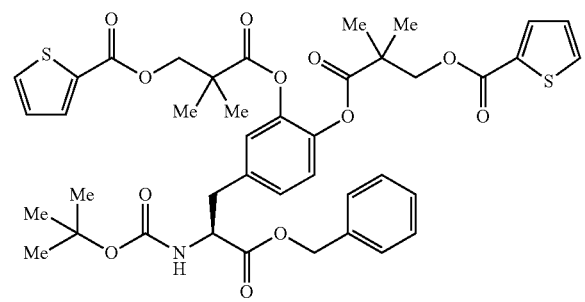 [SMILES: CC(C)(C)OC(=O)N[C@@H](Cc1ccc(OC(=O)C(C)(C)COC(=O)c2cccs2)c(OC(=O)C(C)(C)COC(=O)c2cccs2)c1)C(=O)OCc1ccccc1]

By performing the same procedure as in Example 3 using the compound (735 mg) produced in Example 2 and the compound (1.3 g) produced in Reference Example 3 in place of the compound produced in Example 1, the title compound (1.5 g, 99%) having the following physical properties was obtained.

TLC (Rf value): 0.60 (n-hexane:ethyl acetate=1:1)

NMR (CDCl$_3$): δ 7.79-7.82 (m, 2H), 7.53-7.58 (m, 2H), 7.26-7.31 (m, 5H), 7.06-7.11 (m, 2H), 7.00 (d, J=8.4 Hz, 1H), 6.87-6.94 (m, 2H), 5.10 (s, 2H), 4.96-5.04 (m, 1H), 4.52-4.59 (m, 1H), 4.43 (s, 2H), 4.42 (s, 2H), 2.99-3.06 (m, 2H), 1.34-1.35 (m, 21H)

Reference Example 5

(2S)-3-(3,4-Bis((2,2-dimethyl-3-((thiophene-2-carbonyl)oxy)propanoyl)oxy)phenyl)-2-(tert-butoxycarbonyl)amino)propanoic acid

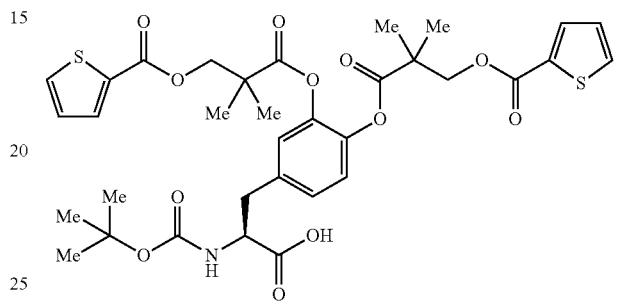

By performing the same procedure as in Example 4 using the compound (1.5 g) produced in Reference Example 4 in place of the compound produced in Example 3, the title compound (588 mg, 44%) having the following physical properties was obtained.

TLC (Rf value): 0.12 (ethyl acetate)

NMR (CDCl$_3$): δ 7.74-7.85 (m, 2H), 7.03-7.18 (m, 4H), 6.99-7.12 (m, 3H), 4.43 (s, 2H), 4.42 (s, 2H), 4.05-4.22 (m, 1H), 3.06-3.14 (m, 1H), 2.83-2.91 (m, 1H), 1.36-1.48 (m, 21H)

Reference Example 6

(2S)-2-Amino-3-(3,4-bis((2,2-dimethyl-3-((thiophene-2-carbonyl)oxy)propanoyl)oxy)phenyl)propanoic acid hydrochloride

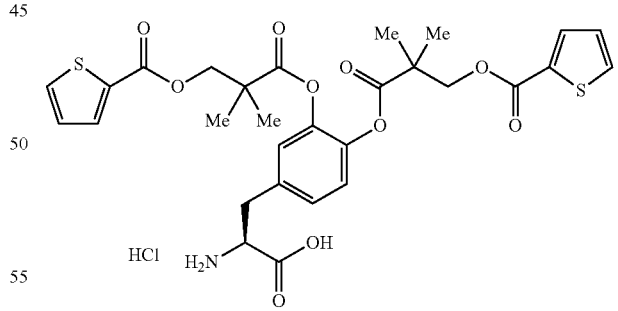

By performing the same procedure as in Example 5 using the compound (580 mg) produced in Reference Example 5 in place of the compound produced in Example 4, the title compound (528 mg, 100%) having the following physical properties was obtained.

TLC (Rf value): 0.74 (ethyl acetate:acetic acid:water=3:1:1)

NMR (CD$_3$OD): δ 7.75-7.84 (m, 4H), 7.14-7.23 (m, 5H), 4.45 (s, 2H), 4.44 (s, 2H), 4.17-4.23 (m, 1H), 3.35-3.38 (m, 1H), 3.09 (dd, J=14.4, 8.4 Hz, 1H), 1.41-1.44 (m, 12H)

Reference Example 7

3-(Benzyloxy)-2,2-dimethyl-3-oxopropyl thiophene-3-carboxylate

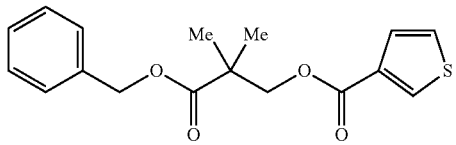 [SMILES: CC(C)(COC(=O)c1ccsc1)C(=O)OCc1ccccc1]

By performing the same procedure as in Reference Example 2 using the compound (2.0 g) produced in Reference Example 1 and 3-thiophenecarboxylic acid chloride (2.1 g) in place of 2-thiophenecarboxylic acid chloride, the title compound (3.1 g, 100%) having the following physical properties was obtained.

TLC (Rf value): 0.50 (n-hexane:ethyl acetate=5:1)
NMR (CDCl$_3$): δ 7.89-7.91 (m, 1H), 7.39-7.42 (m, 1H), 7.24-7.38 (m, 6H), 5.16 (s, 2H), 4.31 (s, 2H), 1.32 (s, 6H)

Reference Example 8

2,2-Dimethyl-3-((thiophene-3-carbonyl)oxy)propanoic acid

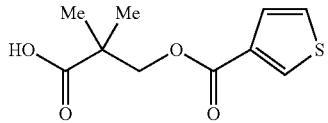 [SMILES: CC(C)(COC(=O)c1ccsc1)C(=O)O]

By performing the same procedure as in Reference Example 3 using the compound (3.1 g) produced in Reference Example 7 in place of the compound produced in Reference Example 2, the title compound (354 mg, 16%) having the following physical properties was obtained.

TLC (Rf value): 0.12 (ethyl acetate)
NMR (CDCl$_3$): δ 8.08-8.10 (m, 1H), 7.48-7.51 (m, 1H), 7.27-7.31 (m, 1H), 4.32 (s, 2H), 1.33 (s, 6H)

Reference Example 9

(2S)-((4-(3-(Benzyloxy)-2-(tert-butoxycarbonyl) amino)-3-oxopropyl)-1,2-phenylene)bis(oxy))bis(2, 2-dimethyl-3-oxopropan-3,1-diyl)bis(thiophene-3-carboxylate)

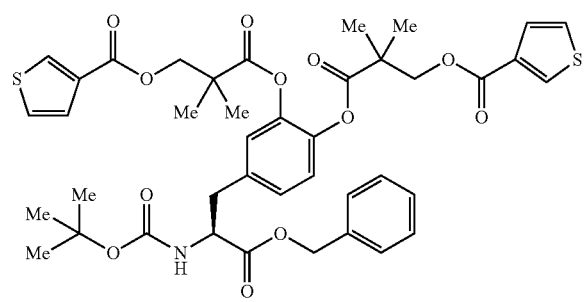 [SMILES: CC(C)(C)OC(=O)N[C@@H](Cc1ccc(OC(=O)C(C)(C)COC(=O)c2ccsc2)c(OC(=O)C(C)(C)COC(=O)c2ccsc2)c1)C(=O)OCc1ccccc1]

By performing the same procedure as in Example 3 using the compound (533 mg) produced in Example 2 and the compound (785 mg) produced in Reference Example 8 in place of the compound produced in Example 1, the title compound (1.1 g, 100%) having the following physical properties was obtained.

TLC (Rf value): 0.47 (n-hexane:ethyl acetate=2:1)
NMR (CDCl$_3$): δ 8.10-8.12 (m, 2H), 7.49-7.52 (m, 2H), 7.23-7.33 (m, 7H), 6.85-6.97 (m, 3H), 5.10 (s, 2H), 4.98 (d, J=8.7 Hz, 1H), 4.52-4.58 (m, 1H), 4.40 (s, 2H), 4.41 (s, 2H), 2.96-3.08 (m, 2H), 1.32-1.36 (m, 21H)

Reference Example 10

(2S)-3-(3,4-Bis((2,2-dimethyl-3-((thiophene-3-carbonyl)oxy)propanoyl)oxy)phenyl)-2-(tert-butoxycarbonyl)amino)propanoic acid

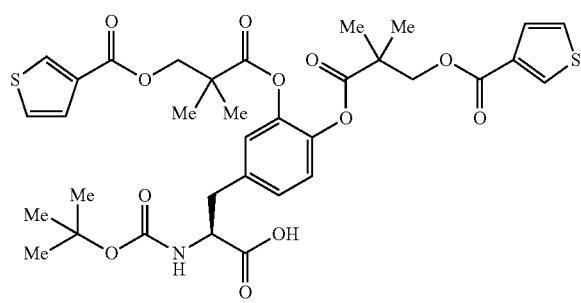 [SMILES: CC(C)(C)OC(=O)N[C@@H](Cc1ccc(OC(=O)C(C)(C)COC(=O)c2ccsc2)c(OC(=O)C(C)(C)COC(=O)c2ccsc2)c1)C(=O)O]

By performing the same procedure as in Example 4 using the compound (1.1 g) produced in Reference Example 9 in place of the compound produced in Example 3, the title compound (324 mg, 33%) having the following physical properties was obtained.

TLC (Rf value): 0.12 (ethyl acetate)
NMR (CDCl$_3$): δ 8.20-8.24 (m, 2H), 7.45-7.52 (m, 4H), 6.99-7.12 (m, 3H), 4.41 (s, 2H), 4.40 (s, 2H), 4.19-4.26 (m, 1H), 3.06-3.14 (m, 1H), 2.84-2.90 (m, 1H), 1.24-1.34 (m, 21H)

Reference Example 11

(2S)-2-Amino-3-(3,4-bis((2,2-dimethyl-3-((thiophene-3-carbonyl)oxy)propanoyl)oxy)phenyl) propanoic acid hydrochloride

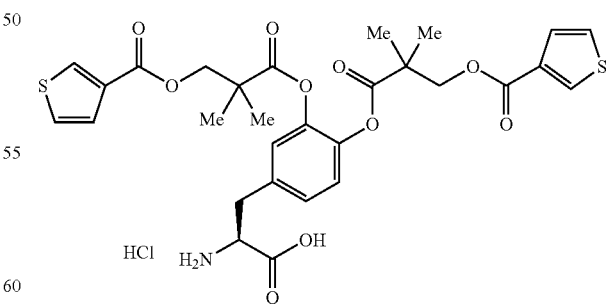

By performing the same procedure as in Example 5 using the compound (323 mg) produced in Reference Example 10 in place of the compound produced in Example 4, the title compound (294 mg, 100%) having the following physical properties was obtained.

TLC (Rf value): 0.57 (ethyl acetate:acetic acid:water=3:1:1)

NMR (CD₃OD): δ 8.20-8.24 (m, 2H), 7.46-7.51 (m, 4H), 7.12-7.21 (m, 3H), 4.42 (s, 2H), 4.41 (s, 2H), 4.14-4.21 (m, 1H), 3.31-3.35 (m, 1H), 3.05-3.10 (m, 1H), 1.41-1.43 (m, 12H)

Reference Example 12

3-(Benzyloxy)-2,2-dimethyl-3-oxopropyl 2-methoxybenzoate

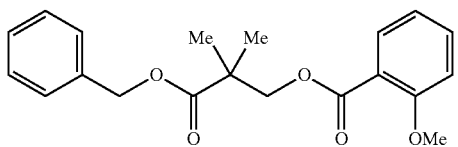 [SMILES: COc1ccccc1C(=O)OCC(C)(C)C(=O)OCc1ccccc1]

By performing the same procedure as in Reference Example 2 using the compound (1.5 g) produced in Reference Example 1 and 2-methoxybenzoyl chloride (1.6 mL) in place of 2-thiophenecarboxylic acid chloride, the title compound (1.8 g, 72%) having the following physical properties was obtained.

TLC (Rf value): 0.66 (n-hexane:ethyl acetate=2:1)

NMR (CDCl₃): δ 7.68 (dd, J=7.5, 2.1 Hz, 1H), 7.43-7.49 (m, 1H), 7.25-7.32 (m, 5H), 6.89-6.96 (m, 2H), 5.15 (s, 2H), 4.35 (s, 2H), 3.84 (s, 3H), 1.33 (s, 6H)

Reference Example 13

3-((2-Methoxybenzoyl)oxy)-2,2-dimethylpropanoic acid

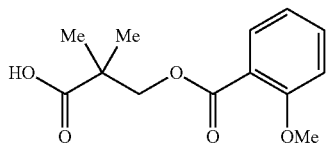 [SMILES: COc1ccccc1C(=O)OCC(C)(C)C(=O)O]

By performing the same procedure as in Reference Example 3 using the compound (1.8 g) produced in Reference Example 12 in place of the compound produced in Reference Example 2, the title compound (1.3 g, 91%) having the following physical properties was obtained.

TLC (Rf value): 0.12 (n-hexane:ethyl acetate=3:1)

NMR (CDCl₃): δ 7.78-7.82 (m, 1H), 7.43-7.47 (m, 1H), 6.93-6.99 (m, 2H), 4.34 (s, 2H), 3.86 (s, 3H), 1.34 (s, 6H)

Reference Example 14

(2S)-((4-(3-(Benzyloxy)-2-((tert-butoxycarbonyl)amino)-3-oxopropyl)-1,2-phenylene)bis(oxy))bis(2,2-dimethyl-3-oxopropan-3,1-diyl)bis(2-methoxybenzoate)

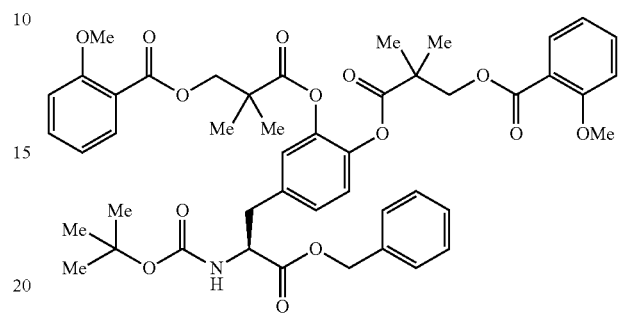

By performing the same procedure as in Example 3 using the compound (410 mg) produced in Example 2 and the compound (800 mg) produced in Reference Example 13 in place of the compound produced in Example 1, the title compound (592 mg, 65%) having the following physical properties was obtained.

TLC (Rf value): 0.74 (n-hexane:ethyl acetate=1:1)

NMR (CDCl₃): δ 7.76-7.81 (m, 2H), 7.41-7.50 (m, 2H), 7.25-7.31 (m, 5H), 6.82-6.99 (m, 7H), 5.07 (s, 2H), 4.94 (d, J=7.8 Hz, 1H), 4.48-4.55 (m, 1H), 4.41 (s, 4H), 3.84 (s, 6H), 2.94-3.03 (m, 2H), 1.28-1.39 (m, 21H)

Reference Example 15

(2S)-3-(3,4-Bis((3-((2-methoxybenzoyl)oxy-2,2-dimethylpropanoyl)oxy)phenyl)-2-(tert-butoxycarbonyl)amino)propanoic acid

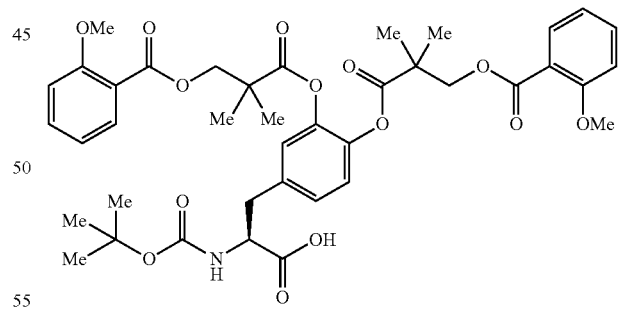

By performing the same procedure as in Example 4 using the compound (590 mg) produced in Reference Example 14 in place of the compound produced in Example 3, the title compound (406 mg, 77%) having the following physical properties was obtained.

TLC (Rf value): 0.12 (n-hexane:ethyl acetate=1:1)

NMR (CDCl₃): δ 7.77-7.86 (m, 2H), 7.44-7.51 (m, 2H), 6.93-7.05 (m, 7H), 4.94-5.01 (m, 1H), 4.32-4.59 (m, 5H), 3.86 (s, 3H), 3.84 (s, 3H), 3.07 (d, J=5.4 Hz, 2H), 1.34-1.41 (m, 21H)

Reference Example 16

(2S)-2-Amino-3-(3,4-bis((3-((2-methoxybenzoyl)oxy-2,2-dimethylpropanoyl)oxy)phenyl)propanoic acid hydrochloride

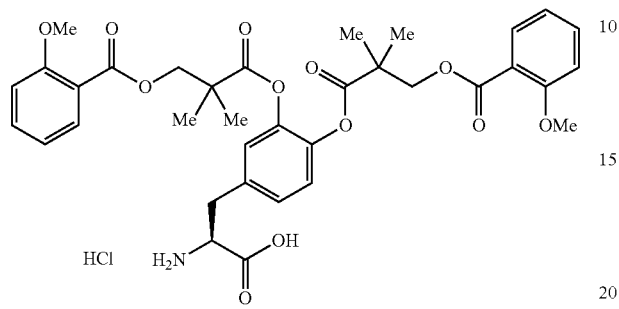

By performing the same procedure as in Example 5 using the compound (400 mg) produced in Reference Example 15 in place of the compound produced in Example 4, the title compound (360 mg, 98%) having the following physical properties was obtained.

TLC (Rf value): 0.45 (ethyl acetate:acetic acid:water=5:1:1)

NMR (CD$_3$OD): δ 7.70-7.75 (m, 2H), 7.49-7.53 (m, 2H), 7.02-7.21 (m, 5H), 6.95-7.02 (m, 2H), 4.40 (s, 2H), 4.38 (s, 2H), 4.14 (dd, J=8.7, 5.1 Hz, 1H), 3.82-3.83 (m, 6H), 3.25-3.30 (m, 1H), 3.04 (dd, J=14.7, 8.7 Hz, 1H), 1.37-1.46 (m, 12H)

Reference Example 17

(2S)-2-Amino-3-(3,4-bis((2,2-diethylbutanoyl)oxy)phenyl)propanoic acid hydrochloride

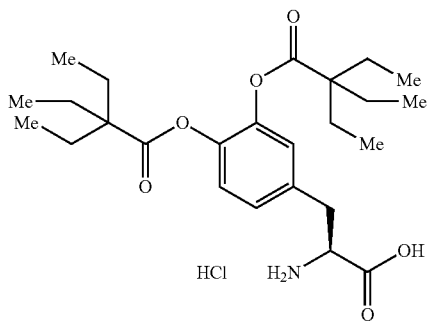 [SMILES: CCC(CC)(CC)C(=O)Oc1ccc(C[C@H](N)C(=O)O)cc1OC(=O)C(CC)(CC)CC ; Cl]

By performing the procedure of Example 3→Example 4→Example 5 using the compound produced in Example 2 and 2,2-diethylbutanoic acid in place of the compound produced in Example 1, the title compound having the following physical properties was obtained.

TLC (Rf value): 0.78 (ethyl acetate:acetic acid:water=3:1:1)

NMR (CD$_3$OD): δ 7.23 (dd, J=8.4, 1.8 Hz, 1H), 7.17 (d, J=8.4 Hz, 1H), 7.13 (d, J=1.8 Hz, 1H), 4.25 (dd, J=8.1, 5.4 Hz, 1H), 3.35 (dd, J=14.7, 5.4 Hz, 1H), 3.14 (dd, J=14.7, 8.1 Hz, 1H), 1.70-1.79 (m, 12H), 0.87-0.96 (m, 18H)

Reference Example 18

(2S)-2-Amino-3-(3,4-bis((2-ethyl-2-methylbutanoyl)oxy)phenyl)propanoic acid hydrochloride

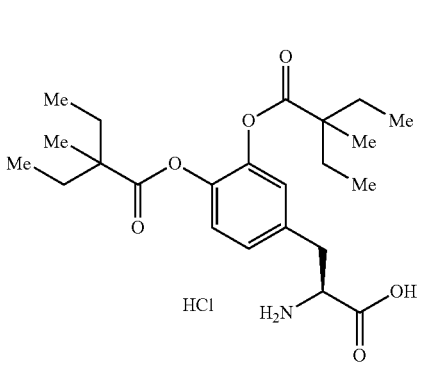 [SMILES: CCC(C)(CC)C(=O)Oc1ccc(C[C@H](N)C(=O)O)cc1OC(=O)C(C)(CC)CC ; Cl]

By performing the procedure of Example 3→Example 4→Example 5 using the compound produced in Example 2 and 2-ethyl-2-methylbutanoic acid in place of the compound produced in Example 1, the title compound having the following physical properties was obtained.

TLC (Rf value): 0.75 (ethyl acetate:acetic acid:water=3:1:1)

NMR (CD$_3$OD): δ 7.23 (dd, J=8.4, 2.1 Hz, 1H), 7.15 (d, J=8.4 Hz, 1H), 7.13 (d, J=2.1 Hz, 1H), 4.25 (dd, J=8.1, 5.1 Hz, 1H), 3.36 (dd, J=14.7, 5.1 Hz, 1H), 3.14 (dd, J=14.7, 8.1 Hz, 1H), 1.59-1.86 (m, 8H), 1.25 (s, 3H), 1.24 (s, 3H), 0.93-1.03 (m, 12H)

Reference Example 19

(2S)-2-Amino-3-(3,4-bis((4,4-dimethylpentanoyl)oxy)phenyl)propanoic acid hydrochloride

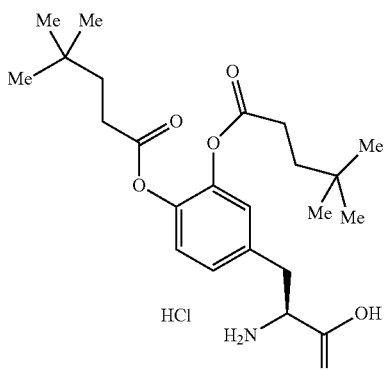

By performing the procedure of Example 3→Example 4→Example 5 using the compound produced in Example 2 and 4,4-dimethylpentanoic acid in place of the compound produced in Example 1, the title compound having the following physical properties was obtained.

TLC (Rf value): 0.63 (ethyl acetate:acetic acid:water=6:1:1)

NMR (CD₃OD): δ 7.18-7.24 (m, 3H), 4.23 (dd, J=8.4, 5.1 Hz, 1H), 3.38 (dd, J=14.7, 5.1 Hz, 1H), 3.12 (dd, J=14.7, 8.4 Hz, 1H), 2.52-2.58 (m, 4H), 1.61-1.67 (m, 4H), 0.89-1.17 (m, 18H)

Reference Example 20

(2S)-2-Amino-3-(3,4-bis((3,3-dimethylpent-4-enoyl)oxy)phenyl)propanoic acid hydrochloride

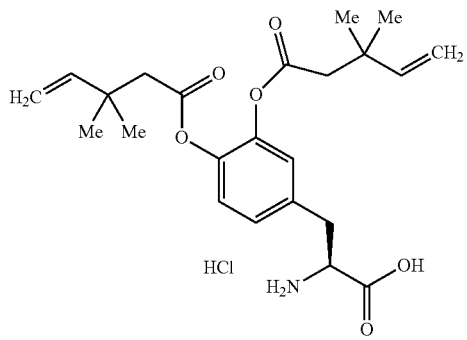 [SMILES: C=CC(C)(C)CC(=O)Oc1ccc(C[C@H](N)C(=O)O)cc1OC(=O)CC(C)(C)C=C ; Cl]

By performing the procedure of Example 3→Example 4→Example 5 using the compound produced in Example 2 and 3,3-dimethylpentenoic acid in place of the compound produced in Example 1, the title compound having the following physical properties was obtained.

TLC (Rf value): 0.45 (ethyl acetate:acetic acid:water=6:1:1)

NMR (CD₃OD): δ 7.13-7.25 (m, 3H), 5.99 (dd, J=17.4, 10.5 Hz, 1H), 5.01-5.10 (m, 2H), 4.23 (dd, J=8.4, 5.1 Hz, 1H), 3.37 (dd, J=14.7, 5.1 Hz, 1H), 3.11 (dd, J=14.7, 8.4 Hz, 1H), 2.57 (s, 2H), 2.56 (s, 2H), 1.21-1.22 (m, 12H)

Reference Example 21

(2S)-2-Amino-3-(3,4-bis((3-ethyl-3-methylpentanoyl)oxy)phenyl)propanoic acid hydrochloride

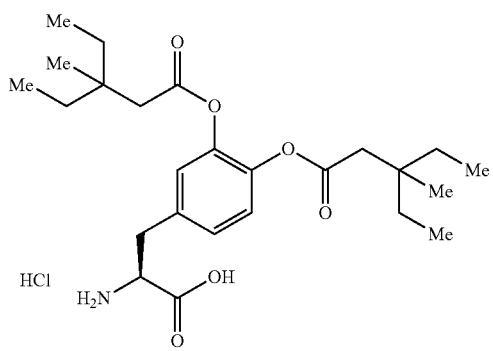 [SMILES: Cl ; CCC(C)(CC)CC(=O)Oc1ccc(C[C@H](N)C(=O)O)cc1OC(=O)CC(C)(CC)CC]

By performing the procedure of Example 3→Example 4→Example 5 using the compound produced in Example 2 and 3-ethyl-3-methylpentanoic acid in place of the compound produced in Example 1, the title compound having the following physical properties was obtained.

TLC (Rf value): 0.51 (ethyl acetate:acetic acid:water=5:1:1)

NMR (CD₃OD): δ 7.15-7.26 (m, 3H), 4.23 (dd, J=8.4, 5.1 Hz, 1H), 3.38 (dd, J=14.7, 5.1 Hz, 1H), 3.17 (dd, J=14.7, 8.4 Hz, 1H), 2.45 (s, 2H), 2.44 (s, 2H), 1.42-1.50 (m, 8H), 1.04 (s, 3H), 1.03 (s, 3H), 0.87-0.92 (m, 12H)

Reference Example 22

(2S)-2-Amino-3-(3,4-bis((3-isopropyl-4-methylpentanoyl)oxy)phenyl)propanoic acid hydrochloride

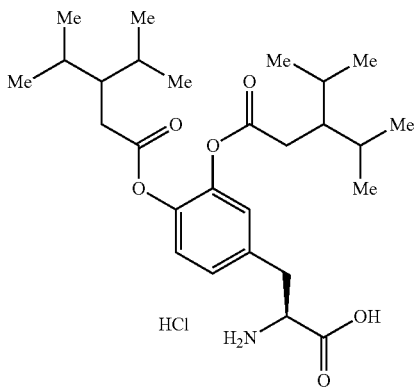 [SMILES: CC(C)C(CC(=O)Oc1ccc(C[C@H](N)C(=O)O)cc1OC(=O)CC(C(C)C)C(C)C)C(C)C ; Cl]

By performing the procedure of Example 3→Example 4→Example 5 using the compound produced in Example 2 and 3-isopropyl-4-methylpentanoic acid in place of the compound produced in Example 1, the title compound having the following physical properties was obtained.

TLC (Rf value): 0.67 (ethyl acetate:acetic acid=3:1)

NMR (CD₃OD): δ 7.15-7.26 (m, 3H), 4.13 (dd, J=8.4, 5.1 Hz, 1H), 3.20-3.30 (m, 1H), 3.05-3.13 (m, 1H), 2.47 (d, J=5.7 Hz, 2H), 2.46 (d, J=5.7 Hz, 2H), 1.79-1.90 (m, 4H), 1.65-1.72 (m, 2H), 0.89-0.99 (m, 24H)

Reference Example 23

(2S)-2-Amino-3-(3,4-bis((2-methylbenzoyl)oxy)phenyl)propanoic acid hydrochloride

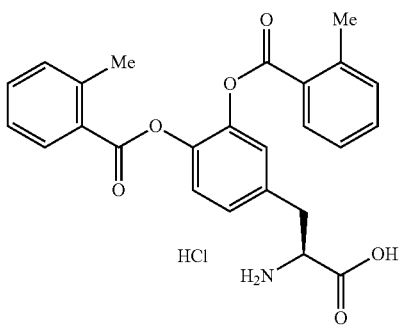 [SMILES: Cc1ccccc1C(=O)Oc1ccc(C[C@H](N)C(=O)O)cc1OC(=O)c1ccccc1C ; Cl]

By performing the procedure of Example 3→Example 4→Example 5 using the compound produced in Example 2 and 2-methylbenzoic acid in place of the compound produced in Example 1, the title compound having the following physical properties was obtained.

TLC (Rf value): 0.79 (ethyl acetate:acetic acid:water=3:1:1)

NMR (CD$_3$OD): δ 7.93-7.97 (m, 2H), 7.34-7.47 (m, 5H), 7.15-7.35 (m, 4H), 4.30-4.36 (m, 1H), 3.47 (dd, J=14.7, 5.1 Hz, 1H), 3.25 (dd, J=14.7, 8.4 Hz, 1H), 2.49 (s, 3H), 2.48 (s, 3H)

Reference Example 24

(2S)-2-Amino-3-(3,4-bis((4-hydroxybenzoyl)oxy)phenyl)propanoic acid hydrochloride

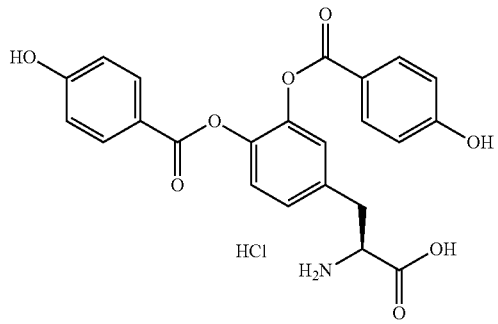 [SMILES: N[C@@H](Cc1ccc(OC(=O)c2ccc(O)cc2)c(OC(=O)c2ccc(O)cc2)c1)C(=O)O ; Cl]

By performing the procedure of Example 3→Example 4→Example 5 using the compound produced in Example 2 and 4-hydroxybenzoic acid in place of the compound produced in Example 1, the title compound having the following physical properties was obtained.

TLC (Rf value): 0.62 (ethyl acetate:acetic acid:water=3:1:1)

NMR (CD$_3$OD): δ 7.82-7.88 (m, 4H), 7.30-7.40 (m, 3H), 6.73-6.78 (m, 4H), 4.23 (dd, J=8.7, 4.8 Hz, 1H), 3.44 (dd, J=14.7, 4.8 Hz, 1H), 3.16 (dd, J=14.7, 8.7 Hz, 1H)

Reference Example 25

(2S)-2-Amino-3-(3,4-bis((2-(trifluoromethyl)benzoyl)oxy)phenyl)propanoic acid

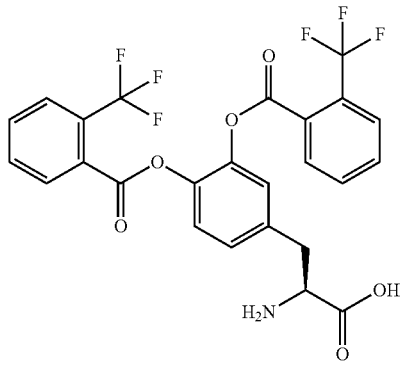 [SMILES: N[C@@H](Cc1ccc(OC(=O)c2ccccc2C(F)(F)F)c(OC(=O)c2ccccc2C(F)(F)F)c1)C(=O)O]

By performing the procedure of Example 3→Example 4→Example 5 using the compound produced in Example 2 and 2-trifluoromethylbenzoic acid in place of the compound produced in Example 1, the title compound having the following physical properties was obtained.

TLC (Rf value): 0.80 (ethyl acetate:acetic acid:water=3:1:1)

NMR (CD$_3$OD): δ 7.84-7.91 (m, 4H), 7.65-7.79 (m, 4H), 7.39-7.49 (m, 3H), 4.35 (dd, J=7.8, 5.1 Hz, 1H), 3.43 (dd, J=14.4, 5.1 Hz, 1H), 3.20-3.27 (m, 1H)

Reference Example 26

(2S)-2-Amino-3-(3,4-bis((cyclopropanecarbonyl)oxy)phenyl)propanoic acid hydrochloride

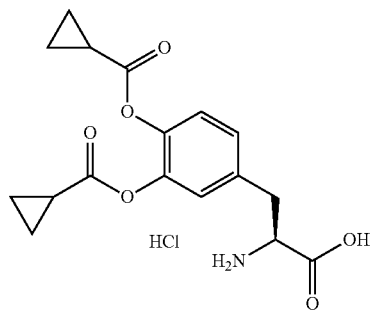 [SMILES: N[C@@H](Cc1ccc(OC(=O)C2CC2)c(OC(=O)C2CC2)c1)C(=O)O ; Cl]

By performing the procedure of Example 3→Example 4→Example 5 using the compound produced in Example 2 and cyclopropanecarboxylic acid in place of the compound produced in Example 1, the title compound having the following physical properties was obtained.

TLC (Rf value): 0.49 (ethyl acetate:acetic acid:water=3:1:1)

NMR (CD$_3$OD): δ 7.17-7.23 (m, 3H), 4.27 (dd, J=8.7, 5.1 Hz, 1H), 3.37 (dd, J=14.7, 5.1 Hz, 1H), 3.12 (dd, J=14.7, 8.7 Hz, 1H), 1.84-1.90 (m, 2H), 1.08-1.13 (m, 8H)

Reference Example 27

(2S)-2-Amino-3-(3,4-bis((1-methylcyclopropanecarbonyl)oxy)phenyl)propanoic acid hydrochloride

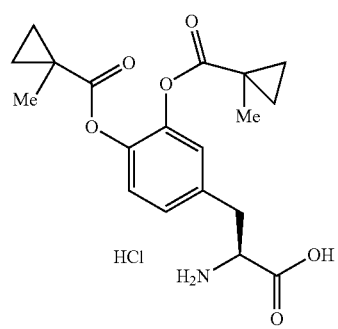 [SMILES: CC1(C(=O)Oc2ccc(C[C@H](N)C(=O)O)cc2OC(=O)C2(C)CC2)CC1 ; Cl]

By performing the procedure of Example 3→Example 4→Example 5 using the compound produced in Example 2 and 1-methylcyclopropanecarboxylic acid in place of the compound produced in Example 1, the title compound having the following physical properties was obtained.

TLC (Rf value): 0.23 (ethyl acetate:acetic acid:water=6:1:1)

NMR (CD$_3$OD): δ 7.15-7.25 (m, 3H), 4.26 (dd, J=8.4, 4.8 Hz, 1H), 3.35 (dd, J=14.7, 4.8 Hz, 1H), 3.12 (dd, J=14.7, 8.4 Hz, 1H), 1.33-1.46 (m, 10H), 0.93-0.97 (m, 4H)

Reference Example 28

(2S)-2-Amino-3-(3,4-bis(2-cyclopentylacetoxy)phenyl)propanoic acid hydrochloride

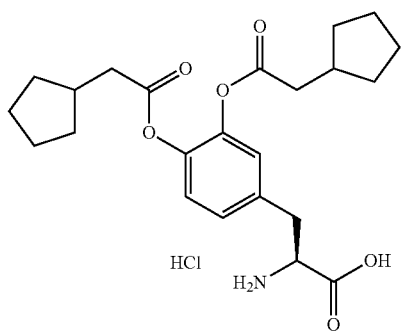 [SMILES: N[C@@H](Cc1ccc(OC(=O)CC2CCCC2)c(OC(=O)CC2CCCC2)c1)C(=O)O ; Cl]

By performing the procedure of Example 3→Example 4→Example 5 using the compound produced in Example 2 and 2-cyclopentylacetic acid in place of the compound produced in Example 1, the title compound having the following physical properties was obtained.

TLC (Rf value): 0.28 (ethyl acetate:acetic acid:water=6:1:1)

NMR (CD$_3$OD): δ 7.17-7.27 (m, 3H), 4.27 (dd, J=8.4, 5.1 Hz, 1H), 3.28 (dd, J=14.7, 5.1 Hz, 1H), 3.13 (dd, J=14.7, 8.4 Hz, 1H), 2.56-2.60 (m, 4H), 2.24-2.35 (m, 2H), 1.86-1.96 (m, 4H), 1.54-1.75 (m, 8H), 1.20-1.32 (m, 4H)

Reference Example 29

(2S)-2-Amino-3-(3,4-bis(2-cyclohexylacetoxy)phenyl)propanoic acid hydrochloride

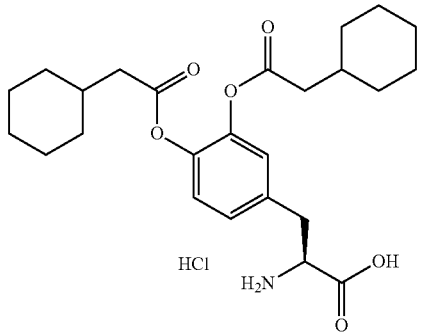 [SMILES: N[C@@H](Cc1ccc(OC(=O)CC2CCCCC2)c(OC(=O)CC2CCCCC2)c1)C(=O)O ; Cl]

By performing the procedure of Example 3→Example 4→Example 5 using the compound produced in Example 2 and 2-cyclohexylacetic acid in place of the compound produced in Example 1, the title compound having the following physical properties was obtained.

TLC (Rf value): 0.30 (ethyl acetate:acetic acid:water=6:1:1)

NMR (CD$_3$OD): δ 7.16-7.56 (m, 3H), 4.23 (dd, J=8.7, 5.1 Hz, 1H), 3.37 (dd, J=14.7, 5.1 Hz, 1H), 3.11 (dd, J=14.7, 8.4 Hz, 1H), 2.44 (d, J=6.6 Hz, 2H), 2.43 (d, J=6.6 Hz, 2H), 1.61-1.88 (m, 12H), 1.01-1.40 (m, 10H)

Reference Example 30

(2S)-2-Amino-3-(3,4-bis(2-(1-methylcyclohexyl)acetoxy)phenyl)propanoic acid hydrochloride

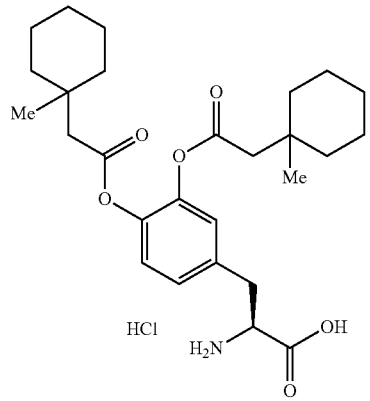 [SMILES: CC1(CC(=O)Oc2ccc(C[C@H](N)C(=O)O)cc2OC(=O)CC2(C)CCCCC2)CCCCC1 ; Cl]

By performing the procedure of Example 3→Example 4→Example 5 using the compound produced in Example 2 and 2-(1-methyl)cyclohexylacetic acid in place of the compound produced in Example 1, the title compound having the following physical properties was obtained.

TLC (Rf value): 0.43 (ethyl acetate:acetic acid=3:1)

NMR (CD$_3$OD): δ 7.21-7.31 (m, 3H), 4.28 (dd, J=8.4, 4.8 Hz, 1H), 3.30-3.46 (m, 1H), 3.17 (dd, J=14.4, 8.4 Hz, 1H), 2.56 (s, 2H), 2.55 (s, 2H), 1.49-1.70 (m, 20H), 1.18 (s, 3H), 1.17 (s, 3H)

Reference Example 31

(2S)-2-Amino-3-(3,4-bis(2-(1-methylcyclopentyl)acetoxy)phenyl)propanoic acid hydrochloride

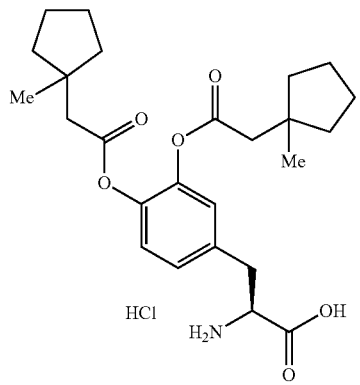 [SMILES: CC1(CC(=O)Oc2ccc(C[C@H](N)C(=O)O)cc2OC(=O)CC2(C)CCCC2)CCCC1 ; Cl]

By performing the procedure of Example 3→Example 4→Example 5 using the compound produced in Example 2 and 2-(1-methylcyclopentyl)acetic acid in place of the compound produced in Example 1, the title compound having the following physical properties was obtained.

TLC (Rf value): 0.29 (ethyl acetate:acetic acid=3:1)

NMR (CD₃OD): δ 7.16-7.26 (m, 3H), 4.16 (dd, J=8.7, 4.8 Hz, 1H), 3.22-3.40 (m, 1H), 3.05-3.13 (m, 1H), 2.56 (s, 2H), 2.57 (s, 2H), 1.50-1.73 (m, 16H), 1.16 (s, 3H), 1.15 (s, 3H)

Reference Example 32

(2S)-2-Amino-3-(3,4-bis((2-acetoxy-2-methylpropanoyl)oxy)phenyl)propanoic acid hydrochloride

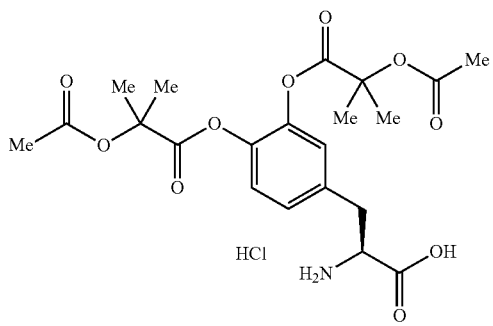 [SMILES: CC(=O)OC(C)(C)C(=O)Oc1ccc(C[C@H](N)C(=O)O)cc1OC(=O)C(C)(C)OC(C)=O ; Cl]

By performing the procedure of Example 3→Example 4→Example 5 using the compound produced in Example 2 and 2-(acetoxy)-2-methylpropionic acid in place of the compound produced in Example 1, the title compound having the following physical properties was obtained.

TLC (Rf value): 0.70 (ethyl acetate:acetic acid:water=3:1:1)

NMR (CD₃OD): δ 7.18-7.27 (m, 3H), 4.25 (dd, J=8.4, 5.4 Hz, 1H), 3.37 (dd, J=14.7, 5.4 Hz, 1H), 3.13 (dd, J=14.7, 8.4 Hz, 1H), 2.09 (s, 3H), 2.07 (s, 3H), 1.66-1.68 (m, 12H)

Reference Example 33

(2S)-2-Amino-3-(3,4-bis((2-(benzoyloxy)-2-ethylbutanoyl)oxy)phenyl)propanoic acid hydrochloride

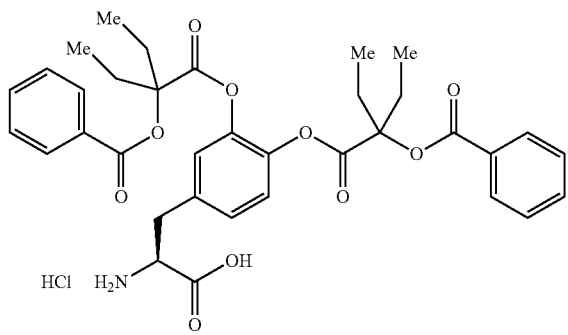 [SMILES: CCC(CC)(OC(=O)c1ccccc1)C(=O)Oc1ccc(C[C@H](N)C(=O)O)cc1OC(=O)C(CC)(CC)OC(=O)c1ccccc1 ; Cl]

By performing the procedure of Example 3→Example 4→Example 5 using the compound produced in Example 2 and 2-(benzoyloxy)-2-ethylbutanoic acid in place of the compound produced in Example 1, the title compound having the following physical properties was obtained.

TLC (Rf value): 0.51 (ethyl acetate:acetic acid:water=5:1:1)

NMR (CD₃OD): δ 8.01-8.06 (m, 4H), 7.61-7.64 (m, 2H), 7.49-7.52 (m, 4H), 7.25-7.47 (m, 3H), 4.22 (dd, J=8.4, 5.1 Hz, 1H), 3.32-3.35 (m, 1H), 3.05-3.16 (m, 1H), 2.20-2.37 (m, 8H), 0.97-1.03 (m, 12H)

Reference Example 34

(2S)-2-Amino-3-(3,4-bis(((S)-2-(benzoyloxy)propanoyl)oxy)phenyl)propanoic acid hydrochloride

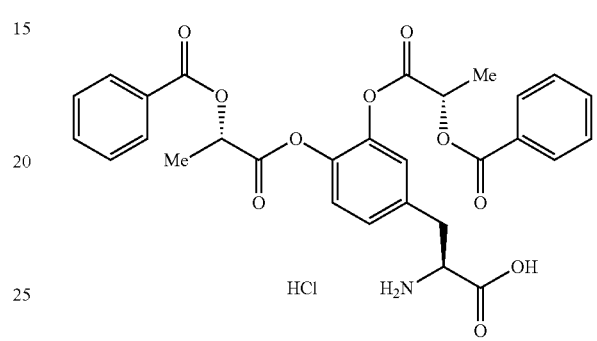

By performing the procedure of Example 3→Example 4→Example 5 using the compound produced in Example 2 and (2S)-2-(benzoyloxy)propanoic acid in place of the compound produced in Example 1, the title compound having the following physical properties was obtained.

TLC (Rf value): 0.38 (ethyl acetate:acetic acid:water=10:2:1)

NMR (CD₃OD): δ 8.06-8.09 (m, 4H), 7.61-7.66 (m, 2H), 7.46-7.52 (m, 4H), 7.26-7.29 (m, 3H), 5.61-5.68 (m, 2H), 4.21 (dd, J=8.4, 5.4 Hz, 1H), 3.30-3.40 (m, 1H), 3.13 (dd, J=14.7, 8.1 Hz, 1H), 1.81 (d, J=7.2 Hz, 3H), 1.80 (d, J=7.2 Hz, 3H)

Reference Example 35

(2S)-2-Amino-3-(3,4-bis(((R)-2-(benzoyloxy)propanoyl)oxy)phenyl)propanoic acid hydrochloride

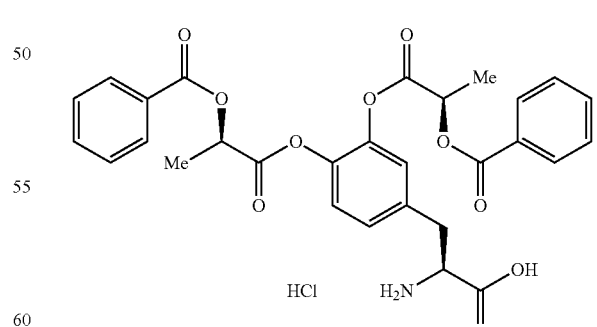

By performing the procedure of Example 3→Example 4→Example 5 using the compound produced in Example 2 and (2R)-2-(benzoyloxy)propanoic acid in place of the compound produced in Example 1, the title compound having the following physical properties was obtained.

TLC (Rf value): 0.38 (ethyl acetate:acetic acid:water=10:2:1)

NMR (CD$_3$OD): δ 8.06-8.09 (m, 4H), 7.61-7.66 (m, 2H), 7.46-7.52 (m, 4H), 7.26-7.29 (m, 3H), 5.61-5.68 (m, 2H), 4.21 (dd, J=8.4, 5.4 Hz, 1H), 3.30-3.40 (m, 1H), 3.13 (dd, J=14.7, 8.1 Hz, 1H), 1.81 (d, J=7.2 Hz, 3H), 1.80 (d, J=7.2 Hz, 3H)

Reference Example 36

3-(Benzyloxy)-2,2-dimethyl-3-oxopropyl benzoate

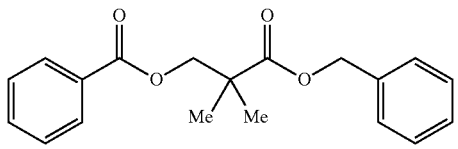 [SMILES: CC(C)(COC(=O)c1ccccc1)C(=O)OCc1ccccc1]

The compound (8 g) produced in Reference Example 1 was dissolved in dichloromethane (40 mL). To this solution, triethylamine (8 mL) was added, and then, benzoyl chloride (5.4 mL) was added thereto under ice-cooling. The resulting solution was stirred at room temperature for 4 hours. To the reaction mixture, a saturated aqueous solution of sodium carbonate (30 mL) was added, and then, extraction was performed with dichloromethane (100 mL×2). The organic layers were combined, and washed with a saturated aqueous solution of sodium chloride (30 mL), and then dried over sodium sulfate. After sodium sulfate was removed by filtration, the solvent was concentrated under reduced pressure. The resulting residue was purified by silica gel chromatography (a medium-pressure preparative liquid chromatograph, W-prep 2XY manufactured by Yamazen Corporation (column: main column 2L, inject column L, n-hexane:ethyl acetate=1:0-9:1 (gradient time: 10 minutes), fractionation mode GR), whereby the title compound (12 g, 100%) having the following physical properties was obtained.

TLC (Rf value): 0.70 (n-hexane:ethyl acetate=2:1)

NMR (300 MHz, CDCl$_3$): δ 7.89-7.93 (m, 2H), 7.50-7.57 (m, 1H), 7.36-7.42 (m, 2H), 7.23-7.33 (m, 5H), 5.16 (s, 2H), 4.37 (s, 2H), 1.34 (s, 6H)

Reference Example 37

3-(Benzoyloxy)-2,2-dimethylpropanoic acid

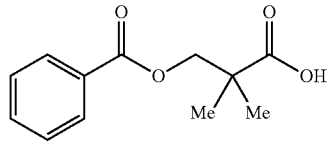 [SMILES: CC(C)(COC(=O)c1ccccc1)C(=O)O]

By performing the same procedure as in Reference Example 3 using the compound (12 g) produced in Reference Example 36 in place of the compound produced in Reference Example 2, the title compound (5.7 g, 67%) having the following physical properties was obtained.

TLC (Rf value): 0.22 (n-hexane:ethyl acetate=3:1)

NMR (CDCl$_3$): δ 7.99-8.03 (m, 2H), 7.48-7.61 (m, 1H), 7.38-7.46 (m, 2H), 4.37 (s, 2H), 1.35 (s, 6H)

Reference Example 38

(S)-((4-(3-(Benzyloxy)-2-((tert-butoxycarbonyl)amino)-3-oxopropyl)-1,2-phenylene)bis(oxy))bis(2,2-dimethyl-3-oxopropan-3,1-diyl)dibenzoate

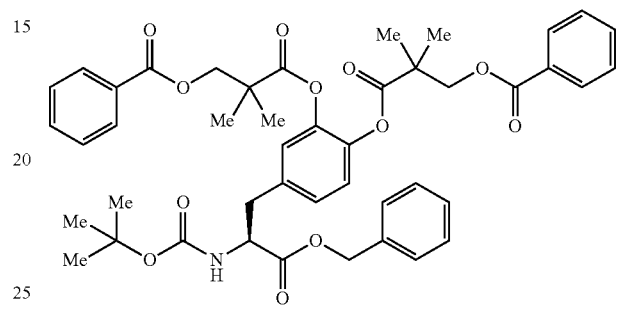

By performing the same procedure as in Example 3 using the compound (4.0 g) produced in Example 2 and the compound (5.7 g) produced in Reference Example 37 in place of the compound produced in Example 1, the title compound (7.4 g, 90%) having the following physical properties was obtained.

TLC (Rf value): 0.51 (n-hexane:ethyl acetate=2:1)

NMR (CDCl$_3$): δ 8.00-8.05 (m, 4H), 7.50-7.59 (m, 2H), 7.39-7.46 (m, 4H), 7.23-7.34 (m, 5H), 6.83-6.97 (m, 3H), 5.09 (s, 2H), 4.97 (d, J=8.4 Hz, 1H), 4.50-4.57 (m, 1H), 4.45 (s, 4H), 2.94-3.03 (m, 2H), 1.39-1.43 (m, 21H)

Reference Example 39

(S)-3-(3,4-Bis((3-(benzoyloxy)-2,2-dimethylpropanoyl)oxy)phenyl)-2-((tert-butoxycarbonyl)amino)propanoic acid

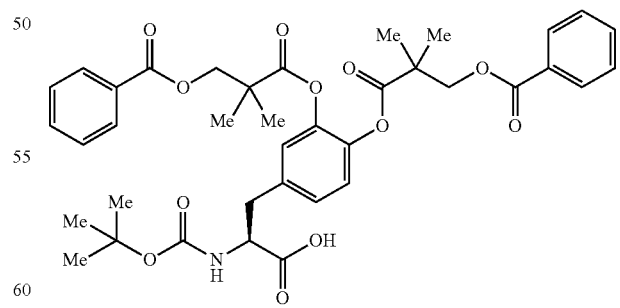

By performing the same procedure as in Example 4 using the compound (7.4 g) produced in Reference Example 38 in place of the compound produced in Example 3, the title compound (5.2 g, 79%) having the following physical properties was obtained.

TLC (Rf value): 0.12 (n-hexane:ethyl acetate=2:1)

NMR (CDCl₃): δ 8.00-8.04 (m, 4H), 7.54-7.61 (m, 2H), 7.41-7.48 (m, 4H), 6.97-7.05 (m, 2H), 6.91 (d, J=1.8 Hz, 1H), 4.99 (d, J=7.5 Hz, 1H), 4.42-4.50 (m, 5H), 2.98-3.11 (m, 2H), 1.40-1.42 (m, 21H)

Reference Example 40

(S)-2-Amino-3-(3,4-bis((3-(benzoyloxy)-2,2-dimethylpropanoyl)oxy)phenyl)propanoic acid hydrochloride

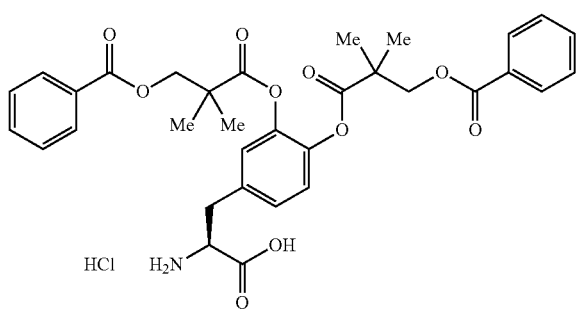 [SMILES: CC(C)(COC(=O)c1ccccc1)C(=O)Oc1ccc(C[C@H](N)C(=O)O)cc1OC(=O)C(C)(C)COC(=O)c1ccccc1 ; Cl]

By performing the same procedure as in Example 5 using the compound (5.2 g) produced in Reference Example 39 in place of the compound produced in Example 4, the title compound (4.3 g, 88%) having the following physical properties was obtained.

TLC (Rf value): 0.34 (ethyl acetate:acetic acid:water=6:1:1)

NMR (CD₃OD): δ 7.97-8.02 (m, 4H), 7.57-7.63 (m, 2H), 7.43-7.51 (m, 4H), 7.12-7.18 (m, 3H), 4.54-4.66 (m, 4H), 4.09 (dd, J=8.7, 4.8 Hz, 1H), 3.06-3.25 (m, 1H), 2.99-3.07 (m, 1H), 1.43-1.44 (m, 12H)

Example 6

Crystalline (2S)-2-amino-3-(3,4-bis((2-(benzoyloxy)-2-methylpropanoyl)oxy)phenyl)propanoic acid tosylate (Type A crystal)

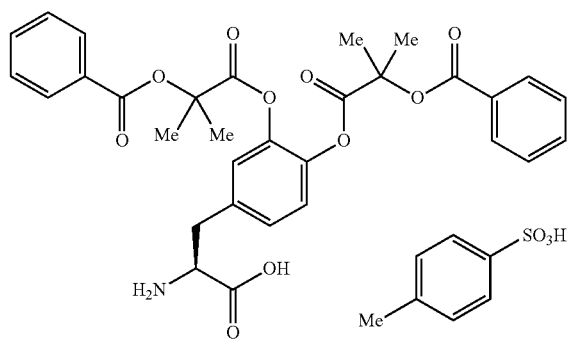 [SMILES: CC(C)(OC(=O)c1ccccc1)C(=O)Oc1ccc(C[C@H](N)C(=O)O)cc1OC(=O)C(C)(C)OC(=O)c1ccccc1 ; Cc1ccc(S(=O)(=O)O)cc1]

To a suspension of p-toluenesulfonic acid monohydrate (2.82 g) in acetonitrile (4.2 mL) and water (1.13 mL), a solution of the compound (8.32 g) produced in Example 4 in acetonitrile (37.8 mL) was added. This solution was stirred at 70° C. for 2 hours. After the reaction mixture was cooled to room temperature, tert-butylmethyl ether (254 mL) was added thereto. This solution was stirred overnight at room temperature. After the solution was further stirred under ice-cooling for 1 hour, a crystal was obtained by filtration, followed by drying under reduced pressure at 50° C. for 16 hours, whereby a crystalline solvate of (2S)-2-amino-3-(3,4-bis((2-(benzoyloxy)-2-methylpropanoyl)oxy)phenyl)propanoic acid tosylate (7.43 g, 79%) was obtained. The total amount of this crystal was suspended in ethyl acetate (74 mL) and the resulting suspension was stirred at 60° C. for 14 hours while maintaining the suspended state. After the suspension was left to cool to room temperature, the crystal was obtained by filtration, followed by drying under reduced pressure at 65° C. for 1 hour and thereafter at 50° C. for 16 hours, whereby a type A crystal of the title compound (6.87 g, 92%) having the following physical properties was obtained as a white crystal. The crystal had a melting point of from about 132.0 to 136.0° C. (measured by the capillary method described in the Japanese Pharmacopoeia).

TLC (Rf value): 0.56 (ethyl acetate:acetic acid:water=10:1:1)

NMR (300 MHz, CD₃OD): δ 8.06-8.03 (m, 4H), 7.71-7.62 (m, 4H), 7.52-7.48 (m, 4H), 7.31-7.20 (m, 5H), 4.27 (dd, J=8.4, 5.1 Hz, 1H), 3.37 (dd, J=14.7, 5.1 Hz, 1H), 3.13 (dd, J=14.7, 8.4 Hz, 1H), 2.36 (s, 3H), 1.83 (s, 12H)

The powder X-ray diffraction spectrum chart, differential scanning calorimetry chart, and infrared absorption spectrum chart of the thus obtained type A crystal of (2S)-2-amino-3-(3,4-bis((2-(benzoyloxy)-2-methylpropanoyl)oxy)phenyl)propanoic acid tosylate are shown in FIG. 10, FIG. 11, and FIG. 12, respectively.

(1) Powder X-Ray Diffraction Spectroscopy

[Measurement Conditions]

Apparatus: BRUKER DISCOVER with GADDS (C2)
Target: Cu
Filter: Not used
Voltage: 40 kV
Current: 40 mA
Exposure time: 180 sec

[Results]

The results of diffraction angle (2θ) (degrees) and relative intensity (%) obtained by the powder X-ray diffraction spectroscopy using Cu—Kα radiation are shown in Table 1. Incidentally, the relative intensity is obtained by calculating the height (Lin (Counts)) of each peak when the height of the highest peak is taken as 100%.

TABLE 1

| Diffraction angle (2θ) (degrees) | Relative intensity (%) |
| --- | --- |
| 5.15 | 100 |
| 6.97 | 95.0 |
| 7.46 | 11.3 |
| 10.97 | 17.9 |
| 11.58 | 50.9 |
| 13.74 | 8.5 |
| 14.83 | 30.4 |
| 15.20 | 17.0 |
| 16.10 | 21.8 |
| 16.36 | 26.5 |
| 16.70 | 15.3 |
| 17.35 | 15.7 |
| 18.30 | 18.2 |
| 18.83 | 13.8 |
| 19.42 | 28.2 |
| 19.95 | 20.4 |
| 20.58 | 28.6 |
| 21.69 | 24.1 |
| 22.63 | 13.0 |

TABLE 1-continued

| Diffraction angle (2θ) (degrees) | Relative intensity (%) |
|---|---|
| 22.84 | 12.4 |
| 24.00 | 17.4 |

(2) Differential Scanning calorimetry
[Measurement Conditions]
Apparatus: SEIKO INSTRUMENT DSC 6200
Amount of sample: 4.22 mg
Sample cell: Aluminum Standard 40 μL (having a lid with a pinhole)
Argon gas flow rate: 40 mL/min
Temperature elevation rate: 5° C./min
Temperature elevation starting temperature: 25° C.
[Results]
As a result, it was found that the compound has an endothermic peak at around 135.95° C.
(3) Infrared Absorption Spectroscopy
[Measurement Conditions]
Apparatus: FTIR-660 Plus/SENSIR DuraScope, JASCO Corporation
Resolution: 4 cm$^{-1}$
Number of scanning times: 32
[Results]
IR (ATR method): 1780, 1712, 1599, 1508, 1452, 1388, 1316, 1289, 1217, 1166, 1120, 1090, 1071, 1036, 1026, 1010, 957, 900, 864, 817, 742, 713, 680, 622, 567, 550, 472, and 440 cm$^{-1}$ Example 7

Crystalline (2S)-2-amino-3-(3,4-bis((2-(benzoyloxy)-2-methylpropanoyl)oxy)phenyl)propanoic acid tosylate (Type B crystal)

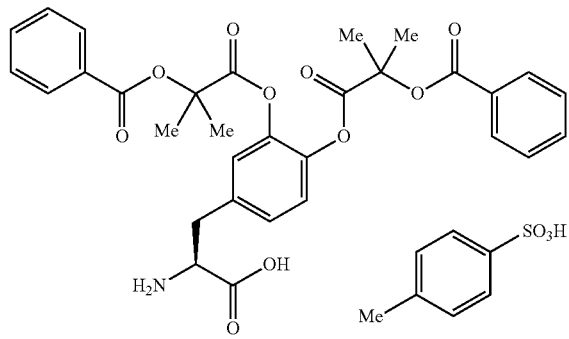 [SMILES: CC(C)(OC(=O)c1ccccc1)C(=O)Oc1ccc(C[C@H](N)C(=O)O)cc1OC(=O)C(C)(C)OC(=O)c1ccccc1 ; Cc1ccc(S(=O)(=O)O)cc1]

The type A crystal of (2S)-2-amino-3-(3,4-bis((2-(benzoyloxy)-2-methylpropanoyl)oxy)phenyl)propanoic acid tosylate (8.0 g) produced in Example 6 was suspended in acetone (80 mL). This suspension was stirred at 50° C. for 16 hours. After the reaction mixture was cooled to room temperature, the mixture was stirred for 30 minutes, and then, further stirred in an ice bath for 1 hour. A deposited crystal was obtained by filtration, followed by drying under reduced pressure at 60° C. for 16 hours, whereby a type B crystal of the title compound (7.1 g, 89%) was obtained as a white crystal. The crystal had a melting point of from about 132.3 to 135.3° C. (measured by the capillary method described in the Japanese Pharmacopoeia).

The powder X-ray diffraction spectrum chart, differential scanning calorimetry chart, and infrared absorption spectrum chart of the thus obtained type B crystal of (2S)-2-amino-3-(3,4-bis((2-(benzoyloxy)-2-methylpropanoyl)oxy)phenyl)propanoic acid tosylate are shown in FIG. 13, FIG. 14, and FIG. 15, respectively.
(1) Powder X-Ray Diffraction Spectroscopy
[Measurement Conditions]
Apparatus: BRUKER DISCOVER with GADDS (C2)
Target: Cu
Filter: Not used
Voltage: 40 kV
Current: 40 mA
Exposure time: 180 sec
[Results]
The results of diffraction angle (2θ) (degrees) and relative intensity (%) obtained by the powder X-ray diffraction spectroscopy using Cu—Kα radiation are shown in Table 2. Incidentally, the relative intensity is obtained by calculating the height (Lin (Counts)) of each peak when the height of the highest peak is taken as 100%.

TABLE 2

| Diffraction angle (2θ) (degrees) | Relative intensity (%) |
|---|---|
| 4.04 | 32.9 |
| 5.04 | 63.9 |
| 5.54 | 24.6 |
| 6.11 | 100 |
| 6.60 | 68.4 |
| 7.96 | 42.0 |
| 8.62 | 16.0 |
| 10.01 | 39.2 |
| 10.32 | 18.6 |
| 11.88 | 54.2 |
| 12.88 | 15.6 |
| 13.87 | 25.1 |
| 15.01 | 20.0 |
| 15.87 | 24.5 |
| 16.07 | 26.7 |
| 16.74 | 14.1 |
| 17.17 | 15.1 |
| 17.81 | 24.7 |
| 18.65 | 39.8 |
| 19.17 | 34.2 |
| 19.72 | 21.6 |
| 20.27 | 35.1 |
| 20.93 | 16.9 |
| 21.67 | 16.7 |
| 22.11 | 37.0 |
| 22.56 | 14.3 |
| 23.11 | 17.0 |
| 23.47 | 20.2 |
| 24.21 | 20.4 |

(2) Differential Scanning Calorimetry
[Measurement Conditions]
Apparatus: SEIKO INSTRUMENT DSC 6200
Amount of sample: 3.08 mg
Sample cell: Aluminum Standard 40 μL (having a lid with a pinhole)
Argon gas flow rate: 40 mL/min
Temperature elevation rate: 5° C./min
Temperature elevation starting temperature: 25° C.
[Results]
As a result, it was found that the compound has an endothermic peak at around 134.54° C.

(3) Infrared Absorption Spectroscopy
[Measurement Conditions]
Apparatus: FTIR-660 Plus/SENSIR DuraScope, JASCO Corporation
Resolution: 4 cm$^{-1}$
Number of scanning times: 32
[Results]
IR (ATR method): 1781, 1711, 1600, 1507, 1315, 1287, 1220, 1203, 1166, 1119, 1088, 1070, 1036, 1027, 1010, 944, 898, 863, 816, 713, 681, 617, 567, 531, 517, 507, 484, 470, 452, 437, 421, and 413 cm$^{-1}$

Example 8

Crude (2S)-2-amino-3-(3,4-bis((2-(benzoyloxy)-2-methylpropanoyl)oxy)phenyl)propanoic acid

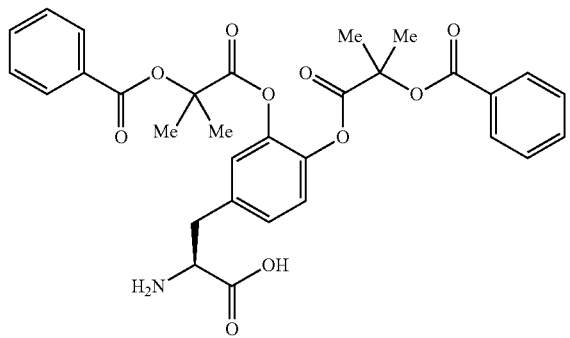 [SMILES: CC(C)(OC(=O)c1ccccc1)C(=O)Oc1ccc(C[C@H](N)C(=O)O)cc1OC(=O)C(C)(C)OC(=O)c1ccccc1]

To a solution of the type A crystal of (2S)-2-amino-3-(3,4-bis((2-(benzoyloxy)-2-methylpropanoyl)oxy)phenyl)propanoic acid tosylate produced in Example 6 or the type B crystal of (2S)-2-amino-3-(3,4-bis((2-(benzoyloxy)-2-methylpropanoyl)oxy)phenyl)propanoic acid tosylate produced in Example 7 (167 g) in acetonitrile (2080 mL) and water (42 mL), a solution of triethylamine (21.4 g) in acetonitrile (420 mL) was added dropwise. After the reaction mixture was stirred for 16 hours, a deposited solid was obtained by filtration and washed with acetonitrile (500 mL). Then, the solid was dried at 50° C. for 16 hours, whereby a crude product of the title compound (106 g, 81%) was obtained as a white solid.

Example 9

Crystalline (2S)-2-amino-3-(3,4-bis((2-(benzoyloxy)-2-methylpropanoyl)oxy)phenyl)propanoic acid (Type A crystal)

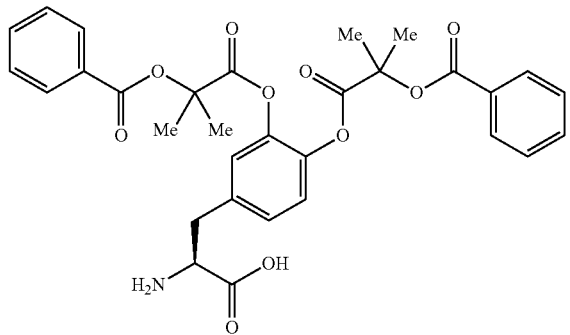 [SMILES: CC(C)(OC(=O)c1ccccc1)C(=O)Oc1ccc(C[C@H](N)C(=O)O)cc1OC(=O)C(C)(C)OC(=O)c1ccccc1]

The crude (2S)-2-amino-3-(3,4-bis((2-(benzoyloxy)-2-methylpropanoyl)oxy)phenyl)propanoic acid (31 g) produced in Example 8 was suspended in acetonitrile (470 mL) in an argon atmosphere, and the resulting suspension was stirred at room temperature (internal temperature: from 23 to 24° C.) for 24 hours. The resulting crystal was obtained by filtration and washed with acetonitrile (94 mL). Then, the crystal was dried under reduced pressure at 60° C. for 24 hours, whereby a type A crystal of the title compound (31 g, 99%) was obtained as a white crystal. The crystal had a melting point of from about 177.0 to 181.9° C. (measured by the capillary method described in the Japanese Pharmacopoeia).

The powder X-ray diffraction spectrum chart, differential scanning calorimetry chart, and infrared absorption spectrum chart of the thus obtained type A crystal of (2S)-2-amino-3-(3,4-bis((2-(benzoyloxy)-2-methylpropanoyl)oxy)phenyl)propanoic acid are shown in FIG. 4, FIG. 5, and FIG. 6, respectively.

(1) Powder X-Ray Diffraction Spectroscopy
[Measurement Conditions]
Apparatus: BRUKER DISCOVER with GADDS (C2)
Target: Cu
Filter: Not used
Voltage: 40 kV
Current: 40 mA
Exposure time: 180 sec
[Results]
The results of diffraction angle (2θ) (degrees) and relative intensity (%) obtained by the powder X-ray diffraction spectroscopy using Cu—Kα radiation are shown in Table 3. Incidentally, the relative intensity is obtained by calculating the height (Lin (Counts)) of each peak when the height of the highest peak is taken as 100%.

TABLE 3

| Diffraction angle (2θ) (degrees) | Relative intensity (%) |
| --- | --- |
| 4.03 | 100 |
| 7.21 | 15.3 |
| 9.98 | 10.7 |
| 10.72 | 10.6 |
| 11.93 | 12.5 |
| 12.90 | 10.5 |
| 13.48 | 11.9 |
| 14.65 | 12.3 |
| 15.23 | 12.7 |
| 15.99 | 15.2 |
| 16.56 | 13.6 |
| 17.23 | 14.6 |
| 17.93 | 19.3 |
| 19.20 | 18.8 |
| 20.88 | 12.4 |
| 21.66 | 12.2 |
| 22.36 | 11.7 |
| 22.50 | 10.8 |
| 24.58 | 8.7 |

(2) Differential Scanning Calorimetry
[Measurement Conditions]
Apparatus: SEIKO INSTRUMENT DSC 6200
Amount of sample: 6.07 mg
Sample cell: Aluminum Standard 40 μL (having a lid with a pinhole)
Argon gas flow rate: 40 mL/min
Temperature elevation rate: 10° C./min Temperature elevation starting temperature: 25° C.
[Results]
As a result, it was found that the compound has an exothermic peak at around 148.7° C. and also has endothermic peaks at around 184.7° C., 194.7° C., and 200.3° C.

(3) Infrared Absorption Spectroscopy
[Measurement Conditions]
Apparatus: FTIR-660 Plus/SENSIR DuraScope, JASCO Corporation
Resolution: 4 cm$^{-1}$
Number of scanning times: 32
[Results]
IR (ATR method): 1771, 1720, 1632, 1602, 1543, 1506, 1469, 1451, 1387, 1359, 1316, 1287, 1203, 1165, 1093, 1069, 1026, 957, 937, 898, 863, 802, 742, 710, 687, 615, 557, 526, 490, 482, 452, 424, 416, and 408 cm$^{-1}$ Example 10

Crystalline (2S)-2-amino-3-(3,4-bis((2-(benzoyloxy)-2-methylpropanoyl)oxy)phenyl)propanoic acid (Type B Crystal)

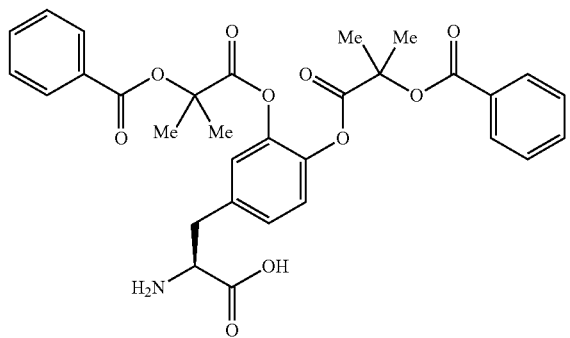 [SMILES: CC(C)(OC(=O)c1ccccc1)C(=O)Oc1ccc(C[C@H](N)C(=O)O)cc1OC(=O)C(C)(C)OC(=O)c1ccccc1]

The crude (2S)-2-amino-3-(3,4-bis((2-(benzoyloxy)-2-methylpropanoyl)oxy)phenyl)propanoic acid (104 g) produced in Example 8 was dissolved in acetonitrile (520 mL) and water (104 mL) by heating under an argon atmosphere. Then, acetonitrile (1560 mL) was added thereto, and after the deposition of a crystal was confirmed, the reaction mixture was stirred for 16 hours. The deposited crystal was obtained by filtration and then washed with acetonitrile (312 mL). Then, the crystal was dried under reduced pressure at 60° C. for 24 hours, whereby a type B crystal of the title compound (87 g, 84%) was obtained as a white crystal. The crystal had a melting point of from about 174.7 to 179.0° C. (measured by the capillary method described in the Japanese Pharmacopoeia).

Figure 7:
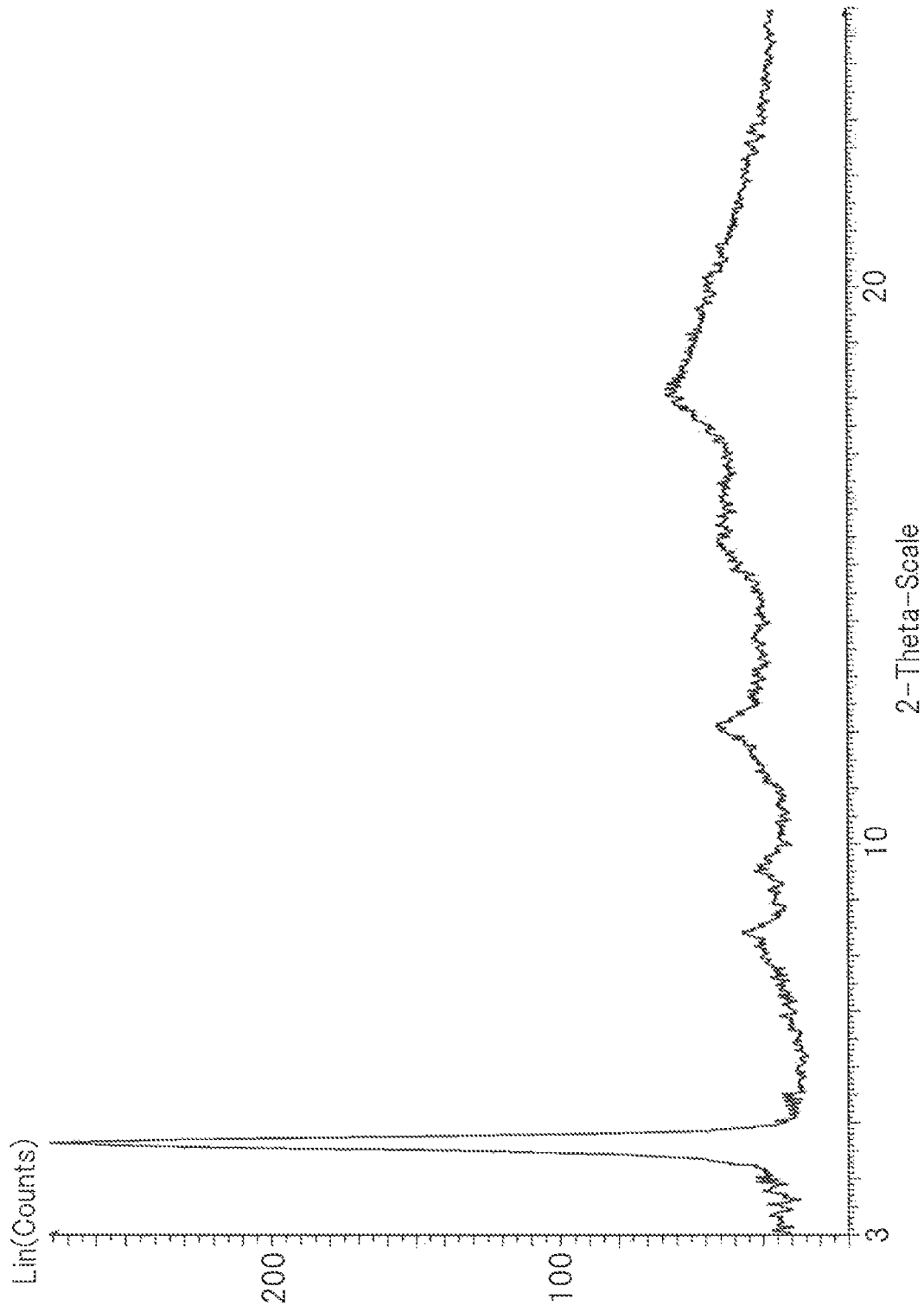
FIG. 7 shows a powder X-ray diffraction spectrum chart of crystalline (2S)-2-amino-3-(3,4-bis((2-(benzoyloxy)-2-methylpropanoyl)oxy)phenyl)propanoic acid (type B crystal) obtained in Example 10.

The powder X-ray diffraction spectrum chart, differential scanning calorimetry chart, and infrared absorption spectrum chart of the thus obtained type B crystal of (2S)-2-amino-3-(3,4-bis((2-(benzoyloxy)-2-methylpropanoyl)oxy)phenyl) propanoic acid are shown in FIG. 7, FIG. 8, and FIG. 9, respectively.

(1) Powder X-Ray Diffraction Spectroscopy
[Measurement Conditions]
Apparatus: BRUKER DISCOVER with GADDS (C2)
Target: Cu
Filter: Not used
Voltage: 40 kV
Current: 40 mA
Exposure time: 180 sec
[Results]
The results of diffraction angle (2θ) (degrees) and relative intensity (%) obtained by the powder X-ray diffraction spectroscopy using Cu—Kα radiation are shown in Table 4. Incidentally, the relative intensity is obtained by calculating the height (Lin (Counts)) of each peak when the height of the highest peak is taken as 100%.

TABLE 4

| Diffraction angle (2θ) (degrees) | Relative intensity (%) |
|---|---|
| 4.62 | 100 |
| 8.40 | 13.3 |
| 9.54 | 11.2 |
| 12.08 | 16.5 |
| 15.38 | 16.3 |
| 18.16 | 22.7 |

(2) Differential Scanning calorimetry
[Measurement Conditions]
Apparatus: SEIKO INSTRUMENT DSC 6200
Amount of sample: 5.68 mg
Sample cell: Aluminum Standard 40 μL (having a lid with a pinhole)
Argon gas flow rate: 40 mL/min
Temperature elevation rate: 10° C./min
Temperature elevation starting temperature: 25° C.
[Results]
As a result, it was found that the compound has an exothermic peak at around 183.3° C. and also has endothermic peaks at around 192.2° C. and 200.8° C.

(3) Infrared Absorption Spectroscopy
[Measurement Conditions]
Apparatus: FTIR-660 Plus/SENSIR DuraScope, JASCO Corporation
Resolution: 4 cm$^{-1}$
Number of scanning times: 32
[Results]
IR (ATR method): 1771, 1715, 1608, 1505, 1469, 1452, 1411, 1386, 1368, 1352, 1315, 1288, 1256, 1201, 1166, 1092, 1070, 1026, 955, 895, 865, 803, 744, 711, 675, 617, 605, 472, 444, 432, and 414 cm$^{-1}$ Example 11

Crystalline (2S)-2-amino-3-(3,4-bis((2-(benzoyloxy)-2-methylpropanoyl)oxy)phenyl)propanoic acid (Type A Crystal)

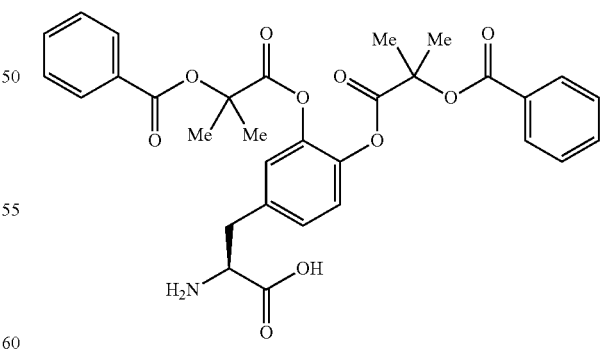

By performing the same procedure as in Example 9 using the type B crystal of (2S)-2-amino-3-(3,4-bis((2-(benzoyloxy)-2-methylpropanoyl)oxy)phenyl)propanoic acid produced in Example 10 in place of the crude (2S)-2-amino-3-(3,4-bis((2-(benzoyloxy)-2-methylpropanoyl)oxy)phenyl) propanoic acid, the crystal was converted into a type A crystal of (2S)-2-amino-3-(3,4-bis((2-(benzoyloxy)-2-methylpropanoyl)oxy)phenyl)propanoic acid.

Example 12

Crystalline (2S)-2-amino-3-(3,4-bis((2-(benzoyloxy)-2-methylpropanoyl)oxy)phenyl)propanoic acid (Type B Crystal)

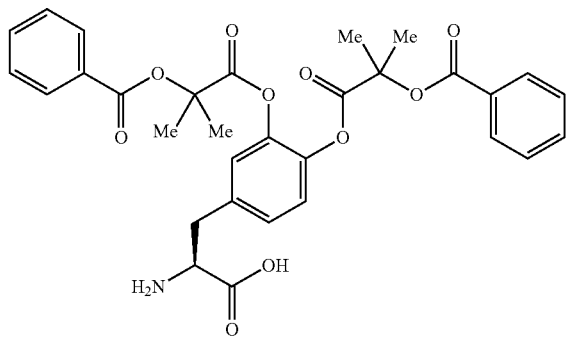 [SMILES: CC(C)(OC(=O)c1ccccc1)C(=O)Oc1ccc(C[C@H](N)C(=O)O)cc1OC(=O)C(C)(C)OC(=O)c1ccccc1]

By performing the same procedure as in Example 10 using the type A crystal of (2S)-2-amino-3-(3,4-bis((2-(benzoyloxy)-2-methylpropanoyl)oxy)phenyl)propanoic acid produced in Example 9 in place of the crude (2S)-2-amino-3-(3,4-bis((2-(benzoyloxy)-2-methylpropanoyl)oxy)phenyl) propanoic acid, the crystal was converted into a type B crystal of (2S)-2-amino-3-(3,4-bis((2-(benzoyloxy)-2-methylpropanoyl)oxy)phenyl)propanoic acid.

Biological Example 1

(1) Kinetic Study in Dogs

The relationship between the blood concentration of levodopa and side effects in patients who take levodopa has been gradually elucidated. For example, it is considered that dyskinesia is developed by the frequent exposure to levodopa at a concentration exceeding the effective blood concentration, and wearing-off is developed by levodopa at a concentration lower than the effective blood concentration. In order to reduce the number of doses of levodopa and avoid side effects such as dyskinesia and wearing-off in patients who take levodopa, it is necessary to maintain the blood concentration of levodopa within a therapeutic range as long as possible. The inventors of the present invention carried out a kinetic study for each of the compound of the present invention produced in Example 5, levodopa, and a group of compounds to be used for comparison (compounds produced in Reference Examples 6, 11, 16, 18, 19, 21 to 23, 25 to 35, and 40, and 3,3-dimethyl-butyric acid 4-((S)-2-amino-2-methoxycarbonyl-ethyl)-2-(3,3-dimethyl-butyryloxy)phenyl ester (hereinafter referred to as Compound X) described in WO 2009/022098) for the purpose of elucidating that the compound of the present invention is a levodopa prodrug which provides such a flat blood concentration-time profile of levodopa.

These levodopa prodrugs are prodrugs containing an ester bond, and therefore, it is considered that among a number of enzymes, carboxyesterase plays the most important role in the process of producing levodopa by metabolizing the compound after the compound is administered in vivo. Therefore, as an animal species to be used for performing a kinetic study, dogs in which the organ distribution of carboxyesterase is most similar to that of humans were selected as subjects for evaluation.

[Preparation of Drug Solution for Administration]

A drug solution for oral administration was prepared by weighing each of the compound of the present invention (Example 5), levodopa, a group of compounds to be used for comparison (compounds produced in Reference Examples 6, 11, 16, 18, 19, 21 to 23, 25 to 35, and 40, and Compound X) and dissolving it in a vehicle at 1 mg/mL expressed in terms of levodopa.

[Collection of Plasma Sample]

The thus obtained drug solution was administered by gavage through a gastric tube into the stomach of dogs (male beagle dogs) which were fasted from the day before the administration. At 15 and 30 minutes, and 1, 2, 4, 6, and 8 hours after administration of the drug solution, 1 mL of blood was collected from a cephalic vein with a heparinized syringe. Immediately after the collection, the collected blood was centrifuged in a desktop centrifuge at 14500 rpm for 45 seconds. Then, acetonitrile containing 0.1125% formic acid was added to the thus obtained plasma in an amount as twice as large as the volume of the plasma, followed by stirring, and then, the resulting sample was stored at −20° C. until measurement.

[Preparation of Analytical Sample and Analysis]

The sample was thawed on the measurement day, followed by stirring and centrifugation at 13000 rpm for 3 minutes (at 4° C.). The resulting supernatant was filtered and the filtrate was analyzed by LC/MS/MS. The analysis was performed by LC/MS/MS under the following conditions.

[LC/MS/MS Conditions]

Measurement Apparatus: API-5000 (manufactured by Applied Biosystems, Inc.)

Analytical column: CAPCELL PAK CR (1:4) (4.6 mm, I.D.×250 mm, 5 μm)

Analytical column temperature: 40° C.

Flow rate: 1 mL/min

Mobile phase: A: 5 mM ammonium formate (pH 3.9), B: acetonitrile (A/B=17/3)

Scan type: MRM

Polarity: negative

Detection (levodopa): m/z (precursor): 196.19, m/z (product): 134.99

DP (Declustering Potential): −60

CE (Collision Energy): −25

CXP (Collision Cell Exit Potential): −17

[Results]

The results of the kinetic study in dogs are shown in Table 5.

TABLE 5

| Compound | Dose (mg/kg) | Dose expressed in terms of levodopa (mg/kg) | AUC (μg⁺ hr/mL) | Cmax/C6 hr |
|---|---|---|---|---|
| Levodopa | 3 | | 0.96 | 913.8 |
| Example 5 | 9.3 | 3 | 0.89 | 8.0 |
| Reference Example 6 | 10.0 | 3 | 0.66 | 14.7 |
| Reference Example 11 | 10.0 | 3 | 0.52 | 23.9 |
| Reference Example 16 | 10.7 | 3 | 0.22 | 7.4 |
| Reference Example 18 | 7.0 | 3 | 0.12 | 2.9 |
| Reference Example 19 | 7.0 | 3 | 0.70 | 221.2 |
| Reference Example 21 | 7.4 | 3 | 0.27 | 8.8 |
| Reference Example 22 | 7.8 | 3 | 0.28 | 6.6 |
| Reference Example 23 | 7.1 | 3 | 0.59 | 41.5 |

TABLE 5-continued

| Compound | Dose (mg/kg) | Dose expressed in terms of levodopa (mg/kg) | AUC (μg⁺ hr/mL) | Cmax/C6 hr |
|---|---|---|---|---|
| Reference Example 25 | 8.8 | 3 | 0.31 | 24.2 |
| Reference Example 26 | 5.6 | 3 | 0.45 | 18.0 |
| Reference Example 27 | 6.1 | 3 | 0.84 | 58.7 |
| Reference Example 28 | 6.9 | 3 | 0.68 | 304.4 |
| Reference Example 29 | 7.3 | 3 | 0.59 | 98.5 |
| Reference Example 30 | 7.8 | 3 | 0.36 | 12.8 |
| Reference Example 31 | 7.3 | 3 | 0.42 | 18.7 |
| Reference Example 32 | 7.5 | 3 | 0.53 | 40.7 |
| Reference Example 33 | 10.2 | 3 | 0.003 | 2.0 |
| Reference Example 34 | 8.9 | 3 | 0.10 | 16.1 |
| Reference Example 35 | 6.7 | 3 | 0.77 | 1039.6 |
| Reference Example 40 | 9.8 | 3 | 0.81 | 4.3 |
| Compound X | 6.8 | 3 | 0.42 | 12.6 |

In the above Table 5, as the results of the kinetic study, an "area under the blood concentration-time curve (area under the curve (AUC))" serving as an index of exposure to levodopa, and a "ratio (Cmax/C6 hr) of a plasma concentration at 6 hours after oral administration (C6 hr) and a maximum plasma concentration (Cmax)" serving as an index of a flat blood concentration-time profile of levodopa are shown. Incidentally, the numerical value in the column which indicates the dose expressed in terms of levodopa refers to a dose equivalent to that of levodopa. Since the value of AUC when levodopa was administered was 0.96, as the value of AUC is closer to this value, the ratio of the test compound which permitted exposure as levodopa is higher. Further, it is indicated that when the value of Cmax/C6 hr is larger than 1 and also closer to 1, the plasma concentration-time profile of levodopa is flatter.

The AUC and Cmax/C6 hr of the compound of the present invention (Example 5) were both favorable as compared with those of the compounds produced in Reference Examples 6, 11, 16, 18, 19, 21 to 23, and 25 to 35, and Compound X, and therefore it was confirmed that the compound of the present invention is a compound which is converted into levodopa to permit levodopa exposure at a high ratio and also provides a flat plasma concentration-time profile of levodopa.

In the case of the compounds used for comparison, for example, the compounds produced in Reference Examples 6, 11, 19, 23, 27 to 29, 32, and 35, although the value of AUC was 0.5 or larger, even the smallest value of Cmax/C6 hr was around 15, and therefore, the compounds did not provide a flat plasma concentration-time profile of levodopa.

On the other hand, in the case of the compound produced in Reference Example 40, the AUC and Cmax/C6 hr were as favorable as those of the compound of the present invention.

From the above results, it was revealed that among the group of compounds of the same kind, only the compound of the present invention and the compound produced in Reference Example 40 are compounds which are converted into levodopa at a high ratio after administration and also can provide a relatively high blood concentration of levodopa over a long period of time.

(2) Kinetic Study in Dogs (Effect of Salt or Crystal Form on Blood Kinetics)

In general, it is considered that when the salt or crystal form is different, a difference in solubility thereof or the like affects blood kinetics and sometimes causes a difference in potency of efficacy. In the previous section (1), it was confirmed that the compound of the present invention (hydrochloride, amorphous) described in Example 5 can be absorbed through oral administration, and therefore, it was confirmed as to whether or not other compounds of the present invention are absorbed through oral administration.

[Preparation of Drug Solution for Administration]

A drug solution for oral administration was prepared by weighing each of the compound of the present invention produced in Example 6 (a type A crystal of (2S)-2-amino-3-(3,4-bis((2-(benzoyloxy)-2-methylpropanoyl)oxy)phenyl) propanoic acid tosylate), the compound of the present invention produced in Example 9 (a type A crystal of (2S)-2-amino-3-(3,4-bis((2-(benzoyloxy)-2-methylpropanoyl)oxy)phenyl) propanoic acid), and the compound of the present invention produced in Example 10 (a type B crystal of (2S)-2-amino-3-(3,4-bis((2-(benzoyloxy)-2-methylpropanoyl)oxy)phenyl) propanoic acid) and suspending it in 0.5 w/v % methyl cellulose 400 at 6 mg/3 mL expressed in terms of levodopa.

[Collection of Plasma Sample]

The collection of a plasma sample was carried out according to the previous section (1). However, the dose was set to 6 mg/3 mL/kg.

[Preparation of Analytical Sample and Analysis]

The preparation of an analytical sample and analysis were carried out according to the previous section (1).

[Results]

The results of the kinetic study in dogs are shown in Table 6.

TABLE 6

| | (hr) | Example 6 | Example 9 | Example 10 |
|---|---|---|---|---|
| Concentration of levodopa in dog plasma (n = 4) | 0.25 | 0.046 (±0.030) | 0.014 (±0.010) | 0.014 (±0.005) |
| | 0.5 | 0.168 (±0.048) | 0.099 (±0.068) | 0.119 (±0.046) |
| | 1 | 0.306 (±0.126) | 0.281 (±0.148) | 0.189 (±0.069) |
| | 2 | 0.323 (±0.203) | 0.311 (±0.216) | 0.230 (±0.092) |
| | 4 | 0.129 (±0.109) | 0.155 (±0.116) | 0.136 (±0.116) |
| | 6 | 0.042 (±0.043) | 0.036 (±0.024) | 0.048 (±0.050) |
| | 8 | 0.012 (±0.012) | 0.011 (±0.005) | 0.013 (±0.012) |

In the above Table 6, a change over time in the concentration (μg/mL) of levodopa observed in the plasma when the compound of the present invention produced in Example 6, the compound of the present invention produced in Example 9, or the compound of the present invention produced in Example 10 was orally administered to dogs is shown. The numeral expressed with ± in the parenthesis represents a standard deviation.

Similarly to the case of the compound of the present invention described in Example 5 (hydrochloride, amorphous) shown in the previous section (1), all of the compound of the present invention produced in Example 6, the compound of the present invention produced in Example 9, and the compound of the present invention produced in Example 10 can be absorbed through oral administration, and also a significant difference exceeding the range of variation was not observed in the concentration of levodopa in the plasma seen after administration. From the above results, it was revealed that all of the compounds of the present invention can be orally administered regardless of the salt or crystal form, have absorbability required for exhibiting their efficacy, and can be used uniformly as pharmaceutical products.

Since the compound of the present invention is a levodopa prodrug, if it can be confirmed that levodopa is produced after the compound of the present invention is administered in vivo, it is ensured that the compound of the present invention exhibits the same efficacy as levodopa. That is, a kinetic study to confirm that levodopa is produced by administering the compound of the present invention can be considered to be equivalent to a pharmacological study to evaluate efficacy.

From the above results, it was revealed that levodopa is produced after administering the compound of the present invention in vivo, and therefore, a desired efficacy can be obtained by administering the compound of the present invention at a dose increased or decreased as needed in a pharmacological study in which levodopa exhibits its efficacy.

(3) Kinetic Study in Dogs (Combination Use with Dopa Decarboxylase Inhibitor (DCI))

It was tested how the flat blood concentration-time profile of levodopa provided by the administration of the compound of the present invention demonstrated by the results shown in the above section (1) is changed under the condition of using a widely and clinically used DCI in combination. As the DCI, carbidopa was used.

[Collection of Plasma Sample]

A drug solution for oral administration was prepared by weighing each of the compound of the present invention produced in Example 5 and levodopa and dissolving it in a vehicle at 1 mg/mL expressed in terms of levodopa.

The thus obtained drug solution was administered by gavage through a gastric tube into the stomach of dogs (male beagle dogs), which were fasted from the day before the administration, and to which an effective dose (60 mg/kg) of carbidopa (70566, AK Scientific, Inc.) was administered. The dose of levodopa was 3 mg/kg, and the dose of the compound of the present invention (Example 5) was 18.6 mg/kg (6 mg/kg expressed in terms of levodopa). At 15 and 30 minutes, and 1, 2, 4, 6, and 8 hours after administration of the drug solution, 1 mL of blood was collected from a cephalic vein with a heparinized syringe. Immediately after the collection, the collected blood was centrifuged in a desktop centrifuge at 14500 rpm for 45 seconds. Then, acetonitrile containing 0.1125% formic acid was added to the thus obtained plasma in an amount as twice as large as the volume of the plasma, followed by stirring, and then, the resulting sample was stored at −20° C. until measurement.

[Preparation of Analytical Sample and Analysis]

The preparation of an analytical sample and analysis were carried out according to the method described in the same section in the Biological Example 1(1).

[Results]

The plasma concentration-time profile of levodopa when the compound of the present invention was administered to dogs is shown in FIG. 1.

Under the condition of using carbidopa which is a widely and clinically used DCI in combination, the blood concentration-time profile of levodopa was compared between the case where levodopa was administered and the case where the compound of the present invention was administered. As a result, the plasma concentration of levodopa in the case of administering levodopa reached a maximum plasma concentration (Cmax) of 2.1 µg/mL at 15 minutes after the administration, and thereafter rapidly decreased, however, in the case of administering the compound of the present invention in place of levodopa, the plasma concentration of levodopa gradually increased and reached Cmax of 1.0 µg/mL at 4 hours after the administration, and thereafter gradually decreased.

In humans, the effective plasma concentration of levodopa at which the above-described side effects such as dyskinesia and wearing-off are not developed is considered to be within a range of from about 0.4 to 1 µg/mL according to the publications (Therapeutic Drug Monitoring, 2001, Vol. 23, pp. 621-629, Manuela Contin et al.; and Clinical Pharmacology & Therapeutics, 2001, Vol. 70, pp. 33-41, Dietz et al.).

From the results obtained in this Example, the time (duration) for which the plasma concentration of levodopa was within a range of from 0.4 to 1 µg/mL was calculated, and found to be 0.6 hours in the case of administering levodopa, and 4.3 hours in the case of administering the compound of the present invention.

From the above result, it was found that the compound of the present invention provides a sustained plasma concentration of levodopa after oral administration also under the condition of using widely and clinically used carbidopa in combination and prolongs the duration of the effective blood concentration to about 7 times longer than in the case of administering levodopa. As described above, since the organ distribution of carboxyesterase in dogs is similar to that in humans, from the results of the kinetic study using dogs, it was considered that the compound of the present invention can provide a sustained plasma concentration of levodopa also in humans.

(4) Simulation of Kinetics in Human Blood on Basis of Results of Kinetic Study in Dogs For the purpose of validating whether or not the effect of releasing levodopa over a long period of time of the compound of the present invention observed in the kinetic study in dogs is also observed in humans, a simulation of kinetics in human blood was carried out on the basis of the results of the kinetic study in dogs described in the above section (3).

[Simulation of Kinetics in Human Blood]

By using the values obtained in the kinetic study in dog blood in the above section (3), a prediction model that simulates the kinetics in human blood was constructed.

Specifically, the blood concentration-time profile of levodopa or the compound of the present invention obtained in the kinetic study in dogs was input into Phoenix WinNonlin version 6.1 (Pharsight Corporation), which is kinetic analysis software, and the fitting of the plasma concentration of levodopa was carried out, whereby a prediction model that simulates the blood kinetics of levodopa was constructed.

Into this prediction model, the values of blood kinetics when a levodopa preparation was administered to humans described in the literature (Br. J. Clin. Pharm., 1989, Vol. 28, pp. 61-69, D. R. C. Robertson et al.) were input, and the kinetics of the compound of the present invention in human blood was simulated.

[Results]

The results of the simulation of the kinetic of the compound of the present invention in human blood and the values associated with the blood kinetics of levodopa when a 100 mg tablet (containing 100 mg of levodopa) of a commercially available levodopa-carbidopa combination preparation (SINEMET (registered trademark)) was taken described in the literature (Eur. J. Clin. Pharmacol., 1993, Vol. 45, pp. 419-423, V. V. Myllyla et al.) are shown in FIG. 2.

It is known that when the plasma concentration of levodopa increases too much, dyskinesia is developed as a side effect, and when the plasma concentration of levodopa decreases too much, wearing-off is developed as a side effect. Therefore, if an intermediate plasma concentration, at which such side effects are not caused, can be continuously maintained, it can be used as an excellent method for treating Parkinson's disease and/or Parkinson's syndrome.

Similarly to the above-described analysis, the following analysis was carried out by using the range of the plasma concentration (0.4 to 1 µg/mL) of levodopa, which was derived from the publication, and in which side effects are not caused in humans, as a therapeutic range.

In the case where a 100 mg tablet (containing 100 mg of levodopa) of a commercially available levodopa-carbidopa combination preparation (SINEMET (registered trademark)) was taken, the plasma concentration of levodopa rapidly increased immediately after taking the tablet and reached the maximum plasma concentration (Cmax) which exceeds the upper limit of the therapeutic range, and thereafter rapidly decreased. The time period for which the plasma concentration of levodopa was within the therapeutic range was calculated and found to be 2.3 hours in the case where the levodopa preparation was administered.

On the other hand, the time period for which the plasma concentration of levodopa was within the therapeutic range was calculated and found to be 7.8 hours in the case where the compound of the present invention was taken at a dose of 600 mg (200 mg expressed in terms of levodopa).

Accordingly, it was found that the compound of the present invention can provide a plasma concentration of levodopa in the therapeutic range in humans for a long period of time, which is about 3.4 times longer than the currently available levodopa preparation, and particularly under the condition of using a DCI in combination, the compound of the present invention can provide a plasma concentration of levodopa in the therapeutic range over a period of about 16 hours by dosing two times per day.

Biological Example 2

Mutagenicity Assay

In the treatment of Parkinson's disease and/or Parkinson's syndrome, there is a possibility that a levodopa prodrug is continued to be taken over a long period of time of several years to several decades. Therefore, an evaluation was carried out as to whether or not the compound of the present invention has mutagenicity by a mutagenicity assay using mammalian cells.

[Method]

A mutagenicity assay using mammalian cells was carried out as a commissioning test to be undertaken by Nissin Foods Holdings Co., Ltd. The present method also called NESMAGET method is a method in which the expression of p53R2 which is a DNA repair gene is detected by luciferase activity, and the specific experimental technique is described in JP-A-2005-000024 and Japanese Patent No. 4243716. In the determination as to whether or not the result of this test was positive, the luciferase activity of p53R2 in the case of a vehicle control (0.3% dimethylsulfoxide) was taken as 100%, and a concentration at which a relative luciferase activity exceeded 200% was determined to be "concentration at which mutagenicity was determined to be positive".

[Results]

The results of the mutagenicity assay for the compound of the present invention (Example 5), the compound produced in Reference Example 6, the compound produced in Reference Example 11, the compound produced in Reference Example 16, and the compound produced in Reference Example 40 are shown in Table 7.

TABLE 7

| Compound | Mutagenicity assay (NESMAGET) Concentration at which mutagenicity was determined to be positive (µg/mL) |
|---|---|
| Example 5 | >200 |
| Reference Example 6 | 2.4 |
| Reference Example 11 | 1.4 |
| Reference Example 16 | 84 |
| Reference Example 40 | 16 |

In the case of the compound produced in Reference Example 6, the compound produced in Reference Example 11, the compound produced in Reference Example 16, and the compound produced in Reference Example 40, which showed a kinetic profile as favorable as that of the compound of the present invention in the kinetic study in dogs, the relative luciferase activity of p53R2 exceeded 200% when the concentrations thereof were 2.4, 1.4, 84, and 16 µg/mL, respectively, and therefore, these compounds were determined to be positive for mutagenicity. On the other hand, in the case of the compound of the present invention, mutagenicity was not observed even at a concentration of 200 µg/mL.

From these results, it was revealed that among levodopa prodrugs capable of providing a plasma concentration of levodopa for a long period of time, there are not a few prodrugs shown to have mutagenicity in the mutagenicity assay using mammalian cells. On the other hand, the compound of the present invention did not show mutagenicity even at a concentration of 200 µg/mL, and therefore, it was revealed that, even in the case where the compound of the present invention is continued to be taken over a long period of time of several years to several decades as in the treatment of, for example, Parkinson's disease and/or Parkinson's syndrome, the compound can be continued to be taken safely.

Biological Example 3

Model Injected with 6-Hydroxydopamine into Medial Forebrain Bundle

For the purpose of confirming that the compound of the present invention is metabolized into levodopa after oral administration and exhibited an efficacy against Parkinson's disease, the efficacy of the compound of the present invention in a model injected with 6-hydroxydopamine into the medial forebrain bundle which is an experimental Parkinson's disease model using an animal was evaluated.

[Used Animal]

In the experiment, male Crl:CD(SD)IGS rats (Charles River Japan, Inc.) supplied at 5 weeks of age were used. The rats were housed in Econ cages (4 or less rats per cage) and were raised by giving free access to solid feed CRF-1 (Oriental Yeast Co., Ltd.) and tap water (in a water bottle) until they were subjected to the experiment.

[Production of Model Injected with 6-OHDA into Medial Forebrain Bundle]

When acclimation after shipping was completed, each of the Crl:CD(SD)IGS rats at 6 weeks of age was anesthetized with pentobarbital sodium (Somnopentyl (registered trademark) injectable solution, 35 mg/kg, intraperitoneal injection). Subsequently, for the purpose of preventing damage to norepinephrine neurons by 6-hydroxydopamine (6-OHDA), desipramine (25 mg/kg) was intraperitoneally injected, and the rat was held and fixed by a brain fixation device. A small bone window was opened with a hand drill at a desired site, and 6-OHDA was injected into the medial forebrain bundle according to the brain atlas of Paxinos and Watson using a 30 G cannula (Brain Science Idea. Co. Ltd.) with a needle tip cut at an angle of 45° (site of injection: A=−4.5 mm, L=+1.2 mm, and V=−7.8 mm with respect to the bregma, injection amount: 8 μg/4 μL/8 min/site in each case). After injection, in order to prevent backflow of the solution, the injection needle was left in place for 2 minutes or more. Thereafter, the burr hole was closed with an instant glue, and then sutured and disinfected with iodine tincture.

[Confirmation of Induction of Pathology]

After two weeks from the injection of 6-OHDA, individuals in which pathology was induced were selected. Specifically, the below-described rotation test was employed, and when apomorphine (0.05 mg/kg) which is a dopamine receptor agonist was subcutaneously injected as a test substance, only rats which behaved in such a manner that the number of rotations in 5 minutes after 15 to 20 minutes from the administration was 20 or more were selected as the rats in which pathology was induced.

[Rotation Test]

In a rotation test, a device configured such that a black plastic circular cylinder having a diameter of 30 cm and a height of 35 cm was placed upright in a black-painted bowl having an opening diameter of 35 cm and a bottom diameter of 17 cm was used (the height of the curve from the bottom of the bowl to the bottom edge of the cylinder was set to 7 cm). The rat was placed in the device (one rat per device) and acclimated to the device for 30 minutes. Thereafter, a test substance was administered to the rat, and the rat was returned to the same device and videotaped. Then, the taped video was analyzed, and the number of rotations every 5 minutes or 10 minutes was measured. As for the number of rotations, a 360° rotation in one direction was determined to be one rotation. In the case where the direction (body's direction of movement or movement direction) was changed during rotation, the rotation was not included in the count.

[Examination of Effect of Compound of the Present Invention]

The rotational behavior in the case where the compound of the present invention produced in Example 5 (100 mg/kg expressed in terms of levodopa) was orally administered after a lapse of 1 week or more from when the induction of pathology was confirmed was evaluated until 6 hours after the administration (N=11). Further, the rotational behavior in the case where levodopa (30 mg/kg) was orally administered was also evaluated until 6 hours after the administration in the same manner (N=11, crossover trial). Incidentally, in each case, benserazide which is a dopa decarboxylase inhibitor (8 mg/kg) was orally administered concomitantly.

[Results]

The number of rotations (times) per 10 minutes made by the rats until 6 hours (360 minutes) after the administration in the administration group treated with levodopa (30 mg/kg) and in the administration group treated with the compound of the present invention produced in Example 5 (100 mg/kg expressed in terms of levodopa) is shown in FIG. 3. In the drawing, the values of the administration group treated with levodopa (30 mg/kg) are indicated by L-dopa (30 mg/kg), and the values of the administration group treated with the compound of the present invention produced in Example 5 (100 mg/kg expressed in terms of levodopa) are indicated by Compound of Ex. 5 (100 mg/kg). In addition, the respective values are each a mean of the values obtained using 11 rats in each group and its standard error.

In the case of the rats in the administration group treated with levodopa, the number of rotations increased rapidly after the administration and reached a maximum value (the number of rotations: about 100 times) at 20 minutes after the administration. On the other hand, in the case of the rats in the administration group treated with the compound of the present invention produced in Example 5, the number of rotations began to increase gradually after a lapse of 60 minutes or more from the administration, and reached a maximum value (the number of rotations: about 90 times or more) at 140 minutes after the administration. In addition, even when the compound of the present invention produced in Example 9 was used in place of the compound of the present invention produced in Example 5, the same results were obtained.

From the above results, it was found that the compound of the present invention exhibited the same activity as in the case of administering levodopa after a lapse of a certain period of time from oral administration. These results are consistent with the characteristic of the compound of the present invention that the compound of the present invention does not exhibit the levodopa-like activity per se, but is metabolized into levodopa and exhibits the efficacy.

Preparation Example 1

Tablet Containing 5 mg of (2S)-2-amino-3-(3,4-bis ((2-(benzoyloxy)-2-methylpropanoyl)oxy)phenyl) propanoic acid The respective components shown below were mixed according to a common procedure, followed by tableting, whereby 10000 tablets each containing 5 mg of the active ingredient were obtained.

(2S)-2-amino-3-(3,4-bis((2-(benzoyloxy)-2-methylpropanoyl)oxy)phenyl)propanoic acid: 50 g
carboxymethyl cellulose calcium (disintegrant): 20 g
magnesium stearate (lubricant): 10 g
microcrystalline cellulose: 920 g Preparation Example 2

Injectable Preparation Containing 20 mg of (2S)-2-amino-3-(3,4-bis((2-(benzoyloxy)-2-methylpropanoyl)oxy)phenyl)propanoic acid The respective components shown below were mixed according to a common procedure, and the resulting solution was sterilized according to a common procedure. Then, 5 mL aliquots of the solution were charged into ampoules, and lyophilized according to a common procedure, whereby 10000 ampoules each containing 20 mg of the active ingredient were obtained.

(2S)-2-amino-3-(3,4-bis((2-(benzoyloxy)-2-methylpropanoyl)oxy)phenyl)propanoic acid: 200 g
mannitol: 20 g
distilled water: 50 L

INDUSTRIAL APPLICABILITY

The compound of the present invention is a levodopa prodrug, and is useful as a preventive and/or therapeutic agent for diseases, for which levodopa is used as a therapeutic agent, or against which levodopa is expected to have an effect, such as Parkinson's disease and/or Parkinson's syndrome, or diseases, which are expected to be improved by dopamine stimulation, or diseases, which are induced by a decrease in noradrenaline.

The invention claimed is:

1. (2S)-2-Amino-3-(3,4-bis((2-(benzoyloxy)-2-methylpropanoyl)oxy)phenyl)propanoic acid, a salt thereof, or a solvate thereof.

2. The compound according to claim 1, which is (2S)-2-amino-3-(3,4-bis((2-(benzoyloxy)-2-methylpropanoyl)oxy)phenyl)propanoic acid, (2S)-2-amino-3-(3,4-bis((2-(benzoyloxy)-2-methylpropanoyl)oxy)phenyl)propanoic acid tosylate, or (2S)-2-amino-3-(3,4-bis((2-(benzoyloxy)-2-methylpropanoyl)oxy)phenyl)propanoic acid hydrochloride.

3. The compound according to claim 2, which is crystalline (2S)-2-amino-3-(3,4-bis((2-(benzoyloxy)-2-methylpropanoyl)oxy)phenyl)propanoic acid.

4. The compound according to claim 3, which has a melting point of from about 177.0° C. to about 181.9° C.

5. The compound according to claim 3, which has at least peaks at 2θ of about 4.03, 7.21, 9.98, 10.72, 17.93, and 19.20 degrees in a powder X-ray diffraction spectrum.

6. The compound according to claim 5, which has peaks at 2θ of about 4.03, 7.21, 9.98, 10.72, 11.93, 12.90, 13.48, 14.65, 15.23, 15.99, 16.56, 17.23, 17.93, 19.20, 20.88, 21.66, 22.36, 22.50, and 24.58 degrees in a powder X-ray diffraction spectrum.

7. The compound according to claim 6, characterized by a powder X-ray diffraction spectrum chart shown in FIG. 4.

8. The compound according to claim 3, which has an exothermic peak at about 148.7° C. and also has endothermic peaks at about 184.7° C., about 194.7° C., and about 200.3° C. in differential scanning calorimetry.

9. The compound according to claim 8, characterized by a differential scanning calorimetry chart shown in FIG. 5.

10. The compound according to claim 3, which has a melting point of from about 174.7° C. to about 179.0° C.

11. The compound according to claim 3, which has at least a peak at 2θ of about 4.62 degrees in a powder X-ray diffraction spectrum.

12. The compound according to claim 11, which has peaks at 2θ of about 4.62, 8.40, 9.54, 12.08, 15.38, and 18.16 degrees in a powder X-ray diffraction spectrum.

13. The compound according to claim 12, characterized by a powder X-ray diffraction spectrum chart shown in FIG. 7.

14. The compound according to claim 3, which has an exothermic peak at about 183.3° C. and also has endothermic peaks at about 192.2° C. and about 200.8° C. in differential scanning calorimetry.

15. The compound according to claim 14, characterized by a differential scanning calorimetry chart shown in FIG. 8.

16. The compound according to claim 2, which is crystalline (2S)-2-amino-3-(3,4-bis((2-(benzoyloxy)-2-methylpropanoyl)oxy)phenyl)propanoic acid tosylate.

17. The compound according to claim 16, which has a melting point of from about 132.0° C. to about 136.0° C.

18. The compound according to claim 16, which has at least peaks at 2θ of about 10.97, 11.58, 14.83, 16.36, 16.70, 19.42, 20.58, and 21.69 degrees in a powder X-ray diffraction spectrum.

19. The compound according to claim 18, which has peaks at 2θ of about 5.15, 6.97, 7.46, 10.97, 11.58, 13.74, 14.83, 15.20, 16.10, 16.36, 16.70, 17.35, 18.30, 18.83, 19.42, 19.95, 20.58, 21.69, 22.63, 22.84, and 24.00 degrees in a powder X-ray diffraction spectrum.

20. The compound according to claim 19, characterized by a powder X-ray diffraction spectrum chart shown in FIG. 10.

21. The compound according to claim 16, which has an endothermic peak at about 135.95° C. in differential scanning calorimetry.

22. The compound according to claim 21, characterized by a differential scanning calorimetry chart shown in FIG. 11.

23. The compound according to claim 16, which has a melting point of from about 132.3° C. to about 135.3° C.

24. The compound according to claim 16, which has at least peaks at 2θ of about 10.01, 11.88, 13.87, 15.01, 15.87, 16.07, 17.81, 18.65, 19.17, and 22.11 degrees in a powder X-ray diffraction spectrum.

25. The compound according to claim 24, which has peaks at 2θ of about 4.04, 5.04, 5.54, 6.11, 6.60, 7.96, 8.62, 10.01, 10.32, 11.88, 12.88, 13.87, 15.01, 15.87, 16.07, 16.74, 17.17, 17.81, 18.65, 19.17, 19.72, 20.27, 20.93, 21.67, 22.11, 22.56, 23.11, 23.47, and 24.21 degrees in a powder X-ray diffraction spectrum.

26. The compound according to claim 25, characterized by a powder X-ray diffraction spectrum chart shown in FIG. 13.

27. The compound according to claim 16, which has an endothermic peak at about 134.54° C. in differential scanning calorimetry.

28. The compound according to claim 27, characterized by a differential scanning calorimetry chart shown in FIG. 14.

29. The compound according to claim 2, which is amorphous (2S)-2-amino-3-(3,4-bis((2-(benzoyloxy)-2-methylpropanoyl)oxy)phenyl)propanoic acid hydrochloride.

30. The compound according to claim 29, which has a melting point of from about 112.0° C. to about 117.0° C.

31. The compound according to claim 29, characterized by a powder X-ray diffraction spectrum chart shown in FIG. 16.

32. The compound according to claim 29, which has an endothermic peak at about 82.83° C. in differential scanning calorimetry.

33. The compound according to claim 32, characterized by a differential scanning calorimetry chart shown in FIG. 17.

34. A pharmaceutical composition comprising (2S)-2-amino-3-(3,4-bis((2-(benzoyloxy)-2-methylpropanoyl)oxy)phenyl)propanoic acid, a salt thereof, or a solvate thereof, and one or more pharmaceutically acceptable carriers.

35. The pharmaceutical composition according to claim 34, which is a preventive and/or therapeutic agent for Parkinson's disease and/or Parkinson's syndrome.

36. A medicament comprising a combination of (2S)-2-amino-3-(3,4-bis((2-(benzoyloxy)-2-methylpropanoyl)oxy)phenyl)propanoic acid, a salt thereof, or a solvate thereof, and an aromatic L-amino acid decarboxylase inhibitor, and/or a catechol-O-methyltransferase inhibitor.

37. The medicament according to claim 36, wherein the aromatic L-amino acid decarboxylase inhibitor is carbidopa hydrate or benserazide hydrochloride.

38. The medicament according to claim 36, wherein the catechol-O-methyltransferase inhibitor is entacapone, tolcapone, nitecapone, BIA-3-202, or CGP-28014.

39. The medicament according to claim 36, which is a combination preparation.

40. A compound, which is (2S)-2-Amino-3-(3,4-bis((2-(benzoyloxy)-2-methylpropanoyl)oxy)phenyl)propanoic acid.

41. A method for treating Parkinson's disease and/or Parkinson's syndrome, comprising administering to a subject in need thereof a pharmaceutical composition according to claim 34.

42. A method for treating Parkinson's disease and/or Parkinson's syndrome, comprising administering to a mammal an effective amount of (2S)-2-amino-3-(3,4-bis((2-(benzoyloxy)-2-methylpropanoyl)oxy)phenyl)propanoic acid, a salt thereof, or a solvate thereof.

43. The method for treating Parkinson's disease and/or Parkinson's syndrome according to claim 42, which further comprises administering an effective amount of an aromatic L-amino acid decarboxylase inhibitor and/or a catechol-O-methyltransferase inhibitor.

44. A method for treating Parkinson's disease and/or Parkinson's syndrome, comprising administering to a mammal an effective amount of (2S)-2-amino-3-(3,4-bis((2-(benzoyloxy)-2-methylpropanoyl)oxy)phenyl)propanoic acid.

* * * * *

UNITED STATES PATENT AND TRADEMARK OFFICE
CERTIFICATE OF CORRECTION

| | |
|---|---|
| PATENT NO. | : 8,748,485 B2 |
| APPLICATION NO. | : 13/991025 |
| DATED | : June 10, 2014 |
| INVENTOR(S) | : Masaya Kokubo et al. |

It is certified that error appears in the above-identified patent and that said Letters Patent is hereby corrected as shown below:

IN THE CLAIMS:

Column 79, line 17, reads "peaks at 2θ of", should read --peaks at 2θ of--;

Column 79, line 20, reads "2θ of about", should read --2θ of about--;

Column 79, line 36, reads "a peak of 2θ", should read --a peak of 2θ--;

Column 79, line 39 reads "at 2θ of about", should read --at 2θ of about--;

Column 79, line 55 reads "least peaks at 2θ", should read --least peaks at 2θ--;

Column 79, line 59 reads "at 2θ of about", should read --at 2θ of about--;

Column 80, line 6 reads "least peaks at 2θ", should read --least peaks at 2θ--;

Column 80, line 10 reads "at 2θ of about", should read --at 2θ of about--.

Signed and Sealed this
Fifth Day of May, 2015

Michelle K. Lee
*Director of the United States Patent and Trademark Office*